US010086108B2

(12) United States Patent
Schneider et al.

(10) Patent No.: US 10,086,108 B2
(45) Date of Patent: Oct. 2, 2018

(54) HYDROGELS AND USE THEREOF IN ANASTOMOSIS PROCEDURES

(71) Applicants: The United States of America, as represented by the Secretary, Department of Health and Human Services, Washington, DC (US); The Johns Hopkins University, Baltimore, MD (US)

(72) Inventors: Joel Schneider, Middletown, MD (US); Gerald Brandacher, Baltimore, MD (US); Daniel Smith, West Chester, PA (US); Gabriel Brat, Baltimore, MD (US); Johanna Grahammer, Innsbruck (AT)

(73) Assignees: The United States of America, as represented by the Secretary, Department of Health and Human Services, Washington, DC (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/545,647

(22) PCT Filed: Jan. 22, 2016

(86) PCT No.: PCT/US2016/014534
§ 371 (c)(1),
(2) Date: Jul. 21, 2017

(87) PCT Pub. No.: WO2016/118871
PCT Pub. Date: Jul. 28, 2016

(65) Prior Publication Data
US 2018/0000983 A1  Jan. 4, 2018

Related U.S. Application Data

(60) Provisional application No. 62/106,548, filed on Jan. 22, 2015.

(51) Int. Cl.
*A61K 38/00* (2006.01)
*A61L 24/00* (2006.01)
*A61L 24/10* (2006.01)
*A61B 17/11* (2006.01)

(52) U.S. Cl.
CPC .......... *A61L 24/0031* (2013.01); *A61B 17/11* (2013.01); *A61L 24/001* (2013.01); *A61L 24/108* (2013.01); *A61B 2017/1107* (2013.01); *A61B 2017/1132* (2013.01); *A61L 2400/06* (2013.01)

(58) Field of Classification Search
None
See application file for complete search history.

(56) References Cited

U.S. PATENT DOCUMENTS

| | | | |
|---|---|---|---|
| 5,141,516 A | 8/1992 | Detweiler | |
| 5,258,042 A | 11/1993 | Mehta | |
| 6,110,188 A | 8/2000 | Narciso, Jr. | |
| 7,858,585 B2 | 12/2010 | Ozbas et al. | |
| 7,884,185 B2 * | 2/2011 | Schneider | A61K 430/325 |
| 8,221,773 B2 | 7/2012 | Schneider et al. | |
| 2002/0052572 A1 | 5/2002 | Franco et al. | |

FOREIGN PATENT DOCUMENTS

| | | |
|---|---|---|
| WO | WO 2006/076042 | 7/2006 |
| WO | WO 2007/059491 | 5/2007 |
| WO | WO 2007/148334 | 12/2007 |
| WO | WO 2009/117497 | 9/2009 |
| WO | WO 2010/017369 | 2/2010 |
| WO | WO 2010/151353 | 12/2010 |
| WO | WO 2011/112856 | 9/2011 |

OTHER PUBLICATIONS

Altunbas, et al. "Encapsulation of curcumin in self-assembling peptide hydrogels as injectable drug delivery vehicles." *Biomaterials* 32, No. 25 (2011): 5906-5914.
Branco, et al. "Fast dynamics of semiflexible chain networks of self-assembled peptides." *Biomacromolecules* 10, No. 6 (2009): 1374-1380.
Branco, et al. "The effect of protein structure on their controlled release from an injectable peptide hydrogel." *Biomaterials* 31, No. 36 (2010): 9527-9534.
Chang, et al. "Vascular anastomosis using controlled phase transitions in poloxamer gels." *Nature Medicine* 17, No. 9 (2011): 1147-1152.
Erdmann, et al. "Side-to-side sutureless vascular anastomosis with magnets." *Journal of Vascular Surgery* 40, No. 3 (2004): 505-511.
Figlio, et al. "Properties of gelatin as a temporary intravascular stent." *Transactions—Am. Soc. Artificial Internal Organs*, 9 (1963): 321-323.
Giano, et al. "Controlled biodegradation of self-assembling β-hairpin peptide hydrogels by proteolysis with matrix metalloproteinase-13." *Biomaterials* 32, No. 27 (2011): 6471-6477.
Haines, et al. "Light-activated hydrogel formation via the triggered folding and self-assembly of a designed peptide." *Journal of the American Chemical Society* 127, No. 48 (2005): 17025-17029.

(Continued)

Primary Examiner — Jeanette M Lieb
(74) *Attorney, Agent, or Firm* — Klarquist Sparkman, LLP

(57) ABSTRACT

This disclosure provides novel hydrogels that can undergo multiple gel-sol transitions and methods of making and using such hydrogels, particularly in anastomosis procedures. The peptide hydrogels comprising a fibrillar network of peptides that are in an amphiphilic β-hairpin conformation. The peptides comprise photo-caged glutamate residues with a neutral photocage that can be photolytically selectively uncaged to disrupt the fibrillar network and trigger an irreversible gel-sol phase transition of the hydrogel. Isolated peptides for making the disclosed hydrogels are provided, as are methods of using the peptide hydrogels in anastomosis procedures.

25 Claims, 36 Drawing Sheets

(56) References Cited

OTHER PUBLICATIONS

Haines-Butterick, et al. "Controlling hydrogelation kinetics by peptide design for three-dimensional encapsulation and injectable delivery of cells." *Proceedings of the National Academy of Sciences* 104, No. 19 (2007): 7791-7796.

He, et al, "Assessment of tissue blood flow following small artery welding with an intraluminal dissolvable stent." *Microsurgery* 19, No. 3 (1999): 148-152.

Hule, et al. "Correlations between structure, material properties and bioproperties in self-assembled β-hairpin peptide hydrogels." *Faraday Discussions* 139 (2008): 251-264.

Larsen, et al. "Sequence-dependent gelation kinetics of β-hairpin peptide hydrogels." *Macromolecules* 42, No. 21 (2009): 8443-8450.

Lauto, et al. "Self-expandable chitosan stent: design and preparation." *Biomaterials* 22, No. 13 (2001): 1869-1874.

Liu, et al. "Experimental study of one-shot vascular anastomostic device for proximal vein graft anastomoses." *The Annals of Thoracic Surgery* 82, No. 1 (2006): 303-306.

McCargar, et al. "Preparation of dissolvable albumin stents for vascular anastomosis with a 1.9 µm laser and in vitro mechanical strength assessments." *Lasers in Surgery and Medicine* 44, No. 4 (2012): 330-338.

Measey, et al. "Light-triggered disassembly of amyloid fibrils." *Langmuir* 28, No. 34 (2012): 12588-12592.

Nagarkar, et al. "De novo design of strand-swapped β-hairpin hydrogels." *Journal of the American Chemical Society* 130, No. 13 (2008): 4466-4474.

Nagy, et al. "Enhanced mechanical rigidity of hydrogels formed from enantiomeric peptide assemblies." *Journal of the American Chemical Society* 133, No. 38 (2011): 14975-14977.

Rancic, et al. "Less invasive (common) femoral artery aneurysm repair using endografts and limited dissection." *European Journal of Vascular and Endovascular Surgery* 45, No. 5 (2013): 481-487.

Rughani, et al. "De novo design of a shear-thin recoverable peptide-based hydrogel capable of intrafibrillar photopolymerization," *Macromolecules* 43, No. 19 (2010): 7924-7930.

Salick, et al. "Design of an Injectable β-Hairpin Peptide Hydrogel That Kills Methicillin-Resistant *Staphylococcus aureus*." *Advanced Materials* 21, No. 41 (2009): 4120-4123.

Salick, et al. "Inherent antibacterial activity of a peptide-based β-hairpin hydrogel." *Journal of the American Chemical Society* 129, No. 47 (2007): 14793-14799.

Sathaye, et al. "Rheology of peptide-and protein-based physical hydrogels: Are everyday measurements just scratching the surface?." *Wiley Interdisciplinary Reviews: Nanomedicine and Nanobiotechnology* 7, No. 1 (2015): 34-68.

Schneider, et al. "Responsive hydrogels from the intramolecular folding and self-assembly of a designed peptide." *Journal of the American Chemical Society* 124, No. 50 (2002): 15030-15037.

Shao, et al. "Photoactive molecules for applications in molecular imaging and cell biology." *Chemical Society Reviews* 39, No. 8 (2010): 2835-2846.

Sinthuvanich, et al. "Iterative design of peptide-based hydrogels and the effect of network electrostatics on primary chondrocyte behavior." *Biomaterials* 33, No. 30 (2012): 7478-7488.

Smith, et al. "A multi-phase transitioning peptide hydrogel for suturing ultra-small vessels." *Nature Nanotechnology* 11, No. 1 (2016): 95-102.

Taam, et al. "Preliminary experimental study of a mechanical connector allowing vascular anastomosis." *Annals of Vascular Surgery* 27, No. 5 (2013): 638-645.

Veiga, et al. "Arginine-rich self-assembling peptides as potent antibacterial gels." *Biomaterials* 33, No. 35 (2012): 8907-8916.

Wang, et al. "A dissolvable intralumental stent for sutureless vascular anastomosis." In *Key Engineering Materials*, vol. 288, pp. 575-578. Trans Tech Publications, 2005.

Werker, et al. "Review of facilitated approaches to vascular anastomosis surgery." *The Annals of Thoracic Surgery* 63, No. 6 (1997): S122-S127.

Wouters, et al. "An analysis of side chain interactions and pair correlations within antiparallel β-sheets: the differences between backbone hydrogen-bonded and non-hydrogen-bonded residue pairs." *Proteins: Structure, Function, and Bioinformatics* 22, No. 2 (1995): 119-131.

Yan, et al. "Injectable solid hydrogel: mechanism of shear-thinning and immediate recovery of injectable β-hairpin peptide hydrogels." *Soft Matter* 6, No. 20 (2010): 5143-5156.

Yan, et al. "Injectable solid peptide hydrogel as a cell carrier: effects of shear flow on hydrogels and cell payload." *Langmuir* 28, No. 14 (2012): 6076-6087.

Yucel, et al. "Direct observation of early-time hydrogelation in β-hairpin peptide self-assembly." *Macromolecules* 41, No. 15 (2008): 5763-5772.

Zhao, et al. "Evaluation of a novel thermosensitive heparin-poloxamer hydrogel for improving vascular anastomosis quality and safety in a rabbit model." *PloS One* 8, No. 8 (2013): e73178.

\* cited by examiner

APC1: Ac-VKVKVKGKV$^D$PPTKZEVKVKV-NH$_2$
APC2: Ac-VKVKGKVKV$^D$PPTKVEZKVKV-NH$_2$   Z = MNI-Glu
cAPC1: Ac-VKVKVKGKV$^D$PPTKEEVKVKV-NH$_2$
cAPC2: Ac-VKVKGKVKV$^D$PPTKVEEKVKV-NH$_2$

FIG. 7A
FIG. 7B
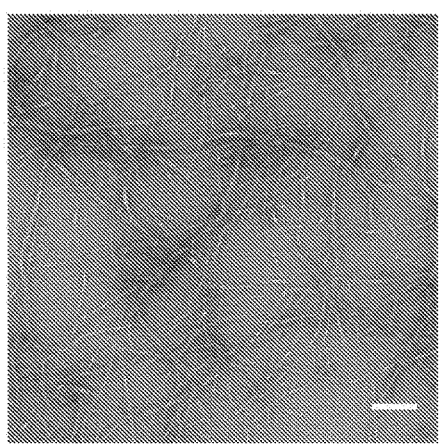 $\xrightarrow{h\nu}$ 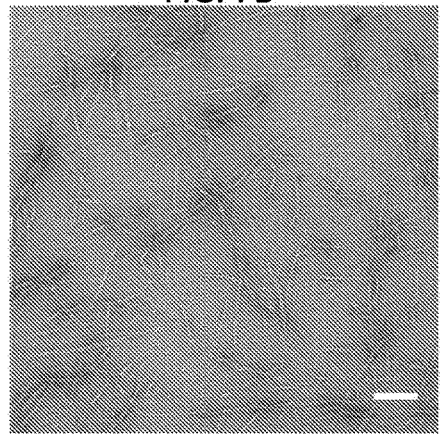
365 nm
FIG. 7C
FIG. 7D
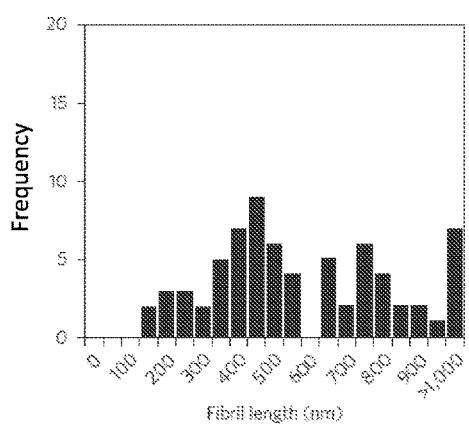
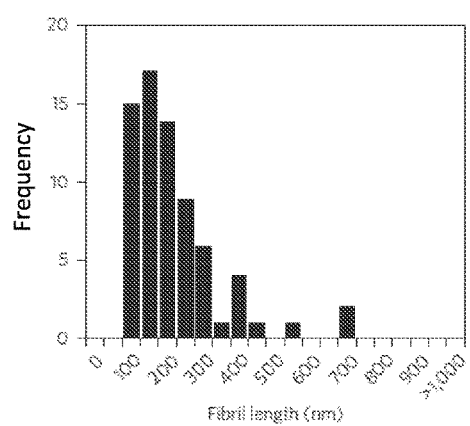

HYDROGELS AND USE THEREOF IN ANASTOMOSIS PROCEDURES

CROSS REFERENCE TO RELATED APPLICATIONS

This is the U.S. National Stage of International Application no. PCT/US2016/014534, filed Jan. 22, 2016, which was published in English under PCT Article 21(2), which in turn claims benefit of U.S. Provisional Application No. 62/106,548, filed Jan. 22, 2015. The provisional application is incorporated by reference herein in its entirety.

FIELD OF THE DISCLOSURE

This relates to hydrogels that can undergo multiple gel-to-solution (gel-sol) and solution-to-gel (sol-gel) phase transitions, and their use in anastomosis procedures.

BACKGROUND

Anastomosis, the surgical joining of two luminal structures within the body, is a common and clinically vital procedure used by nearly all surgeons. For example, anastomosis procedures can be utilized for the end-to-end joining of severed blood vessels, lymphatic vessels, and ducts. Typical anastomosis of large vessels can be carried out by skilled surgeons with relative ease. However, as the vessels to be anastomosed become smaller or less firm, surgeons experience increasing rates of complications and failure, even among those who are highly specialized and extensively trained in vascular- or micro-surgery. In addition to their small size, severed micro-vessels tend to contract (arteries) or have collapsed ends (veins, lymphatic vessels, ducts), making their suturing extremely difficult and ultimately limiting applicability of microsurgical reconstructive techniques and procedures.

Degradable stents and tissue adhesives have been developed as alternatives to classic suturing methods of anastomosis. Degradable intraluminal stents have the advantage of being biocompatible and easily fabricated to match the size of the vessel. In some examples, these materials can be eliminated from the vessel following the anastomosis either by inducing an active temperature-dependent gel-sol phase transition or by relying on dissolution of the material by blood. However, while these materials do facilitate the suturing procedure, their utility is diminished by the requirement for careful control of temperature and/or the long dissolution times required for their removal.

Thus, there is a need for new materials that can be applied rapidly and used to support a vessel in an open configuration for an anastomosis procedure, and which can be degraded or removed without dependency on temperature or slow dissolution by blood.

SUMMARY

This disclosure provides a peptide-based hydrogel capable of undergoing multiple consecutive gel-sol and sol-gel phase transitions enabling its use as a temporary intraluminal stent during anastomosis procedures. The peptide in the hydrogel is self-assembling, and an aqueous solution containing the peptide can be triggered to undergo an initial sol-gel phase transition directly in a syringe. The resulting solid-like hydrogel is characterized by shear-thin/recovery rheological properties. Shear-thinning converts the solid-like gel into a viscous gel capable of flow. Cessation of shear stress results in gel recovery. This property allows the gel to be delivered by syringe to the collapsed lumen of vessels where it re-establishes vessel shape, greatly aiding the suturing of the vessel. The transparent gel can also be applied to the interspace between vessel ends, providing a flexible medium into which the vessels can be inserted, physically manipulated, but temporally fixed after placement. In several embodiments, this allows clamp-free approximation with minimal lumina handling. Suturing can be performed directly through the transparent shear-thinning gel medium. On completion, gel applied external to the vessel can be washed away. Gel within the vessel can be triggered to initiate its final gel-sol phase transition by selective irradiation with an appropriate wavelength of light, blood flow through the vessel disperses the disrupted gel and restores patency to the vessel.

Several embodiments include a peptide hydrogel comprising a fibrillar network of peptides. The peptides are in an amphiphilic β-hairpin conformation and comprise photocaged glutamate residues with a neutral photocage that can be photolytically selectively uncaged. The peptide hydrogel can undergo a gel-sol phase transition to a low viscosity gel capable of flow upon application of shear stress, and a subsequent sol-gel phase transition to a hydrogel that does not flow upon cessation of the shear. Uncaging the glutamate residue disrupts the fibrillar network and triggers an irreversible gel-sol phase transition of the hydrogel. In several embodiments, the amphiphilic β-hairpin conformation of the peptide comprises a β-turn, a first β-strand, a second β-strand, a hydrophobic face, and a hydrophilic face. The first β-strand comprises the photocaged glutamate residue, the second β-strand comprises a glycine residue, and the sidechains of the photocaged glutamate residue and the glycine residue are proximal to each other on the hydrophobic faces of the peptides. Assembly of the peptides in the fibrillar network of the hydrogel comprises hydrophobic interactions between the hydrophobic faces of the peptides. Thus, uncaging the photocaged glutamate residues disrupts the hydrophobic interactions between the peptides by exposing the negative charges of the glutamate residues, thereby disrupting the fibrillar network and triggering the gel-sol phase transition of the hydrogel.

In some embodiments, the peptide hydrogel can include from about 20 mM to about 400 mM NaCl. In additional embodiments, the peptide hydrogel can include a pH of from about 7.0 to about 9.0. In additional embodiments, the peptide hydrogel can include from about 0.25% weight/volume (w/v) to about 4.0% w/v of the peptide. For example, in some embodiments, the peptide hydrogel can include from about 20 mM to about 400 mM NaCl, a pH of from about 7.0 to about 9.0, and from about 0.25% weight/volume (w/v) to about 4.0% w/v of the peptide.

In some embodiments, the peptide included in the peptide hydrogel can be from 10 to 75 amino acids in length. In some non-limiting examples, the peptide included in the peptide hydrogel can comprise or consist of an APC1 peptide. In more embodiments, the photocaged glutamate residue on the peptide included in the peptide hydrogel is a 4-methoxy-7-nitroindolinyl-glutamate residue.

Containers, such as a syringe, containing the disclosed peptide hydrogels are also provided.

In additional embodiments, a peptide is provided that can form an amphiphilic β-hairpin conformation comprising a β-turn, a first β-strand, a second β-strand, a hydrophobic face, and a hydrophilic face when the peptide is dissolved in an aqueous solution comprising 150 mM NaCl and a pH of 7.4 at 25° C. The first β-strand comprises a photocaged glutamate residue with a neutral photocage, the second β-strand comprises a glycine residue, and the sidechains of the photocaged glutamate residue and the glycine residue are proximal to each other on the hydrophobic face of the peptide. In several embodiments, an aqueous solution containing 2% w/v of the peptide and 150 mM NaCl and a pH of 7.4 can form a peptide hydrogel comprising a fibrillar network of a plurality of the peptide when incubated at 25° C. in a container. The peptides assemble in the fibrillar network by hydrophobic interactions between the hydrophobic faces of the peptides, and uncaging the photocaged glutamate residues on the peptides disrupts the hydrophobic interactions between the peptides by exposing the negative charges of the glutamate residues, thereby disrupting the fibrillar network and triggering an irreversible gel-sol phase transition of the hydrogel. In some embodiments, the peptide can be from 10 to 75 amino acids in length. In some non-limiting examples, the peptide included in the peptide hydrogel can comprise or consist of an ACP1 peptide. In more embodiments, the photocaged glutamate residue on the peptide included in the peptide hydrogel is a 4-methoxy-7-nitroindolinyl-glutamate residue.

Methods of performing an anastomosis using the disclosed peptide hydrogels are also provided. The method can comprise filling the lumen of each end of a severed vessel in a subject with a disclosed peptide hydrogel to support each end in an open configuration, apposing the two ends of the severed vessel and anastomosing the opposed ends. In additional embodiments, the method can further include applying the hydrogel to an interspace between the vessel ends (such as between and around the vessel ends) to stabilize the position of vessel ends during the anastomosis procedure. The method also includes irradiating the hydrogel (e.g., endoluminally or transmurally) with a sufficient amount of light of a preselected wavelength to uncage the photocaged glutamate residue and trigger a gel-sol phase transition of the hydrogel to a low viscosity gel capable of flow, wherein blood flow through the vessel disperses the disrupted gel and restores patency to the vessel. Thus, in some embodiments, the wall of the vessel is sufficiently thin and/or translucent to allow exposure of the photocaged glutamate to the irradiating light. In some embodiments, the vessel can have a diameter of from about 50 μM to about 10 mM. The method can include end-to-end suturing of a severed blood vessel, a severed duct, or a severed lymphatic vessel, for example.

The foregoing and other features and advantages of this disclosure will become more apparent from the following detailed description of several embodiments which proceeds with reference to the accompanying figures.

BRIEF DESCRIPTION OF THE FIGURES

FIGS. 7A-7D show transmission electron microscopy analysis of fibrils isolated from a 1% w/v APC1 hydrogel (A) before and (B) after photolysis. Scale bar=100 nm. Distribution of measured lengths of fibrils from a 1% w/v APC1 gel (C) before and (D) after photolysis, n=70 for both panels.

FIG. 8A, Collapsed femoral artery of a mouse (black arrow). FIG. 8B, OCT of the severed vessel cross-section. The collapsed vessel lumen is indicated by a dashed line. The image was collected at the region of the vessel indicated by the dashed line in 8A. FIG. 8C, Distended end with open lumen of artery after injection of 2 wt % APC1 hydrogel (black arrow). FIG. 8D, OCT of the vessel cross-section showing the distended lumen (dashed circle). The vessel was imaged at the region indicated by the dashed line in 8C. FIG. 8E, Horizontal cross-section of the proximal (left) and distal (right) vessel walls showing open lumina (dashed lines) after hydrogel injection. Imaging was performed on individual vessel ends due to the size limitation of the OCT instrument's field of view (~1.5× 1.5 mm$^2$). FIG. 8F, OCT volume Doppler depiction of anastomosed artery after irradiation (lighter regions indicate uncompromised blood flow through the suture site). FIG. 8G, Macroscopic appearance of anastomosed femoral artery with normal blood flow.

FIG. 9A, Micro-CT three-dimensional rendering showing contrast agent perfusion through the anastomosed site including the distal femoral artery (arrow) and its bifurcation into the fibular (*) and tibial (**) arteries. Scale bar, 2.5 mm. FIG. 9B, The tibial artery (arrow) in its anatomical course within the lower leg and ankle area. Scale bar, 2.0 mm. FIG. 9C, The most distal aspects of tibial blood supply to the footpad and individual toes (e.g., arrows). Scale bar, 0.5 mm. FIG. 9D, A dissected anastomosed limb after polymer diffusion. FIG. 9E, Contralateral non-anastomosed control limb. FIG. 9F, Polymer perfusion to individual toes. FIGS. 9G-9I, Real-time perfusion of indocyanine green (ICG) dye through the vasculature of an explanted mouse hind limb after irradiation of an implanted APC1 hydrogel: distribution of ICG, 2 s (9G), 7 s (9H) and 33 s (9I) after injection. Arrows indicate the initial site of injection (arrow 1), the most distal location of the dye from the injection site (arrow 2), perfusion through another major vessel (arrow 3) and a minor obstruction (arrow 4) that did not affect perfusion. Scale bars (FIGS. 9G-9I), 4 mm.

DETAILED DESCRIPTION

Figure 1:
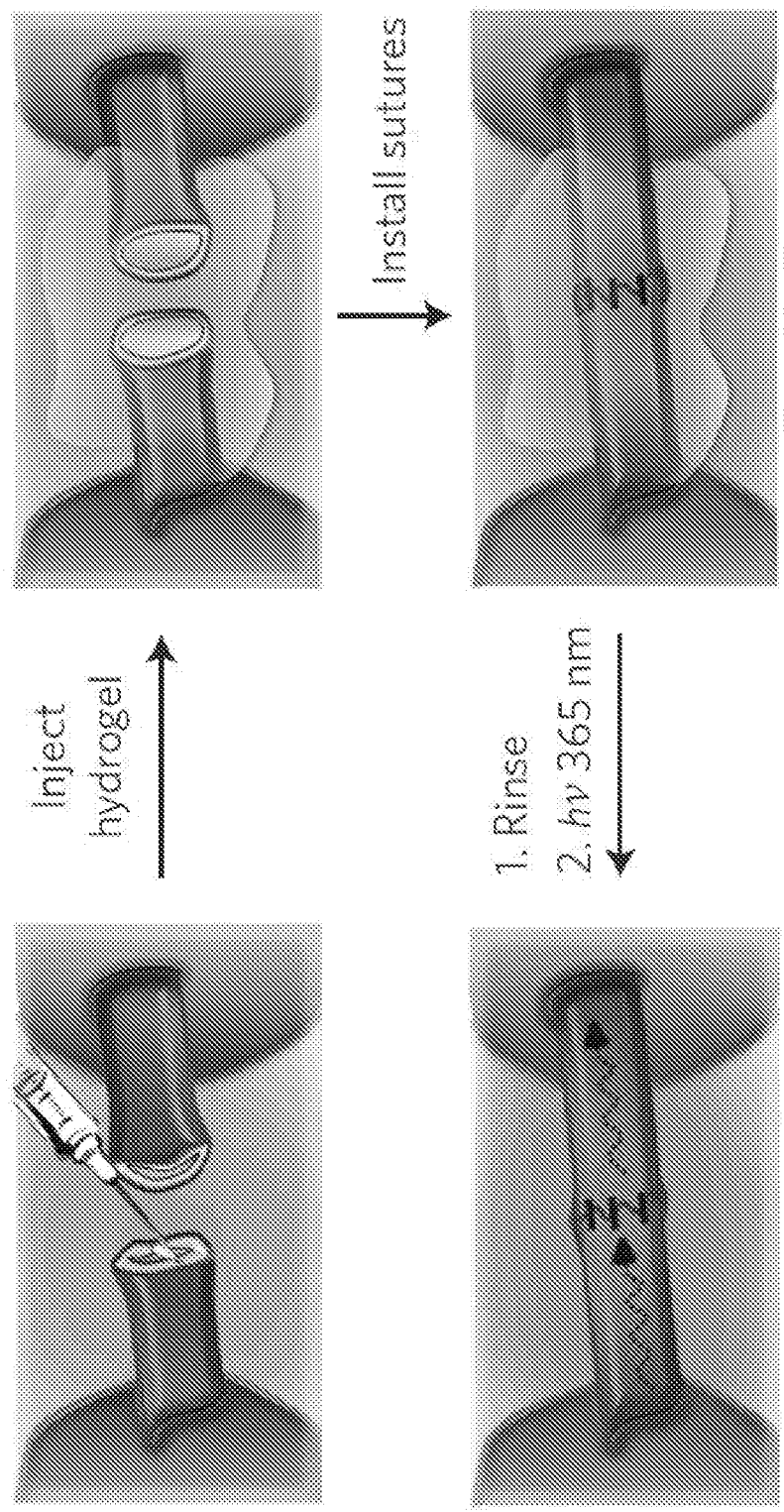
FIG. 1 illustrates a method of anastomosis using a disclosed peptide hydrogel. The peptide hydrogel is preformed in a syringe, and is injected into the lumen of a severed vessel (top left). Passing the hydrogel through the needle of the syringe provides shear stress that triggers sol-gel phase transition leading to a low viscosity peptide solution. Once past the needle, the shear stress is removed, and the hydrogel reforms (heals) in the lumen of the collapsed vessel, resulting in vascular distention (top right). The gel can also be applied to the interspace between vessels providing a medium to approximate the vessels. The vascular distension greatly facilitates suturing of the ends of the severed vessel (lower right). Finally, UV photolysis triggers the final gel-sol transition to allow blood flow (lower left).

The disclosed hydrogels circumvent the limitations of both conventional and current degradable stents and are surprisingly effective in anastomosis procedures. The disclosed peptides form a n-hairpin conformation that self assembles and undergoes a sol-gel phase transition under physiological conditions to form a rigid, self-supporting hydrogel directly in a syringe. The resulting solid-like hydrogel is characterized by shear-thin/recovery rheological properties. Shear-thinning converts the solid-like gel into a viscous gel capable of flow. Cessation of shear stress results in gel recovery. This property allows the gel to be delivered by syringe directly to the collapsed lumen of vessels where it re-establishes vessel shape, greatly aiding the suturing of the vessel. The disclosed hydrogels not only distend the vasculature, which facilitates easier identification of a single vessel wall through which a suture can be placed, but helps maintain a cylindrical vessel shape, to lead to more uniform suture spacing and vessel closure. An unexpected benefit of the gel is that it can be applied external to the severed vessel ends to aid their approximation. Vessel ends can be inserted into the gel, where local thinning occurs proximal to the vessels during their movement within the gel. Once the vessels are approximated, the gel instantaneously recovers, gently fixing them. This allows optimal placement of the vessel ends for suture placement without the fixation clamps. Insertion of vessel ends into the gel, their physical movement and final gentle fixation, as well as suturing directly through the gel, is possible as a consequence of the shear-thin/recovery property of the gel.

On completion of suturing, external gel can be washed away with saline and the initiation of the final gel-sol transition that facilitates the material's removal from within the vessel is enabled by the incorporation of a photocage glutamic acid (for example, 4-methoxy-7-nitroindolinyl glutamic acid [E(MNI)]), into the primary peptide sequence. The photocaged glutamic acid has a neutral charge and projects from the peptide backbone on the hydrophobic face of the peptide β-hairpin. Irradiation of the material with light (e.g. 365 nm light) de-cages the photocaged glutamate, exposing the negative charge of the glutamate on the hydrophobic face of the β-hairpin. This destabilizes the self-assembled fibril network that defines the gel and triggers the final gel-sol transition, which allows a resumption of blood flow that disperses the disrupted hydrogel from the anastomosed vessel.

In one embodiment, the hydrogel includes the peptide APC1, which is a twenty residue peptide having the following sequence: Ac-VKVKVKGKV$^D$PPTKZEVKVKV-NH2; where Z is a photocaged glutamic acid, namely 4-methoxy-7-nitroindolinyl glutamic acid [E(MNI)] and $^D$P is a proline having D-stereochemistry at its C-alpha carbon.

A. Summary of Terms

Unless otherwise noted, technical terms are used according to conventional usage. As used herein, the singular forms "a," "an," and "the," refer to both the singular as well as plural, unless the context clearly indicates otherwise. For example, the term "a peptide" includes single or plural peptides and can be considered equivalent to the phrase "at least one peptide." As used herein, the term "comprises" means "includes." Thus, "comprising a peptide" means "including peptide" without excluding other elements. It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

Anastomosis: A surgical connection between two luminal structures, for example an end-to-end suturing of tubular structures such as blood vessels, lymphatic vessels, or ducts. Vascular anastomosis is the surgical joining of two blood vessels (e.g., arteries or veins), such as the joining of two opposing ends of a severed artery or vein. Ducts are anatomic tubular structures with well-defined walls that often serve to convey excretions or secretions within the body. Examples include the bile duct, pancreatic duct, and nasolacrimal duct.

Amphiphilic β-hairpin conformation: A structural conformation of a peptide or protein. The β-hairpin conformation includes two β-strands linked by a β-turn to form a "hairpin"-like shape. The structure is amphiphilic; thus, one face of the hairpin is primarily hydrophobic, and the other is primarily hydrophilic. A limited number of the side chains of hydrophobic amino acids can exist on the hydrophilic face of the hairpin and vice versa, but not so many as to change the overall amphiphilicity of the folded structure. A non-limiting example of a peptide that can fold into an amphiphilic β-hairpin conformation is provided herein as APC1.

Isolated: An "isolated" biological component (such as a nucleic acid molecule, or peptide) that has been substantially separated or purified away from other biological components in the tissue or cell of the organism in which the component naturally occurs, or from contaminants or other by-products generated when a nucleic acid molecule or peptide is generate synthetically. Nucleic acids and peptides that have been "isolated" include nucleic acids and proteins purified by standard purification methods. The term also embraces nucleic acids and peptides prepared by recombinant expression in a host cell as well as chemically synthesized nucleic acids and peptides.

Peptide: A chain of amino acids, typically less than 75 amino acids in length, such as 10-50 or 20-50 amino acids in length. The residues in a peptide can include post-translational or secondary modifications, such as glycosylation, sulfation or phosphorylation, as well as chemical modifications, such as attachment of a photocage. "Peptide" applies to naturally occurring amino acid polymers and non-naturally occurring amino acid polymers, including amino acid polymers in which one or more amino acid residues are non-natural amino acids. A "residue" refers to an amino acid or amino acid mimetic incorporated in a peptide by an amide bond or amide bond mimetic. A peptide has an amino terminal (N-terminal) end and a carboxy terminal (C-terminal) end.

Typically, the amino acids making up a peptide are numbered in order, starting at the amino terminus and increasing in the direction toward the carboxy terminus of the peptide. Thus, when one amino acid is said to "follow" another, that amino acid is positioned closer to the carboxy terminal end of the peptide than the preceding amino acid.

Peptide hydrogel: A colloid gel including an internal phase and a dispersion medium, in which an aqueous solution is the dispersion medium and a self-assembled network of peptides is the internal phase. The peptides in the hydrogel fold into an amphiphilic β-hairpin conformation and self-assemble into a fibrillar network that forms the internal phase of the hydrogel. Peptide hydrogels include a sufficient elastic modulus or stiffness that allows them to maintain shape. In several embodiments, the peptide hydrogel has an elastic modulus of 40 Pascal or greater. Peptide hydrogels formed from self-assembled peptides in an amphiphilic β-hairpin conformation can be characterized by shear-thin/recovery rheological properties. Thus, application of shear stress converts the solid-like gel into a viscous gel capable of flow, and cessation of the shear results in gel recovery. General information concerning peptide hydrogels having shear-thin/recovery rheological properties and methods of making same are known in the art (see, e.g., Sathaye, et al. Biomacromolecules, 2014, 15(11):3891-3900; Hule et al., 2008, Faraday Discuss, 139:251-420). In several embodiments, the peptide hydrogel can be a sterile hydrogel prepared with physiological and non-toxic dispersion medium for use in an anastomosis procedure on a subject.

Photocaged amino acid: An amino acid whose side chain has been "caged" with a photo-labile moiety that alters a characteristic of the side chain, for example, the charge or size of the side chain. A "caged" amino acid is one in which a biological activity or structural characteristic is blocked by the generally covalent attachment of a protecting group onto a key functional group of the molecule. The strategy has been used to cage various biomolecules such as a peptide, protein, or nucleic acid. The photo-labile moiety can be removed (or uncaged or decaged) from the side chain of the amino acid by selectively irradiating the amino acid with a sufficient amount of light at an appropriate wavelength (e.g., ultraviolet light). The person of ordinary skill in the art is familiar with photocaged amino acids, and methods of making and uncaging same. In several embodiments, a disclosed peptide includes a photocaged glutamate residue, such as a 4-methoxy-7-nitroindolinyl-glutamate residue.

Polypeptide modifications: The present disclosure includes mutant peptides, as well as synthetic embodiments. In addition, analogues (non-peptide organic molecules), derivatives (chemically functionalized polypeptide molecules obtained starting with the disclosed polypeptide sequences) and variants (homologs) of polypeptides can be utilized in the methods described herein. The polypeptides disclosed herein include a sequence of amino acids that can include L- and/or D-amino acids, naturally occurring and otherwise.

Peptides can be modified by a variety of chemical techniques to produce derivatives having essentially the same activity as the unmodified polypeptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring Amino groups of the polypeptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the polypeptide side chains can be converted to $C_1$-$C_{16}$ alkoxy or to a $C_1$-$C_{16}$ ester using well-recognized techniques. Phenyl and phenolic rings of the polypeptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the polypeptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the polypeptides of this disclosure to select and provide conformational constraints to the structure that result in enhanced stability. For example, a C- or N-terminal cysteine can be added to the polypeptide, so that when oxidized the polypeptide will contain a disulfide bond, generating a cyclic polypeptide. Other polypeptide cyclizing methods include the formation of thioethers and carboxyl- and amino-terminal amides and esters.

Proximal: Refers to the qualitative or quantitative distance between two moieties; for example, the distance between two amino acid side chains of a peptide in an amphiphilic β-hairpin conformation as disclosed herein. In several embodiments, two amino acid sidechains (such as a glycine sidechain (hydrogen) and a photocaged glutamate side chain) of a peptide in an amphiphilic β-hairpin conformation can be proximal when the glycine and glutamate are on opposite β-stands of the n-hairpin and are an equal number of residues from the type-II' β-turn of the hairpin. Thus, when the APC1 peptide is in an amphiphilic β-hairpin conformation, the side chain of the glycine at position 7 is proximal to the sidechain of the photocaged glutamate at position 14.

Subject: Living multi-cellular vertebrate organisms, a category that includes human and non-human mammals. In one example, a subject is a human. In an additional example, a subject is selected that is in need of vascular or ductal anastomosis.

Pharmaceutical composition: A composition including an amount of a disclosed peptide together with one or more non-toxic pharmaceutically acceptable additives, including carriers, diluents, preservatives and optionally other biologically active ingredients (such as anti-inflammatory, anti-bacterial, or anti-viral agents). Such pharmaceutical compositions can be prepared by standard pharmaceutical formulation techniques such as those disclosed in Remington's Pharmaceutical Sciences, Mack Publishing Co., Easton, Pa. (19th Edition).

B. Peptides and Peptide Hydrogels

The disclosure provides peptides that, under appropriate conditions (e.g., 2.0% w/v peptide in 50 mM Bis Tris Propane, pH 7.4, 150 mM NaCl, at 25° C.), can fold into an amphiphilic β-hairpin conformation comprising a β-turn, two β-strands, a hydrophobic face, and a hydrophilic face. Under the appropriate conditions, the folded peptides can self-assemble into a fibrillar network and cause a solution containing the network to undergo a sol-gel phase transition to form a hydrogel.

The resultant hydrogel is mechanically rigid and displays shear-thinning/recovery behavior. This characteristic provides a free flowing suspension during the application of shear and complete reformation of the gel network (self-healing) after cessation of the shear. This combination of shear thinning and self-healing allows material formation in a spatially resolved manner. For example, in some embodiments, one of ordinary skill in the art can inject (shear thin) a pre-formed hydrogel into a lumen of a vessel where it self heals and provides support to maintain the vessel in an open configuration. The shear stress converts the gel to a lower viscosity, flowable fluid. The shear stress is relieved when the fluid exits the syringe and the gel quickly self-heals, recovering its original mechanical rigidity. This shear-thinning/recovery mechanism allows the hydrogel to be easily delivered by syringe to effectively match the shape of the target site.

Figure 2:
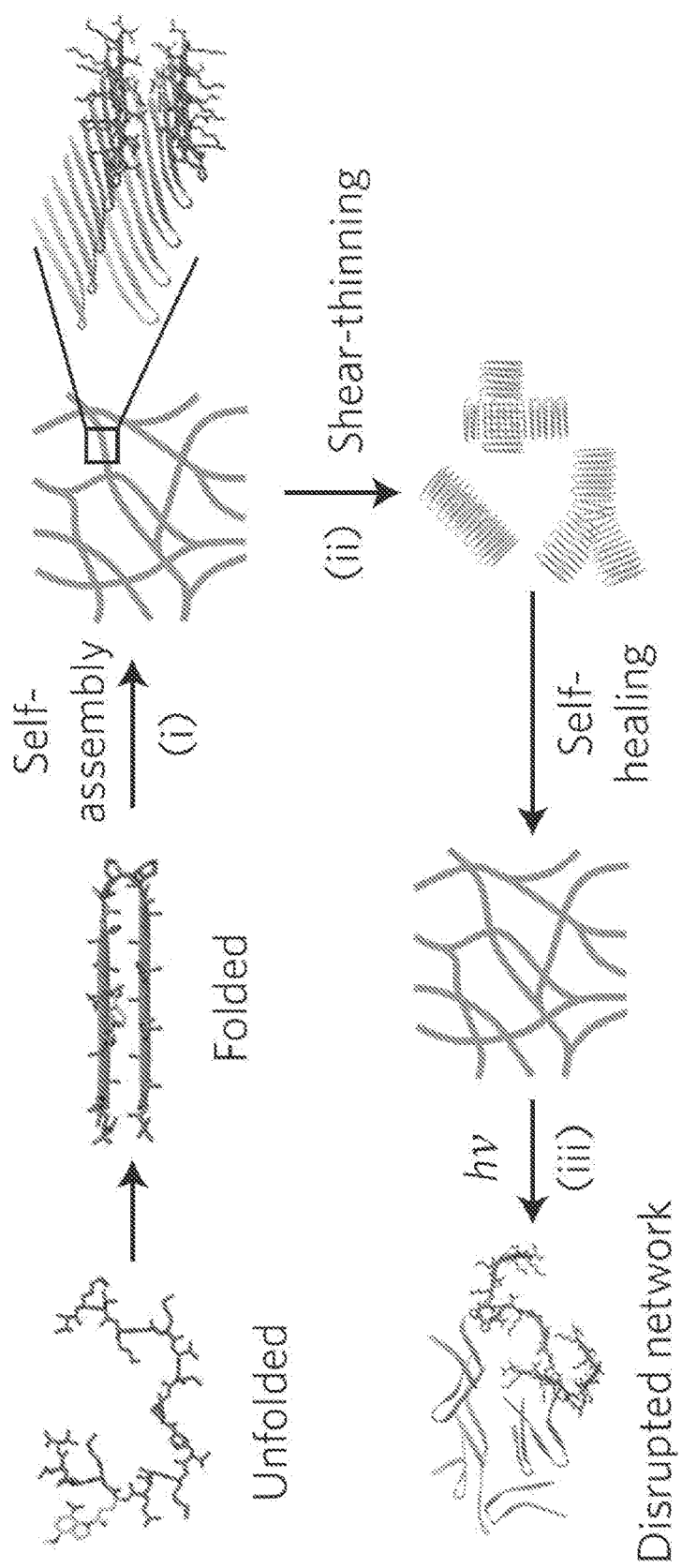
FIG. 2 illustrates the multiple gel-sol phase transitions of a peptide hydrogel based on the APC1 peptide. (i) Triggered peptide folding and self-assembly leads to the formation of a fibrillar hydrogel network. The side and top sides of the peptide in the β-hairpin conformation are shown, with the hydrophobic and hydrophilic faces of the peptide indicated. (ii) Shear-thinning converts the solid-like gel to a viscous gel capable of flow. Cessation of applied shear allows gel recovery. (iii) Irradiation with UV destabilizes the fibril network and triggers the final gel-sol phase transition to a viscous gel capable of flow.

As illustrated in FIGS. 2 and 3, the β-strand regions of the hairpin contain alternating sequences of hydrophobic (e.g., valine, glycine, or a glutamate shielded with a neutral photocage) and hydrophilic (charged) residues (e.g., lysine) such that in the folded state, one face (e.g., the valine-rich face) of the peptide is hydrophobic and the opposing face (e.g., the lysine face) is lined with positively charged side chains and is hydrophilic. This amphiphilic arrangement facilitates inter-molecular peptide interactions, and the fibril arrangement necessary for hydrogel formation.

The peptides in the hydrogel comprise photo-caged glutamate residues with a neutral photocage that can be photolytically selectively uncaged. Uncaging the glutamate residue disrupts the fibrillar network and triggers an irreversible gel-sol phase transition of the hydrogel.

In several embodiments, the amphiphilic β-hairpin conformation of the peptide comprises a β-turn, a first β-strand, a second β-strand, a hydrophobic face, and a hydrophilic face. The first β-strand comprises the photocaged glutamate residue, the second β-strand comprises a glycine residue, and the sidechains of the photocaged glutamate residue and the glycine residue are proximal to each other on the hydrophobic faces of the peptides. The neutral charge of the photocage masks the negative charge of the glutamate residue, preventing the negative charge from disrupting assembly of the peptides in the fibrillar network of the hydrogel, via interactions between the hydrophobic faces of the peptides. Selectively uncaging the photocaged glutamate residues disrupts the interactions between the hydrophobic faces of the peptides by exposing the negative charges of the glutamate residues, thereby disrupting the fibrillar network and triggering the irreversible gel-sol phase transition of the hydrogel.

In the self-assembled state, the glycine residue on the peptide provides a hole on the hydrophobic face of one folded hairpin into which the caged side chain from a neighboring hairpin in the fibril can reside. This 'lock and key' side chain packing arrangement accommodates the large photocage within the tight steric constraints of the bilayer interior. This arrangement results in a well-packed hydrophobic face that is conducive to hairpin bilayer formation (FIG. 3C) to facilitate the self-assembly mechanism leading to the formation of fibrils and ultimate sol-gel phase transition. Removal (uncaging) of the photocage exposes the negative charge of the glutamate to the hydrophobic face of the β-hairpin structure, leading to global disruption of the hydrogel's fibril network.

After intramolecular folding, subsequent self-assembly of monomeric hairpins is facilitated facially by hydrophobic association of the hydrophobic faces of folded hairpins and laterally via H-bond formation and hydrophobic van der Waals contacts between neighboring hairpins. Detailed knowledge of these parameters allows one to control the self-assembly process and thus the ultimate hydrogel material properties. For example, under folding conditions peptides may adopt a desired secondary structure (e.g., may adopt an amphiphilic β-hairpin structure where one face of each β-strand in the hairpin is lined with hydrophobic residues and the other face is lined with hydrophilic residues). For example, intramolecular folding is dictated by the alleviation of charge density on the hydrophilic face upon folding, the formation of intramolecular hydrophobic van der Waals interactions, the formation of intramolecular hydrogen bonds between β-strands within the hairpin, and the turn propensity of the β-turn sequence included in the peptide, see, e.g., FIGS. 2 and 3.

Thus, peptides for use in the disclosed hydrogels can be constructed to have desired characteristics by varying one or more of at least the following parameters: 1) electrostatics, for example, by varying the charge within the peptide intramolecular folding and self-assembly rates can be varied; 2) Van der Waals interactions, for example, constructing peptides having varying a) lateral and facial intermolecular hydrophobic interactions and/or b) intramolecular hydrophobic interactions, allows varying the folding and self-assembly of the peptides as well as the material properties of the hydrogel; 3) hydrogen bonding, for example peptides may be constructed with varying a) intramolecular and/or b) intermolecular hydrogen bond formation to vary the folding, self-assembly and final material properties; 4) turn sequence, for example, the turn region of peptides of the invention may be designed to control folding and thus trigger self-assembly; and 5) the positioning of the photocaged glutamate residue and corresponding glycine residue in the peptide.

In several embodiments, the disclosed peptide may include high β-sheet propensity residues flanking an intermittent four residue turn sequence. Polar and apolar residues may be arranged sequentially in the strand regions to afford amphiphilic surfaces when the peptide is folded in a β-hairpin conformation. For the four residue turn sequence, the peptide typically includes four residues (termed i, i+1, i+2, and i+3) that form a type II' beta turn. In the disclosed APC1 and APC2 peptides, these four residues are $V^DPPT$, and the type II' beta turn is defined by the dihedral angles (Phi and Psi) adopted by the $^DPP$ portion of the turn sequence, where '$^D$' denotes D-stereochemistry of the first proline residue. The preferred Phi and Psi dihedral angles (degrees) that define a type II' turn are: residue i+1 (60,−120); residue i+2 (−80, 0). However, these values can vary by +/−20 degrees and the peptide can still form the appropriate β-turn structure In one particular embodiment, APC1, a 20-residue peptide is composed of high β-sheet propensity valine and lysine residues flanking an intermittent tetrapeptide—$V^DPPT$— designed to adopt type-II' β-turn structure, and includes a photocaged glutamate residue positioned opposite to a glycine residue when the peptide is an amphiphilic β-hairpin conformation, FIG. 3. In addition to incorporating local design elements to stabilize hairpin structure, nonlocal effects were also considered by arranging the polar and apolar residues flanking the β-turn in an alternating fashion to favor β-hairpin formation in the self-assembled state. In addition, a β-branched residue was placed at the i-position of the turn to enforce a trans prolyl amide bond geometry at the i+1 position. This design element ensures that under folding conditions, intramolecular folding of monomeric hairpins is favored prior to self-assembly. A cis prolyl bond, which is designed against, could result in the presentation of individual β-strands within each monomer in an extended conformation. Peptides capable of adopting both cis and trans conformers could undergo indiscriminant self-association of extended and correctly folded monomers and may be actively designed against. Additionally, as illustrated in FIG. 3, the photocaged glutamate and the glycine residue included in APC1 are equidistant from the $^D$PP β-turn residues, so that they are opposite to each other when the peptide folds into a β-hairpin conformation. This arrangement allows the intermolecular packaging of the neutral photocage into the cavity created by the glycine residue of a neighboring hairpin present in the self-assembled fibrillar state.

In non-limiting examples, the peptide can comprise or consist of a peptide selected from one of

APC1
VKVKVKGKV$^D$PPTKZEVKVKV;

APC1a
VKVKVKZKV$^D$PPTKGEVKVKV;

APC2
VKVKGKVKV$^D$PPTKVEZKVKV;

APC2a
VKVKZKVKV$^D$PPTKVEGKVKV;

APC3
VKVKVKVKG$^D$PPZKVEVKVKV;

APC3a
VKVKVKVKZ$^D$PPGKVEVKVKV;

APC4
VKGKVKVKV$^D$PPTKVEVKZKV;

APC4a
VKZKVKVKV$^D$PPTKVEVKGKV;

APC5
GKVKVKVKV$^D$PPTKVEVKVKZ;

APC5a
ZKVKVKVKV$^D$PPTKVEVKVKG;

APC6
VKVKVKVKG$^D$PPZKVKVKVKV;

APC6a
VKVKVKVKZ$^D$PPGKVKVKVKV;

APC7
VKVKVKGKV$^D$PPTKZKVKVKV;

APC7a
VKVKVKZKV$^D$PPTKGKVKVKV;

APC8
VKVKGKVKV$^D$PPTKVKZKVKV;

APC8a
VKVKZKVKV$^D$PPTKVKGKVKV;

APC9
VKGKVKVKV$^D$PPTKVKVKZKV;

APC9a
VKZKVKVKV$^D$PPTKVKVKGKV;

APC10
GKVKVKVKV$^D$PPTKVKVKVKZ;

APC10a
ZKVKVKVKV$^D$PPTKVKVKVKG;

APC11
VKVKVKGKV$^D$PPTKZKTKVKV;

APC11a
VKVKVKZKV$^D$PPTKGKTKVKV;

APC12
KVKVKVGVK$^D$PPSVZVKVKVK;

APC12a
KVKVKVZVK$^D$PPSVGVKVKVK;

APC13
VKVKVKGKV$^D$PPTKZKCKVKV;

APC13a
VKVKVKZKV$^D$PPTKGKCKVKV;

APC14
VKVKVKGKV$^D$PGTKZKVKVKV;

APC14a
VKVKVKZKV$^D$PGTKGKVKVKV;

APC15
VKVKVKGKVP$^D$PTKZKVKVKV;

APC15a
VKVKVKZKVP$^D$PTKGKVKVKV;

APC16
VKVKCKGKV$^D$PPTKZCVKVKV;

APC16a
VKVKCKZKV$^D$PPTKGCVKVKV;

APC17
ISINYRGEI$^D$PPTSZNYRTEI;

APC17a
ISINYRZEI$^D$PPTSGNYRTEI;

APC18
VKVKVCGKV$^D$PPTCZKVKVKV;

APC18a
VKVKVCZKV$^D$PPTCGKVKVKV;

APC19
VEVEVEGEV$^D$PPTEZEVEVEV;

APC19a
VEVEVEZEV$^D$PPTEGEVEVEV;

APC20
VRVRVRGRV$^D$PPTRZRVRVRV;

APC20a
VRVRVRZRV$^D$PPTRGRVRVRV;

APC21
FKFKFKGKV$^D$PPTKZKFKFKF;

APC21a
FKFKFKZKV$^D$PPTKGKFKFKF;

APC22
IKIKIKGKV$^D$PPTKZKIKIKI;

APC22a
IKIKIKZKV$^D$PPTKGKIKIKI;

APC23
HWSFTIKGTV$^D$PPTHZSFTIKIT;
or

APC23a
HWSFTIKZTV$^D$PPTHGSFTIKIT, wherein Z is a photocaged glutamate residue having a photocage with a neutral charge (such as 4-methoxy-7-nitroindolinyl glutamate), and $^D$P refers to a proline that is a D amino acid.

In additional embodiments, the peptide can comprise or consist of APCC1:
XBXBXBXBX$^D$PPXBXBXBXBX, wherein each X is independently selected from V, L, I, A, F, T, W, or Y; and each B is independently selected from any residue except proline, except that one of position pairs 1 and 20, 3 and 18, 5 and 16, 7 and 14, or 9 and 12 is G and Z, or Z and G, respectively, wherein Z is a photocaged glutamate residue with a neutral photocage (such as 4-methoxy-7-nitroindolinyl glutamate), and wherein $^D$P refers to a proline that is a D amino acid and the peptide is in an amphiphilic β-hairpin conformation when dissolved at 2.0% w/v in 50 mM Bis Tris Propane, pH 7.4, 150 mM NaCl, at 25° C.

In additional embodiments, the peptide can comprise or consist of APCC2:
(BX)$_m$ $^D$PP (XB)$_n$, wherein each X is independently selected from V, L, I, A, F, T, W, or Y; and each B is independently selected from any residue except proline, except that at least one (such as one) pair of X's equidistant from $^D$PP comprises G and Z, or Z and G, respectively wherein Z is a photocaged glutamate residue with a neutral photocage (such as 4-methoxy-7-nitroindolinyl glutamate), and wherein $^D$P refers to a proline that is a D amino acid and the peptide is in an amphiphilic β-hairpin conformation when dissolved at 2.0% w/v in 50 mM Bis Tris Propane, pH 7.4, 150 mM NaCl, at 25° C.

In additional embodiments, the peptide can comprise or consist of APCC3:
(XB)$_m$ X$^D$PPX (BX)$_n$, wherein each X is independently selected from V, L, I, A, F, T, W, or Y; and each B is independently selected from any residue except proline, except that at least one (such as one) pair of X's equidistant from $^D$PP comprises G and Z, or Z and G, respectively wherein Z is a photocaged glutamate residue with a neutral photocage (such as 4-methoxy-7-nitroindolinyl glutamate), and wherein $^D$P refers to a proline that is a D amino acid and the peptide is in an amphiphilic β-hairpin conformation when dissolved at 2.0% w/v in 50 mM Bis Tris Propane, pH 7.4, 150 mM NaCl, at 25° C. In several embodiments, m and n independently can be from 1-100, such as from 10-20.

In additional embodiments, the peptide can comprise or consist of a peptide selected from one of:

APCC4
XBXBXBXBG$^D$PPZBXBXBXBX;

APCC4a
XBXBXBXBZ$^D$PPGBXBXBXBX;

APCC5
XBXBXBGBX$^D$PPXBZBXBXBX;

APCC5a
XBXBXBZBX$^D$PPXBGBXBXBX;

APCC6
XBXBGBXBX$^D$PPXBXBZBXBX;

APCC6a
XBXBZBXBX$^D$PPXBXBGBXBX;

APCC7
XBGBXBXBX$^D$PPXBXBXBZBX;

APCC7a
XBZBXBXBX$^D$PPXBXBXBGBX;

APCC8
GBXBXBXBX$^D$PPXBXBXBXBZ;
or

APCC8a
ZBXBXBXBX$^D$PPXBXBXBXBG, wherein each X is independently selected from V, L, I, A, F, T, W, or Y; and each B is independently selected from any residue except proline, and wherein Z is a photocaged glutamate residue with a neutral photocage (such as 4-methoxy-7-nitroindolinyl glutamate), and wherein $^D$P refers to a proline that is a D amino acid and the peptide is in an amphiphilic β-hairpin conformation when dissolved at 2.0% w/v in 50 mM Bis Tris Propane, pH 7.4, 150 mM NaCl, at 25° C. In some embodiments, the peptide can comprise or consist of a peptide selected from one of:

APCC4
XBXBXBXBG$^D$PPZBXBXBXBX;

APCC4a
XBXBXBXBZ$^D$PPGBXBXBXBX;

APCC5
XBXBXBGBX$^D$PPXBZBXBXBX;

APCC5a
XBXBXBZBX$^D$PPXBGBXBXBX;

APCC6
XBXBGBXBX$^D$PPXBXBZBXBX;

APCC6a
XBXBZBXBX$^D$PPXBXBGBXBX;

APCC7
XBGBXBXBX$^D$PPXBXBXBZBX;

APCC7a
XBZBXBXBX$^D$PPXBXBXBGBX;

APCC8
GBXBXBXBX$^D$PPXBXBXBXBZ;
or

APCC8a
ZBXBXBXBX$^D$PPXBXBXBXBG, wherein each X is independently selected from V, L, I, A, F, T, W, or Y; and each B is independently selected from any residue except proline, and wherein Z is a photocaged glutamate residue with a neutral photocage (such as 4-methoxy-7-nitroindolinyl glutamate), and wherein $^D$P refers to a proline that is a D amino acid and the peptide is in an amphiphilic β-hairpin conformation when dissolved at 2.0% w/v in 50 mM Bis Tris Propane, pH 7.4, 150 mM NaCl, at 25° C., and wherein the peptide comprises an E at position 15.

In some embodiments, the peptide can comprise or consist of APCC5:
XBXBXBGBX$^D$PPXBZBXBXBX, wherein each X is independently selected from V, L, I, A, F, T, W, or Y (such as V); and each B is independently selected from any residue except proline (such as K), and wherein Z is a photocaged glutamate residue with a neutral photocage (such as 4-methoxy-7-nitroindolinyl glutamate), and wherein $^D$P refers to a proline that is a D amino acid and the peptide is in an amphiphilic β-hairpin conformation when dissolved at 2.0% w/v in 50 mM Bis Tris Propane, pH 7.4, 150 mM NaCl, at 25° C.

In some embodiments, the peptide can comprise or consist of APCC5a: XBXBXBZBX$^D$PPXBGBXBXBX, wherein each X is independently selected from V, L, I, A, F, T, W, or Y (such as V); and each B is independently selected from any residue except proline (such as K), and wherein Z is a photocaged glutamate residue with a neutral photocage (such as 4-methoxy-7-nitroindolinyl glutamate), and wherein $^D$P refers to a proline that is a D amino acid and the peptide is in an amphiphilic β-hairpin conformation when dissolved at 2.0% w/v in 50 mM Bis Tris Propane, pH 7.4, 150 mM NaCl, at 25° C.

In some embodiments, the peptide can comprise or consist of APCC5: XBXBXBGBX$^D$PPXBZBXBXBX, wherein each X is independently selected from V, L, I, A, F, T, W, or Y (such as V); and each B is independently selected from any residue except proline (such as K), and wherein Z is a photocaged glutamate residue with a neutral photocage (such as 4-methoxy-7-nitroindolinyl glutamate), and wherein $^D$P refers to a proline that is a D amino acid and the peptide is in an amphiphilic β-hairpin conformation when dissolved at 2.0% w/v in 50 mM Bis Tris Propane, pH 7.4, 150 mM NaCl, at 25° C., and wherein the peptide comprises an E at position 15.

In some embodiments, the peptide can comprise or consist of APCC5a: XBXBXBZBX$^D$PPXBGBXBXBX, wherein each X is independently selected from V, L, I, A, F, T, W, or Y (such as V); and each B is independently selected from any residue except proline (such as K), and wherein Z is a photocaged glutamate residue with a neutral photocage (such as 4-methoxy-7-nitroindolinyl glutamate), and wherein $^D$P refers to a proline that is a D amino acid and the peptide is in an amphiphilic β-hairpin conformation when dissolved at 2.0% w/v in 50 mM Bis Tris Propane, pH 7.4, 150 mM NaCl, at 25° C., and wherein the peptide comprises an E at position 15.

Peptides for use in the disclosed embodiments can be peptides from about 10 to about 75 residues (e.g., from about 10 to about 50 residues, from about 10 to about 40 residues, from about 10 to about 30 residues, from about 10 to about 25 residues, from about 10 to about 20 residues, from about 15 to about 75 residues, from about 15 to about 50 residues, from about 15 to about 40 residues, from about 15 to about 30 residues, from about 15 to about 25 residues, from about 15 to about 20 residues, from about 20 to about 75 residues, from about 20 to about 50 residues, from about 20 to about 40 residues, from about 20 to about 30 residues, or from about 20 to about 25 residues; "about" refers to plus or minus 2 residues). In some embodiments, the peptides for use in the disclosed embodiments can be from 10 to 75 residues (e.g., from 10 to 50 residues, from 10 to 40 residues, from 10 to 30 residues, from 10 to 25 residues, from 10 to 20 residues, from 15 to 75 residues, from 15 to 50 residues, from 15 to 40 residues, from 15 to 30 residues, from 15 to 25 residues, from 15 to 20 residues, from 20 to 75 residues, from 20 to 50 residues, from 20 to 40 residues, from 20 to 30 residues, or from 20 to 25 residues).

In some embodiments, the peptide can be no more than 50 residues, such as no more than 30 residues or no more than 20 residues. In additional embodiments, the peptide can be 10, 15, 20, 25, 30, 35, 40, 45, or 50, residues in length. In some embodiments, the disclosed peptides can be 18 amino acids in length. In some embodiments, the disclosed peptides can be 20 amino acids in length. In some embodiments, the disclosed peptides can be 22 amino acids in length. In some embodiments, the disclosed peptides can be 24 amino acids in length. In some embodiments, the disclosed peptides can be from 18-22 amino acids in length. In some embodiments, the disclosed peptides can be from 18-26 amino acids in length. In some embodiments, the disclosed peptides can be one of 18, 20, 22, 24, 26, or 28 amino acids in length.

The disclosed peptides include a photocaged glutamate residue. Photo-caging technology is known to the person of ordinary skill in the art (see, e.g., Shao and Xing, *Chem. Soc. Rev.*, 39(8), 2835-2846, 2010). As discussed above, the photocage used in the disclosed embodiments shields the negative change of the glutamate residue, and has a neutral charge that does not interfere with the assembly of the peptides into a fibrillar network in a hydrogel. Non-limiting examples of photocages that can be used to shield the negative charge of the glutamate residue included in the peptide include 4-methoxy-7-nitroindolinyl cages, o-nitrobenzyl cages, p-hydroxyphenacyl cages, modified BODIPY-based cages, and coumarin-based cages.

For example, in APC1, the amino acid residue at position 15 includes a glutamate residue caged with a 4-methoxy-7-nitroindolinyl moiety. A 4-methoxy-7-nitroindolinyl moiety is a commonly used neutral photocage and its selectively induced photolysis has been thoroughly studied.

Exposing caged peptides to light of appropriate preselected wavelength (e.g., 330-360 nm) results in selective release of the neutral cage and exposure of the charged glutamate residue on the hydrophobic face of the amphiphilic β-hairpin peptide.

Appropriate methods for uncaging caged molecules are also known in the art. For example, selected wavelengths of light for removing many photolabile groups have been described (e.g., ~365 nM for 4-methoxy-7-nitroindolinyl). The optimal irradiation wavelength, intensity, and timing parameters for removing a photolabile caging group can be determined according to methods well known in the art. Instrumentation and devices for delivering uncaging light are likewise known; for example, use of a lamp or a laser. In the case of translucent (or partially translucent) vessels, the irradiation used to uncage the glutamate residue can be applied transmurally through the vessel wall. Alternatively (or additionally), the irradiation used to uncage the glutamate residue can be applied endoluminally from within the vessel lumen (for example, using an endoscope including a lamp or laser that emits an appropriate wavelength of light). In embodiments where the hydrogel is applied to the interspace between and around vessel ends, the gel can simply be washed away, with or without decaging the photocaged glutamate. If irradiation is used to uncage the glutamate residue on gel applied to the interspace between and around vessel ends, the irradiation can be simply applied directly to the peptide hydrogel. The intensity of the light applied to uncage the photocaged glutamate can vary depending on the particular application, and is sufficient to cause photolysis of the photocaged glutamate without causing significant damage to the anastomosed vessel or surrounding tissue.

Typically, the period of irradiation maybe from about a second to several minutes, for example, from about 1s to about 5 min, such as about 10s to about 5 min, from about 30s to about 5 min, from about 30s to about 3 min, from about 30s to about 2 min, from about 1 min to about 5 min, from about 1 min to about 3 min, from about 1 min to about 2 min, or about 30s, about 1 min, about 2 min, about 3 min, or about 5 min. Suitable irradiation sources include may provide bulk and/or spatially resolved irradiation and may include, but are not limited to, an OPTI-LUX 365 UV-A LED Flashlight (Spectroline, USA).

The disclosed peptides, and modified versions thereof can be readily synthesized by automated solid phase procedures well known in the art and as described in the examples section below. The disclosed peptides may incorporate one or more modified amino acid residues (e.g., D-amino acids, homologs of naturally occurring amino acids, amino acids with modified side chains, etc.). Techniques and procedures for solid phase synthesis are described in *Solid Phase Peptide Synthesis: A Practical Approach*, by E. Atherton and R. C. Sheppard, published by IRL, Oxford University Press, 1989. Alternatively, apelin-36 (42-57) peptides may be prepared by way of segment condensation, as described, for example, in Liu et al., *Tetrahedron Lett.* 37:933-936, 1996; Baca et al., *J. Am. Chem. Soc.* 117:1881-1887, 1995; Tam et al., *Int. J. Peptide Protein Res.* 45:209-216, 1995; Schnolzer and Kent, *Science* 256:221-225, 1992; Liu and Tam, *J. Am. Chem. Soc.* 116:4149-4153, 1994; Liu and Tam, *Proc. Natl. Acad. Sci. USA* 91:6584-6588, 1994; and Yamashiro and Li, *Int. J. Peptide Protein Res.* 31:322-334, 1988). Other methods useful for synthesizing the apelin-36 (42-57) peptides of the disclosure are described in Nakagawa et al., *J. Am. Chem. Soc.* 107:7087-7092, 1985.

Additional exemplary techniques known to those of ordinary skill in the art of peptide synthesis are taught by Bodanszky, M. and Bodanszky, A., *The Practice of Peptide Synthesis*, Springer Verlag, New York, 1994; and by Jones, J., *Amino Acid and Peptide Synthesis*, 2nd ed., Oxford University Press, 2002. The Bodanszky and Jones references detail the parameters and techniques for activating and coupling amino acids and amino acid derivatives. Moreover, the references teach how to select, use and remove various useful functional and protecting groups. Peptides of the disclosure can also be readily purchased from commercial suppliers of synthetic peptides. Such suppliers include, for example, Advanced ChemTech (Louisville, Ky.), Applied Biosystems (Foster City, Calif.), Anaspec (San Jose, Calif.), and Cell Essentials (Boston, Mass.).

Following synthesis, the disclosed peptides can be purified by many techniques well known in the art, such as reverse phase chromatography, high performance liquid chromatography, ion exchange chromatography, size exclusion chromatography, affinity chromatography, gel electrophoresis, and the like. The actual conditions used to purify a particular peptide, or a modified form thereof, will depend, in part, on synthesis strategy and on factors such as net charge, hydrophobicity, hydrophilicity, and the like, and will be apparent to those of ordinary skill in the art.

The disclosed hydrogels can readily be made by preparing an aqueous solution comprising one or more amphiphilic β-hairpin peptides as disclosed herein and altering one or more characteristics of the solution, wherein a hydrogel is formed. The characteristic altered may be any characteristic that results in formation of a hydrogel upon its alteration. Suitable examples include, but are not limited to, ionic strength, temperature, concentration of a specific ion, and pH. In particular embodiments, the character altered may be the pH of the solution. The disclosed peptides form a hydrogel at a pH of about 7 or higher. Increasing pH and increasing ionic strength both encourage hydrogel formation, and the two effects are roughly additive. Thus, the lower the pH, the higher the salt concentration necessary for hydrogel formation. In some embodiments, the hydrogel can be formed in a container (such as a syringe), for example a closed container.

In some embodiments, altering one or more characteristic of the solution results in a salt concentration of from about 20 mM to about 400 mM, such as about 50 to about 300 mM, about 100 to about 200 mM, or about 150 mM. Any salt may be used, for example, KCl, NaCl, MgCl$_2$, KF, MgSO$_4$, etc. In one embodiment, the salt may be NaCl. In some embodiments, the solution may have a desired pH, for example, a pH of from about 7 to about 9, a pH of from about 7.5 to about 8.5, a pH of from about 7.0 to about 8.0, or a pH of about 7.4, which may stay the same or be changed upon formation of the hydrogel.

In one non-limiting example, the hydrogel is formed in 50 mM Bis Tris Propane (BTP), 150 mM NaCl, pH 7.4. Any buffer system can be used except phosphate based buffer systems, as phosphate buffers are known to precipitate β-hairpin peptides. Accordingly, peptide hydrogels including the disclosed peptides can simply be formed by, for example, adding buffer of appropriate ionic strength to an aqueous solution of unfolded peptide; drawing the resulting solution into a syringe; and allowing it to gel at 25° C. directly in the syringe.

The disclosed hydrogels are well hydrated solid materials and have a stiffness greater than 40 Pascal (Pa), as measured by the storage modulus G' at a strain of 0.2%. Above approximately 40 Pa the material is a self-supporting solid gel material. The stiffness can reach greater than 10,000 Pa at higher peptide concentration. The hydrogels typically contain at least 0.5 wt % peptide in an aqueous medium. For example, the disclosed hydrogel may have varying amounts of solid (peptide) material. For example, hydrogels may be formed comprising a percent by weight of peptide of from about 0.25% w/v to about 4.0% w/v, from about 0.25% w/v to about 3.0% w/v, from about 0.25% w/v to about 2.0% w/v, from about 0.25% w/v to about 1.0% w/v, from about 0.5% w/v to about 4.0% w/v, from about 0.5% w/v to about 3.0% w/v, from about 0.5% w/v to about 2.0% w/v, from about 0.5% w/v to about 1.0% w/v, from about 1.0% w/v to about 4.0% w/v, from about 1.0% w/v to about 3.0% w/v, from about 1.0% w/v to about 2.0% w/v, from about 2.0% w/v to about 4.0% w/v, or from about 2.0% w/v to about 3.0% w/v.

In one aspect, the amount by weight of peptide and the kinetics of gelation may be varied to produce a hydrogel having a desired modulus (stiffness). Hydrogels of the invention may have a modulus from about 40 Pascal (Pa) to about 50,000 Pa, from about 40 Pa to about 25,000 Pa, from about 40 Pa to about 10,000 Pa, from about 40 Pa to about 5,000 Pa, from about 40 Pa to about 1,000 Pa, from about 40 Pa to about 500 Pa, from about 40 Pa to about 100 Pa, from about 100 Pa to about 50,000 Pa, from about 100 Pa to about 25,000 Pa, from about 100 Pa to about 10,000 Pa, from about 100 Pa to about 5,000 Pa, from about 100 Pa to about 2,000 Pa, from about 100 Pa to about 1,000 Pa, from about 100 Pa to about 500 Pa, or from about 100 Pa to about 250 Pa.

C. Methods

Also provided are methods of using the disclosed peptide hydrogels, for example, in an anastomosis procedure. An exemplary embodiment is illustrated by FIG. 1. The peptide hydrogel can be preformed in a syringe, for example, by adding a solution of peptide (e.g., APC1 or APC2) and water to a syringe, followed by buffer and salt to bring the solution to 150 mM salt, pH 7.5. The preformed hydrogel is injected into the lumens of each of the opposing ends of the severed vessel in a subject. Passing the hydrogel through a needle connected to the syringe provides shear stress that triggers a gel-sol phase transition leading to a low viscosity peptide solution. Once past the needle, the shear is removed, and the hydrogel reforms (heals) in the lumen of the collapsed vessel, resulting in vascular distention. The vascular distension maintains the end of the severed vessel (or each end of the opposing vessels) in an open configuration (preventing collapse of the vessel during surgical apposition of the severed ends of the vessel and placement of vascular sutures during the anastomosis procedure) and greatly facilitates securing the ends of the severed vessel to each other, for example by one or more sutures. A sufficient amount of the hydrogel is injected into the lumen of the vessel to stabilize the vessel in an open (not collapsed) configuration, but not so much as to tear or cause significant damage to the vessel.

Furthermore, the hydrogel can be applied to the interspace between the two vessel ends to assist in apposing the two ends, and their stabilization during the anastomosis procedure. Vessel ends can be inserted into the gel, where local thinning occurs proximal to the vessels during their movement within the gel. Once the vessels are approximated as needed, the gel recovers instantaneously, gently fixing them. This allows optimal placement of the vessel ends for suture placement. Additionally, the surgeon can apply sutures directly through the hydrogel (which can be optically clear) due to its shear-thin/recovery rheological properties; local thinning and recovery occurs around the needle during its movement through the gel. Finally, the anastomosed vessel can be selectively irradiated with a sufficient amount of light of a preselected wavelength to uncage the photocaged glutamate on the peptides in the hydrogel residue and trigger a gel-sol phase transition of the hydrogel to a low viscosity gel capable of flow. As discussed above the irradiating light can be supplied endoluminally or transmurally, for example. Blood flow through the vessel can then disperse the gel and restore patency to the vessel.

The disclosed methods can be utilized to anastomose any type of severed vessel (for example, blood vessels, ducts, or lymphatic vessels) of appropriate size, such as vessel having a diameter of from about 50 μM to about 10 mM, such as from about from about 50 μM to about 5 mM, from about 50 μM to about 1 mM, from about 50 μM to about 500 μM, from about 500 μM to about 10 mM, from about 500 μM to about 5 mM, from about 500 μM to about 1 mM, from about 1 mM to about 10 mM, or from about 1 mM to about 5 mM.

EXAMPLES

The following examples are provided to illustrate particular features of certain embodiments, but the scope of the claims should not be limited to those features exemplified.

Example 1

Multiple Phase Transitioning Self-Assembled Peptide Hydrogel for Use in Vascular Anastomosis Reconstructive, cardiac, vascular, and transplant surgeries rely heavily on the anastomosis of small vessels. Traditional suturing techniques have an increased rate of failure as the size of the vessels decrease, most often a result of technical flaws in the surgical procedure. This example illustrates a peptide-based hydrogel system capable of undergoing multiple consecutive phase transitions enabling its use as an injectable temporary intraluminal stent during micro-anastomosis. An example of a peptide to be included in the hydrogel is provided as APC1, a 20-residue peptide designed to undergo a sol-gel phase transition under physiological conditions to form a rigid, self-supporting hydrogel directly in a syringe. The resultant gel demonstrates shear-thin/recovery rheological properties that allow its syringe delivery into the lumen of collapsed severed blood vessels re-establishing their shape and providing mechanical support to facilitate the anastomosis procedure. On completion of suturing, initiation of the critical final gel-sol transition that facilitates the material's removal is enabled by the incorporation of a photocage amino acid, 4-methoxy-7-nitroindolinyl glutamic acid [E(MNI)], into the primary peptide sequence. Irradiation of the material with 365 nm light de-cages the residue and disrupts the hydrogel network allowing the resumption of blood flow. Biophysical and in-vivo experiments show that this responsive hydrogel has the potential to decrease the surgical difficulty associated with anastomosis while increasing vessel patency, adding a new tool to the armamentarium for vascular/microvascular anastomosis.

Overview

The formation of a vascular anastomosis, or the joining of two blood vessels, is a fairly common procedure used by a broad range of surgeons. The classical anastomosis method using manual suturing has seen many technological advances since the introduction of the triangulation method by Carrel (Lawrie G M (1987) *Clinical Cardiology* 10:428-430). New technologies aim to achieve high rates of patency, prevent excessive damage to the vessel wall that may lead to thrombosis or stricture, and to decrease the time it takes to perform the procedure (Werker and Kon M (1997) *Annals of Thoracic Surgery* 63(6, Supplement 1):5122-S127). Most of these criteria can be accomplished by a highly skilled surgeon with relative ease for large vessels. As the vessels to be anastomosed become smaller or less firm, surgeons have increasing rates of failure. This is even more pronounced among those who do not specialize in vascular- or microsurgery. Aids to reduce failures and facilitate the surgical procedure are highly valuable with tremendous impact on patient care and outcomes.

In general, anastomotic failures often arise from the technical difficulty of suturing small vessels, which require very precise surgical techniques under magnification. Severed vessels tend to contract and have collapsed ends, making their suturing difficult (Hedberg (1962) *Annals of Surgery* 155(1):51). Adding stitches to the collapsed end of a vessel greatly increases the chance of catching the opposing vessel wall, causing excess damage and decreasing the patency of the anastomosed vessel (Smith (1966) *Plastic Reconstructive Surgery* 37(3):227). Early mechanical devices such as expandable stents (Rancic, et al. (2013) *European J Vascular Endovascular Surgery* 45(5):481-487) and stapling tools (Werker and Kon M (1997) *Annals of Thoracic Surgery* 63(6, Supplement 1):5122-5127) were developed to aid in the approximation of the fully opened, tube-like ends of blood vessels in order facilitate the anastomosis. The disadvantages to using these early instruments is that they are generally made of metal, often contain vessel-damaging "spikes" to hold them in place (Abou-Taam, et al. (2013) *Annals of Vascular Surgery* 27(5):638-645), cannot be removed after the surgery (Erdmann, et al. (2004) *J Vascular Surgery* 40(3):505-511), and are only applicable to certain types of anastomosis (Liu, et al. (2006) *Annals of Thoracic Surgery* 82(1):303-306).

The more recent introduction of degradable stents and tissue adhesives has provided attractive alternatives to classic suturing methods. Degradable intraluminal stents or splints have been reported and have the advantage of being biocompatible and much more easily fabricated to match the size of the vessel. Gelatin—(Figlio and Ballinger. (1963) *Transactions American Society for Artificial Internal Organs* 9:321), glyceride—(He, et al. (1999) *Microsurgery* 19(3):148-152), or polymer-based (Chang, et al. (2011) *Nature Medicine* 17(9):1147-U1160) materials as well as biomolecules such as albumin (McCargar, et al. (2012) *Lasers in Surgery and Medicine* 44(4):330-338) and chitosan (Wang, et al. (2005) *Asbm6: Advanced Biomaterials Vi* 288-289:575-578, Lauto, et al. (2001) *Biomaterials* 22(13): 1869-1874) can be used in the construction of tubular or rod-like stents to distend the vessel walls during the surgical procedure. After the anastomosis, these materials can be eliminated from the vessel by either inducing an active temperature-dependent gel-sol phase transition or rely on dissolution of the material by blood. While these materials do facilitate the suturing procedure, their utility is diminished by the requirement for careful control of temperature and/or the long dissolution times required for their removal.

This example describes a self-assembling peptide whose initial sol-gel transition can be directly triggered in a syringe. The resulting solid-like hydrogel is characterized by shear-thin/recovery rheological properties. Shear-thinning converts the solid-like gel into a viscous gel capable of flow. Cessation of shear stress results in gel recovery. This property allows the gel to be delivered by syringe to the collapsed lumen of vessels where it re-establishes vessel shape, greatly aiding the suturing of the vessel (FIG. 1). After the anastomosis procedure is complete, the gel can be dissolved within the vessel by initiating its final gel-sol phase transition by irradiation with light.

Results and Discussion

Peptide Hydrogel Design. The peptide, anastomosis photocaged 1 (APC1), is a twenty-residue peptide designed to undergo triggered folding into a β-hairpin conformation that rapidly self-assembles into a β-sheet rich fibril hydrogel network (FIG. 2, transition i). The primary sequence of APC1 (FIG. 3A) contains seven lysine residues that are protonated at neutral pH. When the peptide is dissolved in water these charges keep the peptide soluble and in its monomeric unfolded state due to inter-residue electrostatic repulsion. A sol-gel phase transition can be triggered by increasing the ionic strength of the solution and heating to 25° C. Increasing the ionic strength screens the lysine-borne charge of the peptide, and increasing the solution temperature facilitates the desolvation of hydrophobic residues. In concert, these two effects trigger the folding and assembly of the peptide. In its folded state, APC1 is designed to adopt an amphiphilic β-hairpin comprised of two β-strands of alternating hydrophobic and hydrophilic residues connected by a four residue type II', β-turn sequence (-V$^D$PPT-) (Nair, et al. (1979) *J Chemical Society-Chemical Communications* (24): 1183-1184). The alternating sequence of the strand residues imparts amphiphilicity to the folded hairpin. In addition to the lysine residues, APC1 contains a single glutamate at position 15 on its hydrophilic face. The residue is designed to form salt bridges with neighboring lysines, further stabilizing the peptide in its folded and assembled state (Rajagopal, et al. (2009) *Biomacromolecules* 10(9):2619-2625). The hydrophobic face of APC1 is largely comprised of β-sheet forming valine residues and a non-natural residue that allows the final gel-sol phase transition. Once folded, APC1 is designed to rapidly self-assemble into a fibrillar hydrogel network, where each fibril in the network is composed of a bilayer of β-hairpins that are intermolecularly hydrogen-bonded along the long-axis of a given fibril, FIGS. 2 and 3C. In this mechanism, the formation of the hydrophobic interface that defines the fibril bilayer is important as it provides most of the thermodynamic driving force for self-assembly. The bilayer is formed by the association of the hydrophobic faces of hairpins during assembly, a process driven thermodynamically by the hydrophobic effect (Pace, et al. (1996) *FASEB J.* 10(1):75-83). Earlier studies in our lab on other amphiphilic hairpins support this proposed mechanism of folding and assembly (Branco, et al. (2009) *Biomacromolecules* 10(6):1374-1380; Giano, et al. (2011) *Biomaterials* 32(27):6471-6477; Haines, et al. (2005) *J American Chemical Society* 127(48):17025-17029; Haines-Butterick, et al. (2007) *Proc. Nat'l Acad. Sci. U.S.A.* 104(19):7791-7796; Larsen, et al. (2009) *Macromolecules* 42(21):8443-8450; Nagarkar, et al. (2008) *J American Chemical Society* 130 (13):4466-4474; Nagy, et al. (2011) *J American Chemical Society* 133(38):14975-14977; Ozbas, et al. (2004) *Physical Review Letters* 93(26); Pochan, et al. (2003) *J American Chemical Society* 125(39):11802-11803; Rajagopal, et al. (2006) *European Biophysics J Biophysics Letters* 35(2):162-169; Salick, et al. (2007) *J American Chemical Society* 129(47):14793-14799; Schneider, et al. (2002) *J American Chemical Society* 124(50):15030-15037; Yucel, et al. (2008) *Macromolecules* 41(15):5763-5772). Germane to the application at hand, this triggered folding and assembly mechanism allows the facile preparation of gel with temporal resolution. Gels can simply be formed by: adding buffer of appropriate ionic strength to an aqueous solution of unfolded peptide; drawing the resulting solution into a syringe; and allowing it to gel at 25° C. directly in the syringe.

Hydrogels formed from amphiphilic hairpin peptides display shear-thin/recovery rheological behavior (Schneider, et al. (2002) *J American Chemical Society* 124(50):15030-15037; Altunbas, et al. (2011) *Biomaterials* 32(25):5906-5914; Branco, et al. (2010) *Biomaterials* 31(36):9527-9534; Rughani, et al. (2010) *Macromolecules* 43(19):7924-7930; Salick, et al. (2009) *Advanced Materials* 21(41):4120; Sinthuvanich, et al. (2012) *Biomaterials* 33(30):7478-7488; Veiga, et al. (2012) *Biomaterials* 33(35):8907-8916; Yan, et al. (2010) *Soft Matter* 6(20):5143-5156; Yan, et al. (2012) *Langmuir* 28(14):6076-6087). The physical interactions that stabilize these self-assembled fibrillar networks are non-covalent in nature. As such, when these gels experience a shear stress, such as that delivered by a syringe plunger, some of the non-covalent interactions within the network can be disrupted allowing the material to flow. When the application of shear stress ceases, the fibrillar network heals, immediately reforming the gel. The self-healing ability of the fibril network comes from the same inherent driving forces for self-assembly, namely the formation of hydrophobic contacts between hairpins as well as hydrogen-bonding. APC1 also exhibits this rheological behavior, which allows its syringe delivery to the collapsed lumen of blood vessels, where it re-establishes their shape and provides mechanical support that greatly facilitates the anastomosis procedure (FIG. 2, transition ii).

Figure 3A:
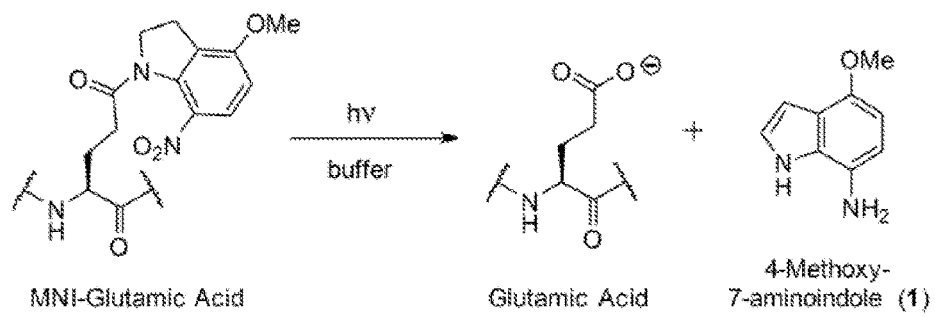
FIGS. 3A-3D illustrate the photocaged glutamate included in the disclosed peptides, and β-hairpin conformations including such peptides. (A) Photolysis reaction of 4-methoxy-7-nitroindolinyl glutamic acid (MNI-Glu) and sequences of photocaged peptides, along with the corresponding non-caged controls. (B) Structure of APC1 peptide in a β-hairpin conformation. (C) Energy minimized model showing the facial association of APC1 β-hairpins within the hydrophobic interface of the fibril bilayer. Two peptides stack on top of each other, with the hydrophobic face of the first peptide forming hydrophobic (van der Waals) interactions to the hydrophobic face of the second peptide. The lateral sides of the peptides form intermolecular interactions with adjacent peptides as the fibrill network expands. (D) Peel-away view of one monolayer showing the 'lock and key' packing arrangement of caged-side chains. The lockhole provided by the glycine is highlighted (arrow) in the top-most hairpin in the assembly. The photocage of the bottom-most hairpin is omitted for clarity. The N- and C-termini for one hairpin are labeled to orient the reader.
Figure 3B:
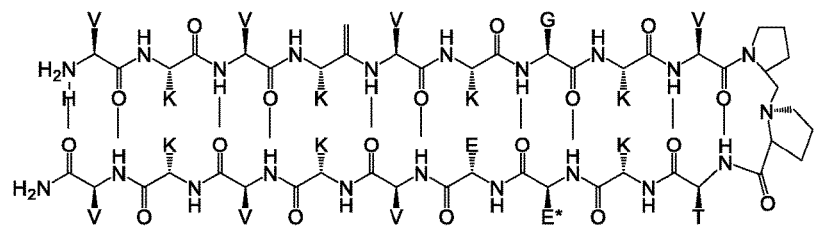
Figure 3C:
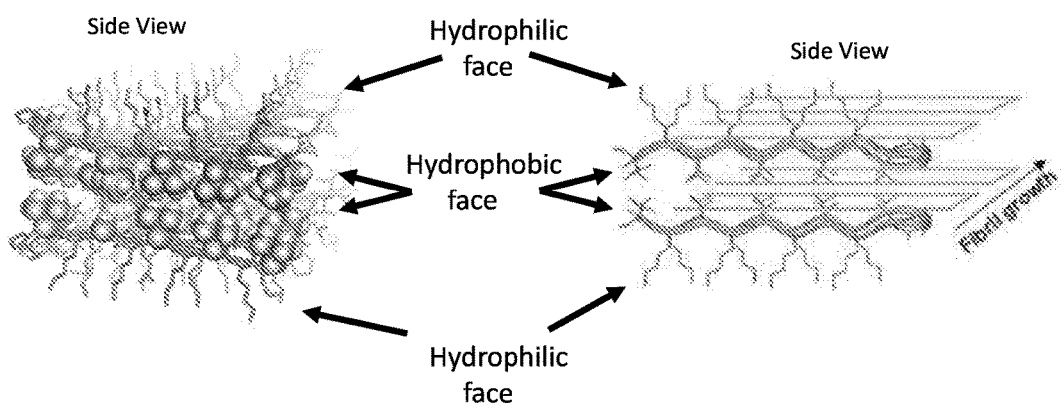
Figure 3D:
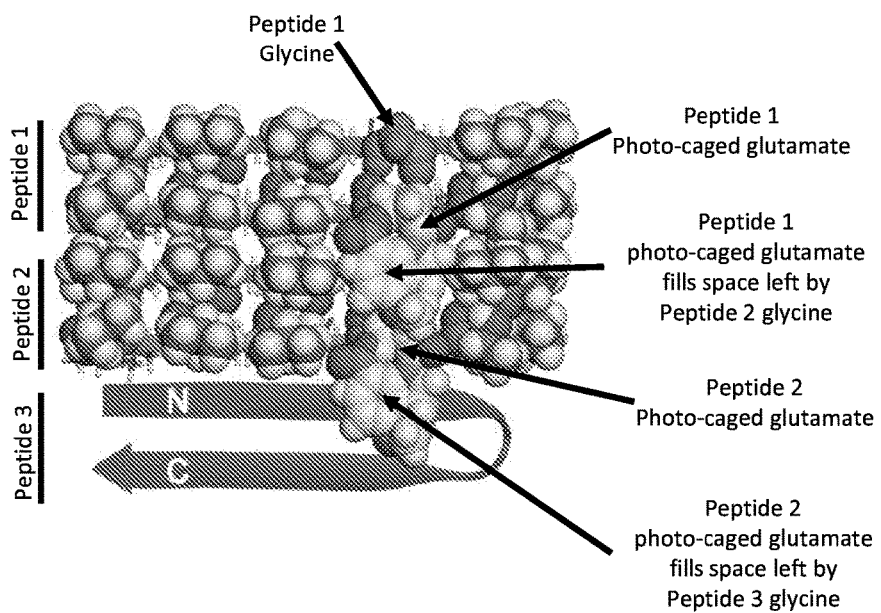
Figure 4A:
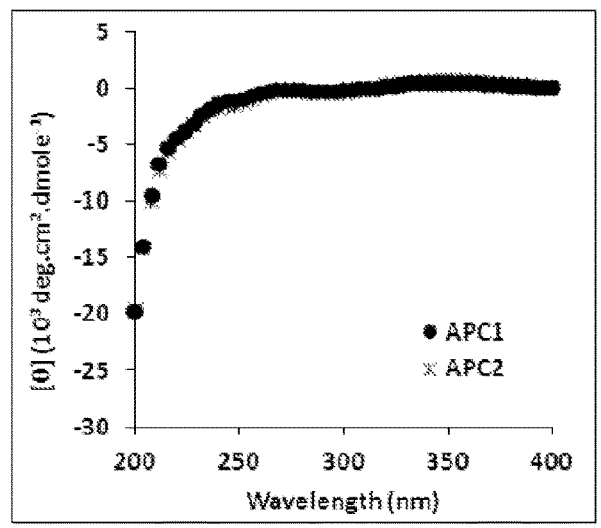
FIGS. 4A-4C illustrate formation of peptide hydrogels by the APC1 peptide. (A) CD wavelength spectra of 1% w/v APC1 and APC2 in water at 5° C. (B) Wavelength spectra of 1% w/v APC1 and APC2 hydrogels formed at pH 7.4 (150 mM NaCl) and 25 and 37° C., respectively. (C) Spectra of 1% w/v controls, cAPC1 and cAPC2, at pH 7.4 (150 mM NaCl) and 25 and 37° C., respectively.
Figure 4B:
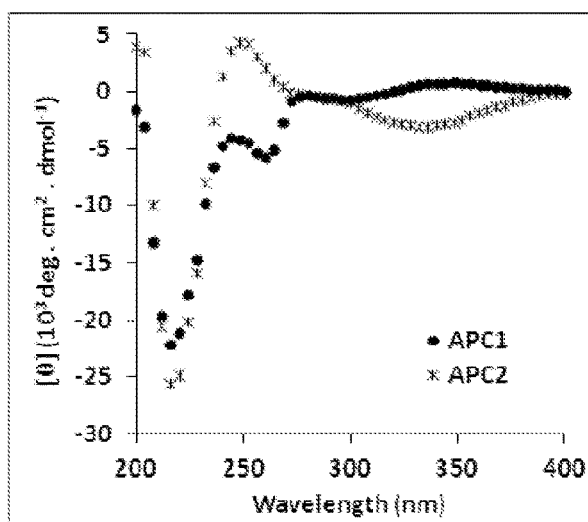
Figure 4C:
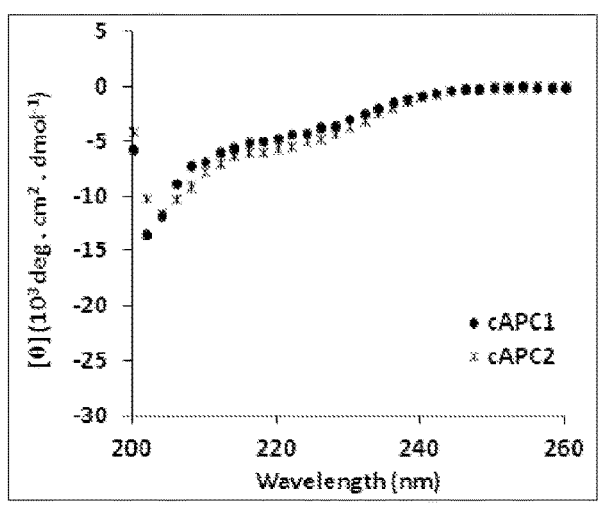
Figure 5A:
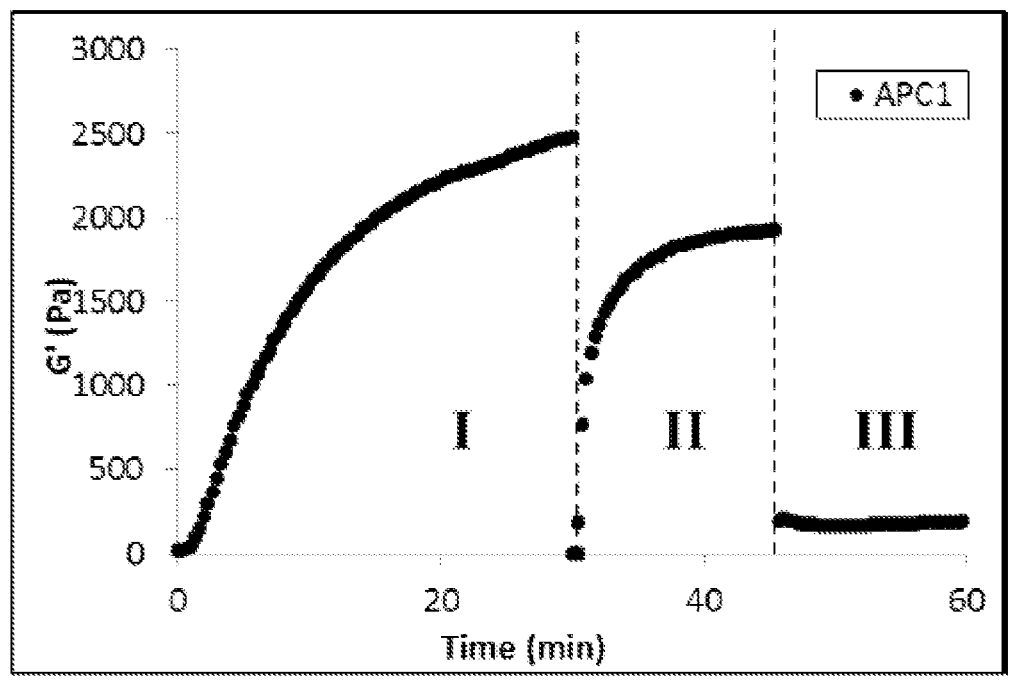
FIGS. 5A and 5B illustrate the rheological assessment of the formation, shear-thin/recovery and photodisruption of peptide hydrogels based on the APC1 (A) and APC2 (B) peptides. In regime I, a dynamic time sweep monitors the formation of each 1% wt/v gel after folding and assembly is triggered by measuring the storage modulus (G') as a function of time at pH 7.4 and 37° C. for APC1 and 25° C. for APC2; frequency=6 rad/s, 0.2% strain. In regime II, 1000% strain is applied for 30 seconds to thin the materials after which the strain is decreased to 0.2% to allow material recovery. In regime III, the recovered gels are irradiated at 365 nm for 10 minutes; G' is monitored during and after irradiation. The inset in panel B shows regimes II and III expanded. Independent frequency- and strain-sweep measurements (FIGS. 14-15), additional rheology experiments on preformed gels (FIG. 23) and atomic force microscopy measurements further support this rheological profile.

In the intact gel, the fibril bilayer is stabilized by nonpolar interactions made between residue side chains that pack together to form a hydrophobic interface that is shielded from water, FIG. 3C. In order to induce the final gel-sol transition and thereby achieve hydrogel dissolution after the blood vessel has been sutured, a polar, negatively charged side chain was introduced into peptide that would be energetically unfavorable and locally disruptive to the hydrophobic environment of the folded peptide. These disruptive local interactions are additive and result in the global destabilization of the fibril network defining the gel state. However, a negatively charged amino acid side chain capable of disrupting the hydrophobic bilayer would need to be temporarily masked as a neutral hydrophobic moiety to allow for all of the phase transitions necessary to implement the anastomosis procedure. Namely, the mask must allow the initial gelation of the peptide via the triggered folding and assembly mechanism described above and support the rheological shear-thin/recovery properties of the resultant gel. Further, its unmasking would have to occur with temporal resolution, preferably triggered by an external action implemented by the surgeon. With these criteria in mind, the design of APC1 incorporates a photocaged glutamic acid, namely 4-methoxy-7-nitroindolinyl glutamic acid [E(MNI)] on its hydrophobic face. In APC1's folded and assembled state, this caged side chain resides within the hydrophobic bilayer of the peptide fibril. When decaged with light, the peptide evolves a negatively charged glutamate side chain that should destabilize the gel network (FIG. 2, transition iii).

The 4-methoxy-7-nitroindoline (MNI) group was chosen as a suitable photocage for glutamic acid due to its stability and rapid, efficient photolysis in aqueous solution (Canepari, et al. (2001) *J Neuroscience Methods* 112(1):29-42). FIG. 3A shows the photolysis of MNI-caged glutamic acid that occurs using 365 nm light, or alternatively through 2-photon irradiation at 720 nm, to yield the free glutamate and aminoindole byproduct 1. The caged glutamate was incorporated at position 14 of APC1's primary sequence. This is a central position on the hairpin's hydrophobic face that corresponds to a fully buried site within the fibril bilayer. Decaging should generate a series of negative point charges along the entire fibril length within its hydrophobic interior providing the driving force for the destabilization of the gel's fibril network.

Incorporation of the large MNI-caged glutamic acid within the primary sequence of APC1 necessitates the placement of a glycine residue on the opposing strand of the hairpin at position 7. In the self-assembled state, the small glycine provides a hole on the hydrophobic face of one folded hairpin into which the caged side chain from a neighboring hairpin can reside. This 'lock and key' side chain packing arrangement accommodates the large photocage within the tight steric constraints of the bilayer interior. Similar accommodations are a common motif in naturally occurring β-sheet proteins. For example, tryptophan residues are often found in sheet interiors with their bulky side chains laying over a small residue in a neighboring strand of the sheet (Wouters, et al. (1995) *Proteins-Structure Function and Genetics* 22(2):119-131). Molecular modeling shows that in the context of the APC1 hairpin, this arrangement results in a well-packed hydrophobic face that is conducive to bilayer formation (FIG. 3C) to facilitate the self-assembly mechanism leading to gel formation. FIG. 3D shows a cut-away view of one monolayer formed from three hairpins. Here, the caged side chain from one hairpin lays over the glycine of a neighboring hairpin below it, with the indoline group making hydrophobic contacts with proximal valine side chains. The top-most hairpin in the assembly shown in panel C highlights the glycine hole into which a photocaged side chain could be placed if an additional hairpin where to join the fibril assembly.

In addition to APC1, a second peptide was designed to study the positional effect of cage placement on gel performance. Peptide APC2 contains the [E(MNI)] residue at position 16, which is slightly closer to the hairpin's N- and C-termini Correspondingly, a glycine residue was incorporated at position 5. Two control peptides were also prepared, namely cAPC1 and cAPC2, which contain uncaged glutamate residues at positions 14 and 16, respectively. Peptides were prepared by Fmoc-based solid phase peptide synthesis (FIGS. 11A-11D and FIGS. 12A-12D) employing Fmoc-protected [E(MNI)], which was synthesized using a modified literature procedure (Papageorgiou, et al. (2004) *J Organic Chemistry* 69(21):7228-7233) as outlined in the methods section.

Folding and Assembly of APC Peptides and Rheological Properties of their Gels.

The ability of APC1 and APC2 to fold and associate into β-sheet rich assemblies was monitored using circular dichroism (CD) spectroscopy. In water at 5° C., the CD spectra of 1% w/v solutions of APC1 and APC2 indicate that the peptides are unfolded under these conditions (FIG. 4A). However, FIG. 4B shows that folding and self-assembly can be triggered by adding pH 7.4 buffer that contains NaCl to the aqueous peptide solution and increasing the temperature to 25° C. for APC1 and to 37° C. for APC2. The NaCl screens the lysine point charges and increasing the temperature drives the hydrophobic effect, both of which favor folding and assembly. The exact temperatures needed to induce folding and assembly of each peptide were determined by monitoring the mean ellipticity at 216 nm as a function of temperature as shown in FIG. 13. In all the CD experiments, self-supporting hydrogels of both peptides (pH 7.4, 150 mM NaCl) form directly in the cuvette after folding is triggered. The same procedure can be used to form the gels directly in a syringe. At any rate, spectra of both peptides under these solution conditions in the gelled state display distinct minima at 216 nm, which is indicative of β-sheet secondary structure. Also evident in the spectra are absorptions due to the indoline cage, which occur in the near UV-CD (240-380 nm). These absorptions do not appear in the CD spectra of the unfolded peptides. This indicates that in the unfolded state of each peptide, the achiral aromatic indoline ring resides in an achiral environment, that is, it is solvent exposed. However, when the peptides fold and assemble, the indoline ring is placed into a chiral environment, such as that provided by the fibril's hydrophobic interior. FIG. 4C shows that under the same solution conditions that support the folding and assembly of APC1 and APC2, the control peptides cAPC1 and cAPC2 remain unfolded, FIG. 4C. This observation suggests that the control peptides' negatively charged glutamate side chains are not accommodated within the hydrophobic interior of the fibril bilayer and thus, peptide folding and assembly are disfavored. Importantly, it also supports the assertion that if the glutamate's negative point-charge were to be unmasked when the peptides are in the folded and assembled fibrillar state, that this event should be disruptive.

Oscillatory rheology was employed to study the rheological behavior of each gel under experimental conditions that mimic its use during the anastomosis procedure. Here, the storage modulus (G'), a measure of the gels' mechanical rigidity, is monitored in the rheometer under environmental conditions that mimic: (1) the initial (sol-gel) formation of the hydrogel in the syringe; (2) shear thinning of the material as it passes through the syringe needle during injection with subsequent hydrogel recovery in the vessel lumen; and (3) the disruption of the gel network (gel-sol) by UV photolysis after suturing. Monitoring gel behavior in a rheometer, although not exactly capturing the gel's response during the actual anastomosis procedure, allows quantitative and reproducible measurement of gel mechanical properties under highly controlled conditions. FIG. 5A shows the data for APC1. In regime I, the rate of hydrogel formation (sol-gel) is assessed in a time-sweep experiment that monitors the evolution of G' after peptide folding and assembly is triggered for a 1% w/v solution of peptide. The data show that APC1 forms a semi-rigid gel within the first few minutes after triggering that further rigidifies with time (G'~2,500 Pa after 30 minutes). After completion of the initial time sweep, 1000% strain is applied to the material for 30 seconds in regime II to mimic syringe delivery of the gel. This application of strain results in an immediate decrease in G' indicative of shear thinning that results in a viscous gel capable of flow. After the 30 seconds, the applied strain is decreased to 0.2% and the material is allowed to recover. The data show that the APC1 gel network quickly heals recovering about 75% (1900 Pa) of its original rigidity. Lastly, using an optically clear parallel plate in the rheometer, the recovered hydrogel is subjected to irradiation by UV light (365 nm) for the first 10 minutes of regime III, where the effect of photolysis on the storage modulus is monitored over time. The data clearly show that the gel network is rapidly degraded with an almost immediate decrease of G' to ~180 Pa. Taken together, the rheological data suggests that APC1 is capable of triggered gelation, shear-thin delivery via syringe and rapid post-delivery recovery. Importantly, irradiation by UV rapidly disrupts the gel network affording a viscous material, which should be capable of dissolution when exposed to the shear of blood flow. Independent frequency- and strain-sweep measurements were also performed as shown in FIGS. 14A-14B and FIGS. 15A-15B.

Additionally, atomic force microscopy (AFM) measurements of preformed 1 wt % APC1 gels in PBS buffer was performed. Force-indentation data was fit to the Hertz contact model to extract the elastic modulus (E). Storage modulus (G') was calculated using $G'=E/[2(1-v)]$, where the Poisson's ratio (v) was approximated to be 0 for a highly porous material. The results showed that the assayed gels had an Elastic Young's Modulus (E) or 10.6±7.3 kPa, and a Storage Modulus (G') of 5.3±3.7 kPa.

Figure 5B:
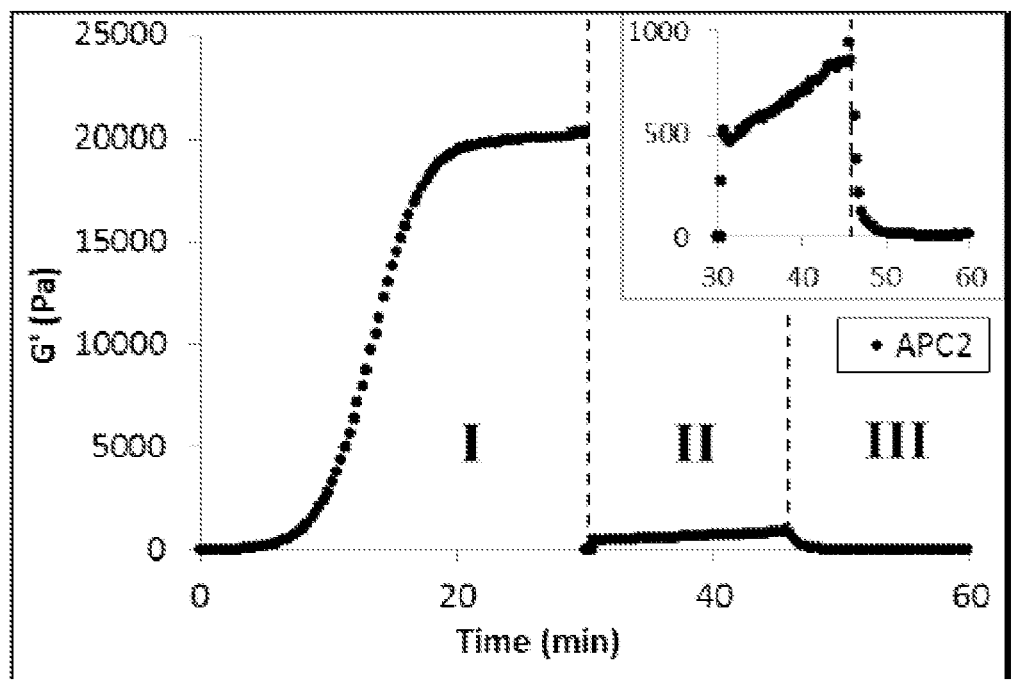

FIG. 5B shows the same experiment for the APC2 gel. Regime I shows that there is a significant lag phase before the onset of gelation. However, with time, APC2 folds and assembles affording a gel that is significantly more stiff (20,000 Pa) then that formed from APC1. Application of 1000% strain in the first 30 sec. of regime II quickly thins the APC2 gel. However, the resulting viscous material is unable to self-heal effectively and recovers only about 5% of its original mechanical rigidity. Finally, irradiation in regime III disrupts the weakly recovered gel. Although APC2 is initially able to form a very rigid gel, its inability to recover after being shear thinned precludes it use in the anastomosis procedure. With respect to the design of this class of hairpin peptides, the rheological data indicates that the positional placement of the photocage within the peptide's primary sequence is important. Here, incorporation of the cage near the strand termini of the hairpin hampers the ability of the network to recover. Based on this rheological assessment, the APC1 gel was chosen for further study.

Examination of the Decaging Event and its Effect on Fibril Network Morphology

Figure 6B:
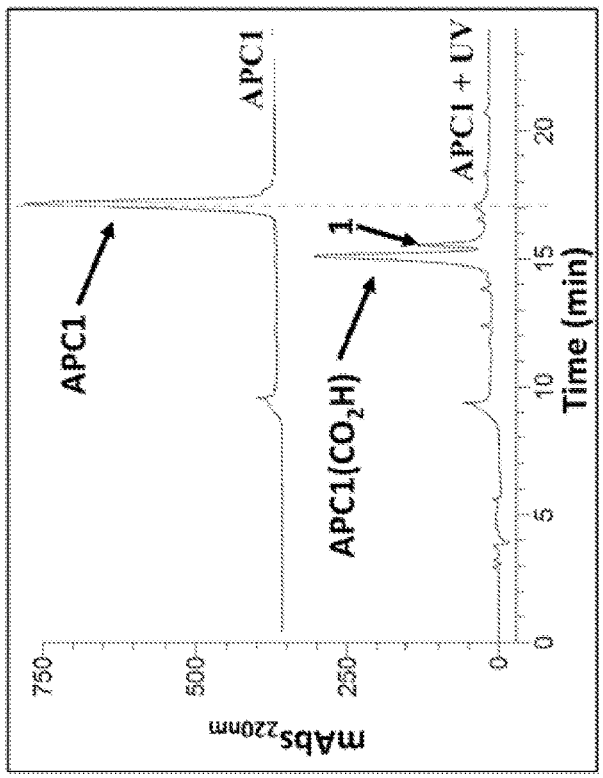
FIGS. 6A and 6B illustrate uncaging of the caged glutamate on the APC1 peptide. (A) UV absorbance of APC1's indoline cage as a function of time during photolysis. The absorbance of APC1 at 248 nm is followed as a function of time during irradiation. Absorbance at this wavelength is mainly due to the intact indoline cage. The observed rapid decrease in absorbance indicates that the indoline cage has undergone almost complete photolysis after 90 seconds of irradiation. Image shown represents averaged absorbance data for three independent experiments, with a variance in photometric accuracy of 0.005 AU. (B) RP-HPLC chromatograms of APC1. The top chromatogram shows intact APC1. The bottom chromatogram shows that after photolysis, uncaged peptide bearing a free glutamate side chain is produced along with the released photocage by-product 1. Mass spectroscopy was used to confirm the identity of both species.
Figure 6A:
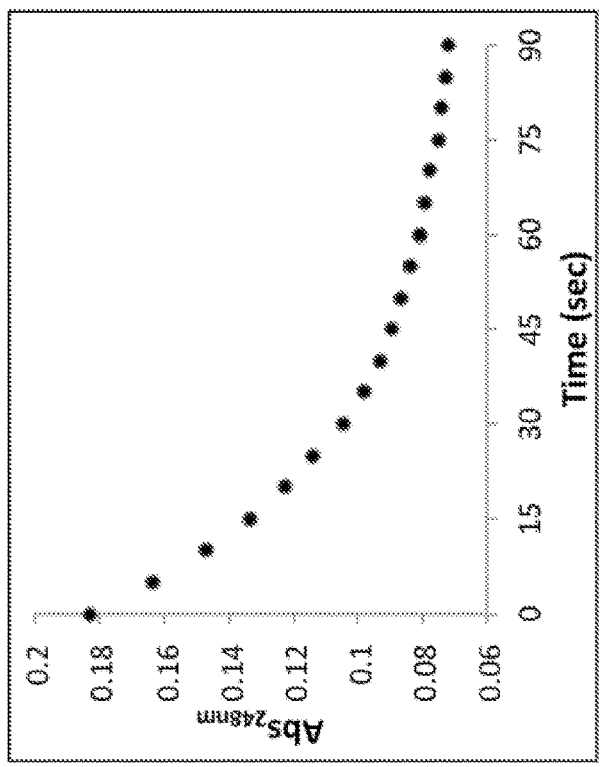

The rheological data in FIGS. 5A and 5B shows that irradiation of the recovered APC1 gel leads to a significant decrease in G' presumably as a result of decaging the glutamate side chain. FIGS. 6A and 6B test that assertion by following the fate of both the 4-methoxy-7-nitroindoline (MNI) group as well as the caged peptide during photolysis. In FIG. 6A, the absorbance of APC1 at 248 nm is followed as a function of time during irradiation. Absorbance at this wavelength is mainly due to the intact indoline cage. The observed rapid decrease in absorbance indicates that the indoline cage has undergone almost complete photolysis after 90 seconds of irradiation. In FIG. 6B, photolysis of the caged peptide is followed by RP-HPLC. The top chromatogram shows intact APC1. The bottom chromatogram shows that after photolysis, uncaged peptide bearing a free glutamate side chain is produced along with the released photocage by-product 1. Mass spectroscopy was used to confirm the identity of both species.

Figure 16A:
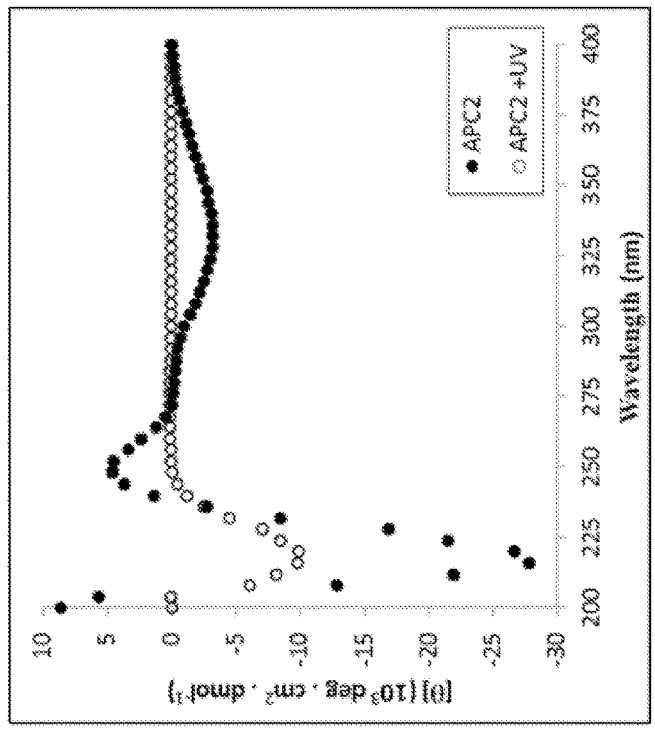
FIGS. 16A-16B show circular dichroism analysis of APC1 and APC2 hydrogels before and after photodisruption. (A) Circular dichroism wavelength spectrum of 1% w/v APC1 (pH 7.4, 25° C.) before (●) and after (○) UV photolysis at 365 nm. (B) Circular dichroism wavelength spectrum of 1% w/v APC2 (pH 7.4, 37° C.) before (●) and after (○) UV photolysis at 365 nm.
Figure 16B:
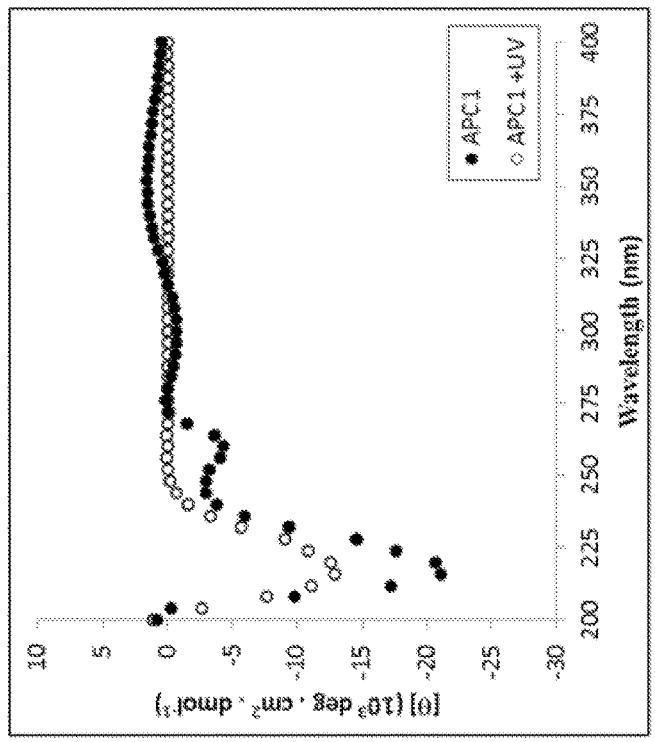
Figure 17A:
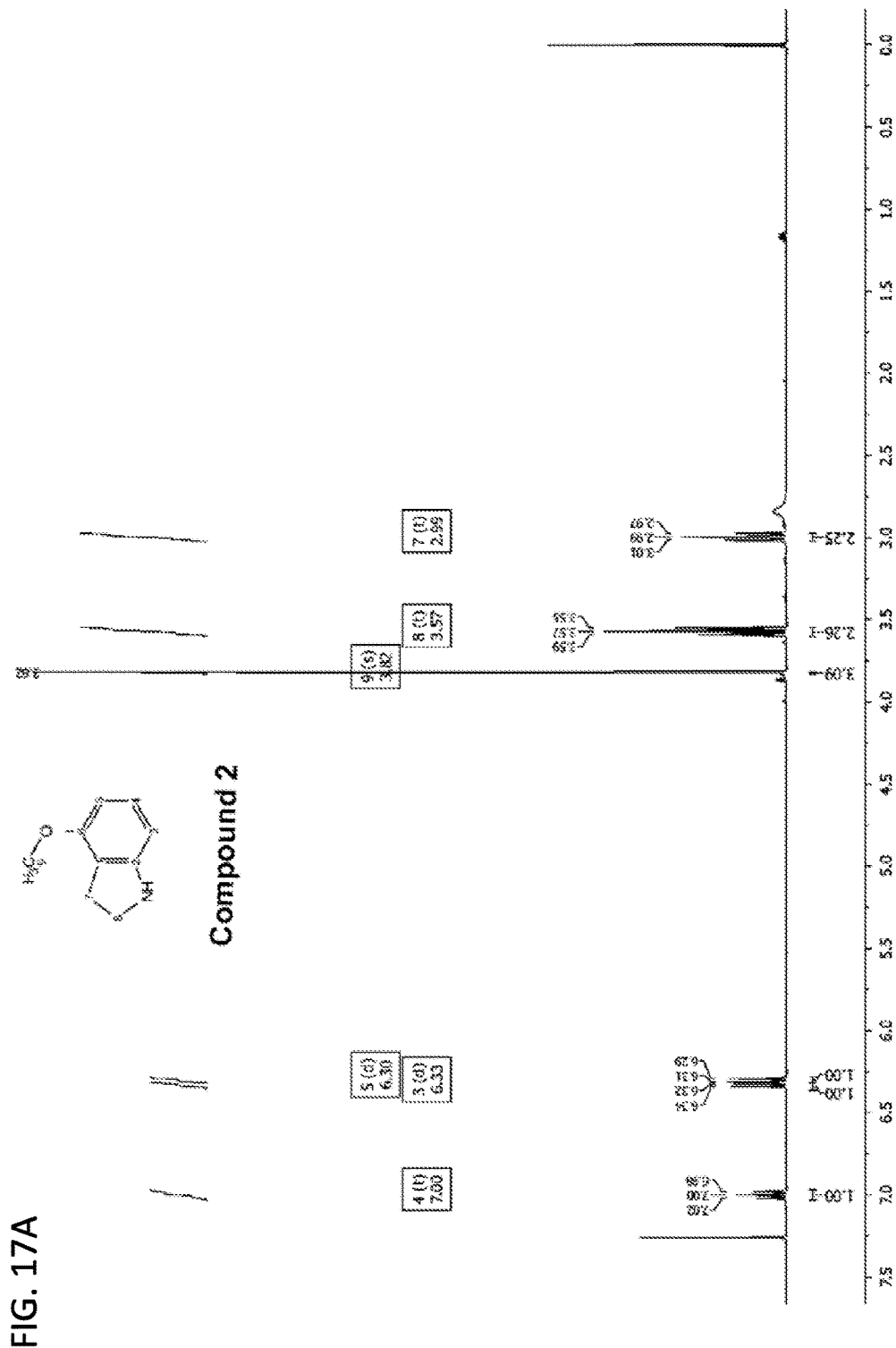
FIGS. 17A-22B show HPLC analysis of Compounds 2-7 that were generated for preparation of a photocaged glutamate residue Fmoc-Glu(MNI)-OH. HPLC analysis is shown for 4-Methoxyindoline (Compound 2, FIGS. 17A-17B), 4-Methoxyindolinyl N-α-(tert-butoxycarbonyl)-L-glutamic acid α-tert-butyl ester (Compound 3, FIGS. 18A-18B), 4-Methoxyindolinyl N-α-(di-tert-butoxycarbonyl)-L-glutamic acid α-tert-butyl ester (Compound 4, FIGS. 19A-19B), 4-Methoxy-7-nitroindolinyl N-α-(di-tert-butoxycarbonyl)-L-glutamic acid α-tert-butyl ester (Compound 5, FIGS. 20A-20B). 4-Methoxy-7-nitroindolinyl N-α-(tert-butoxycarbonyl)-L-glutamic acid α-tert-butyl ester (Compound 6, FIGS. 21A-21B), and 4-Methoxy-7-nitroindolinyl N-α-(9-fluorenylmethyloxycarbonyl)-L-glutamic acid (Compound 7, FIGS. 22A-22B).
Figure 17B:
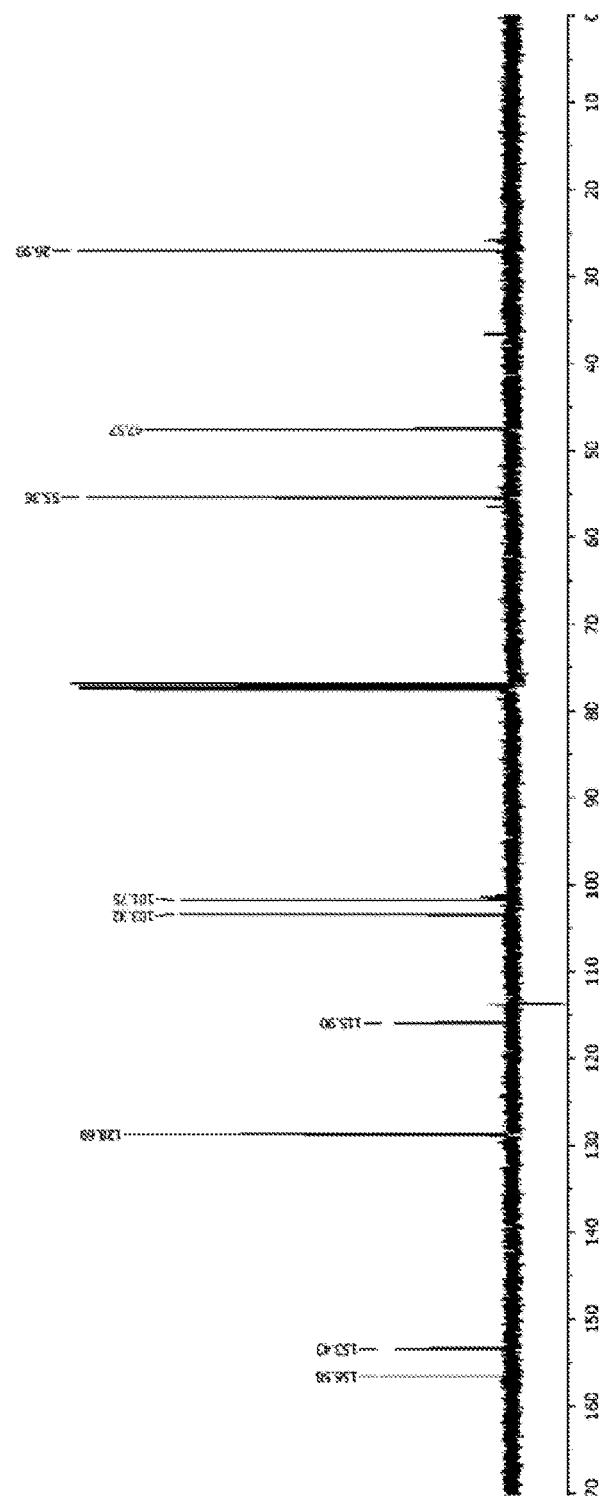
Figure 18A:
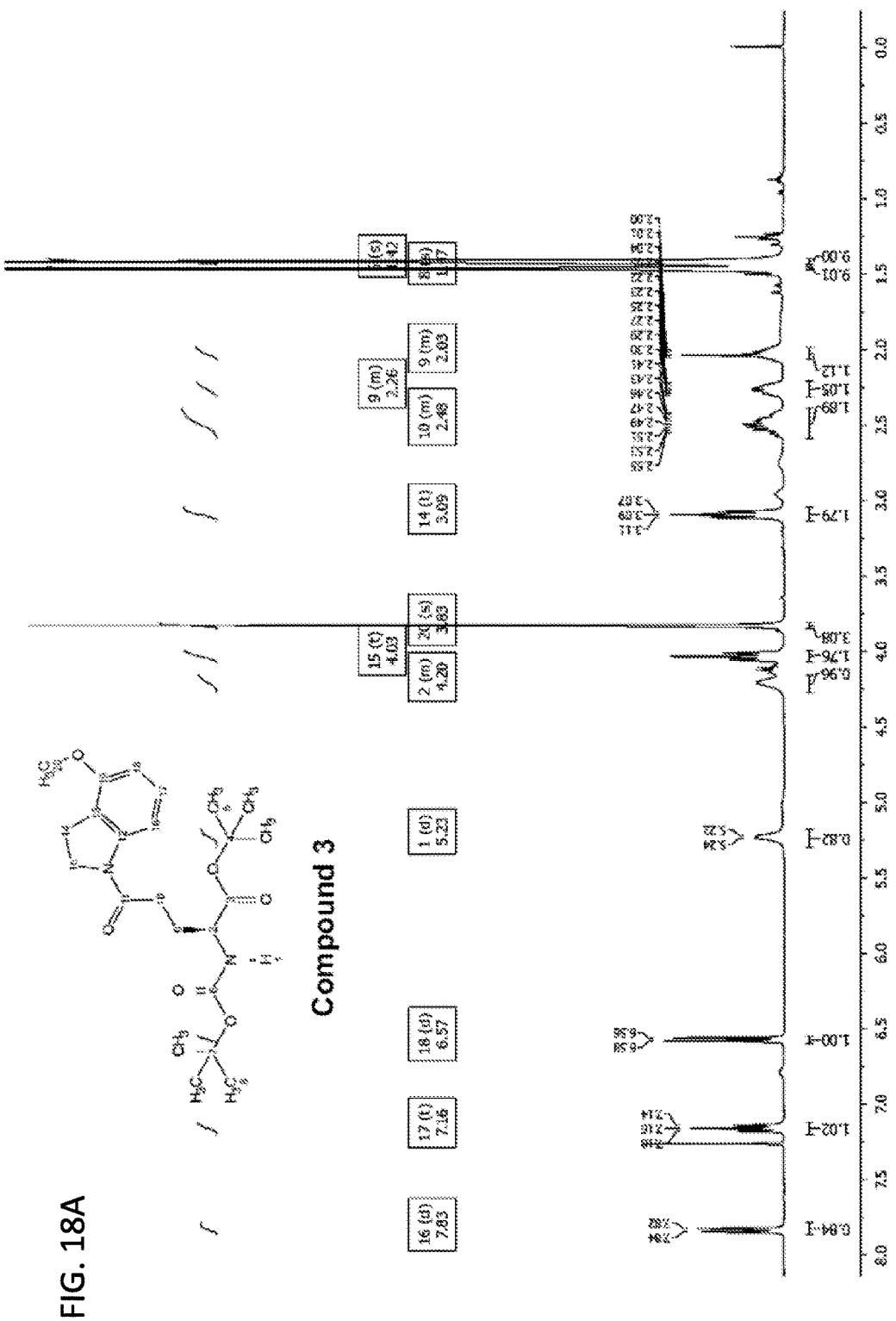
Figure 18B:
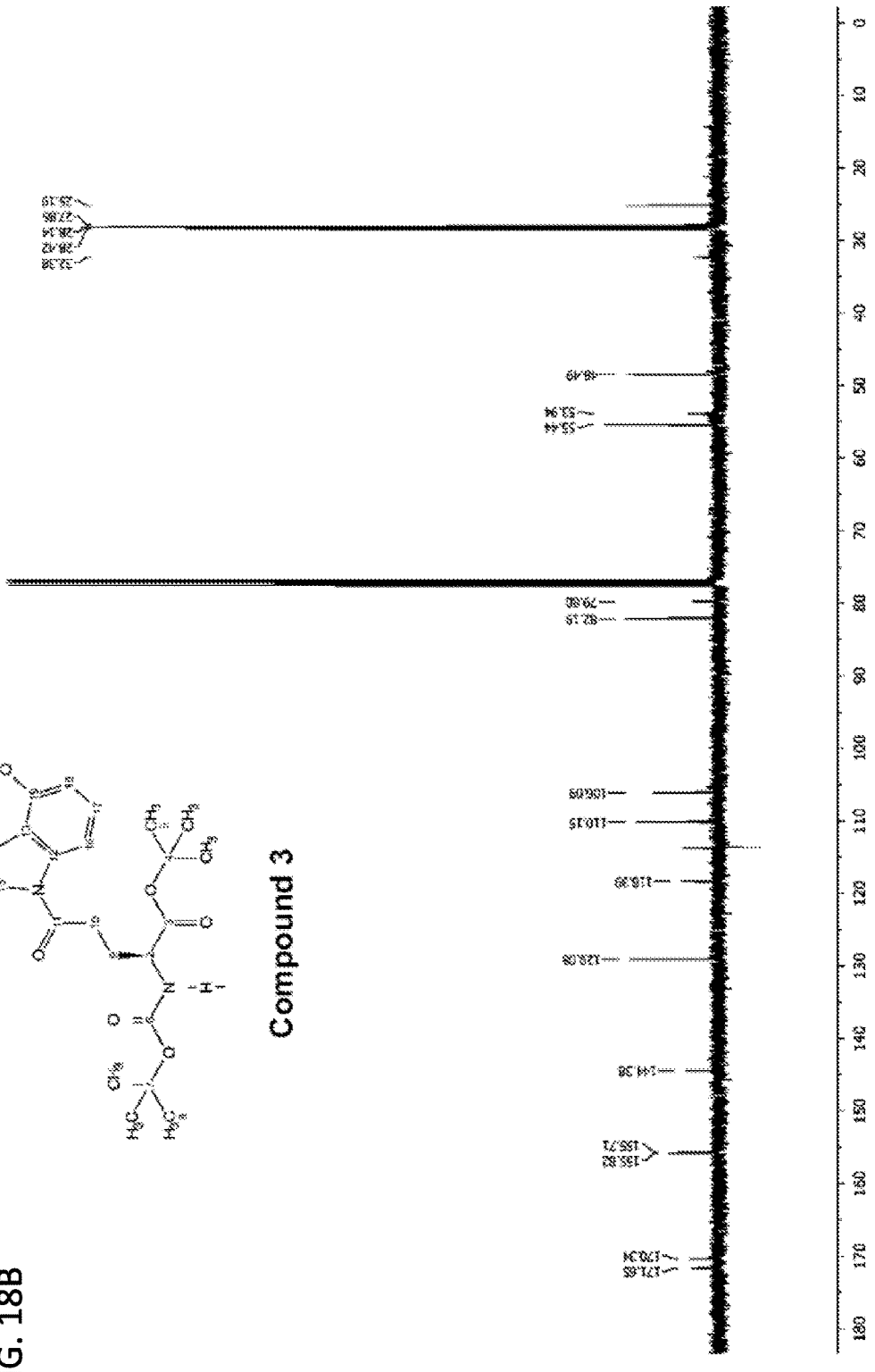
Figure 19A:
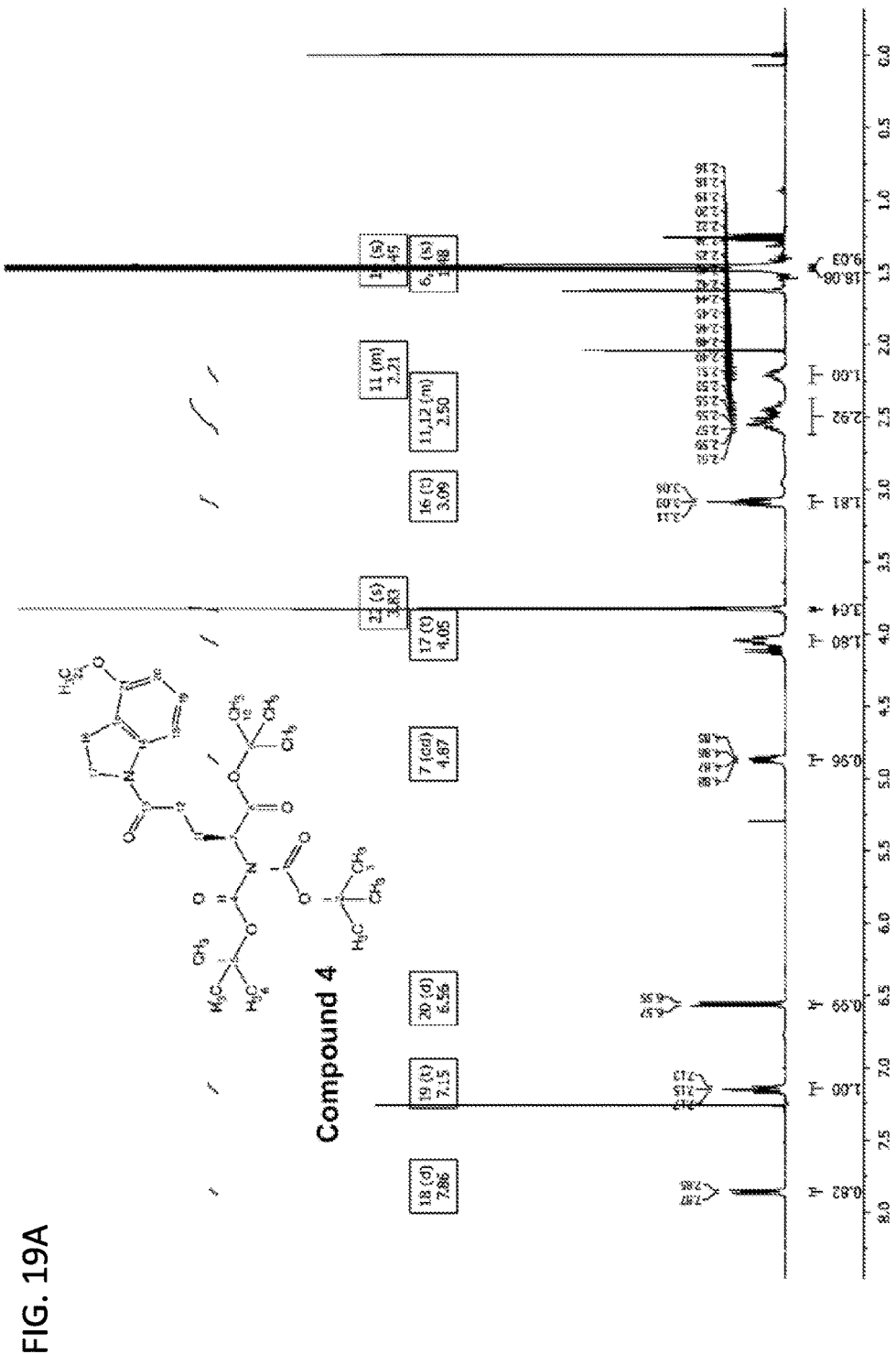
Figure 19B:
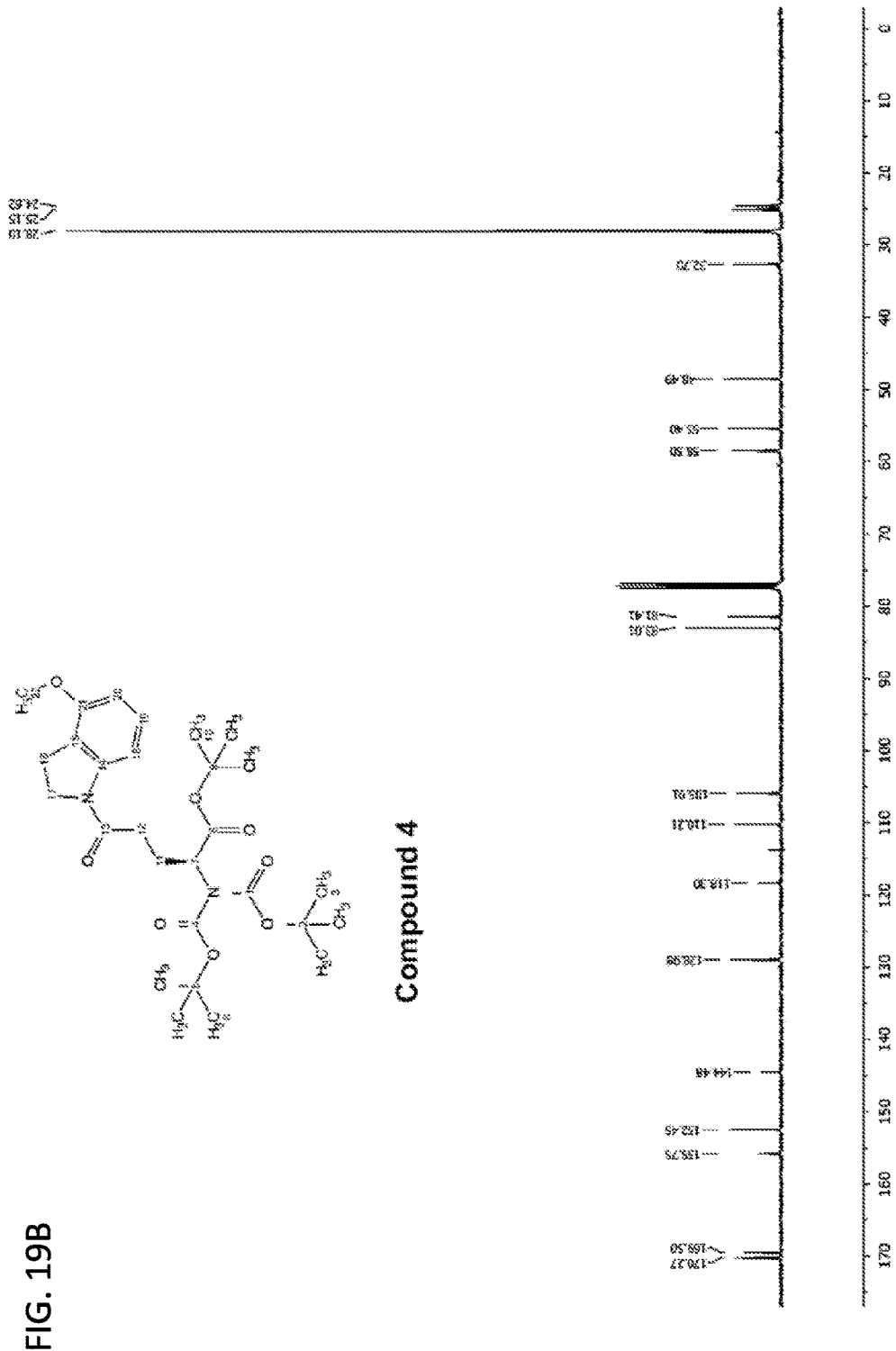
Figure 20A:
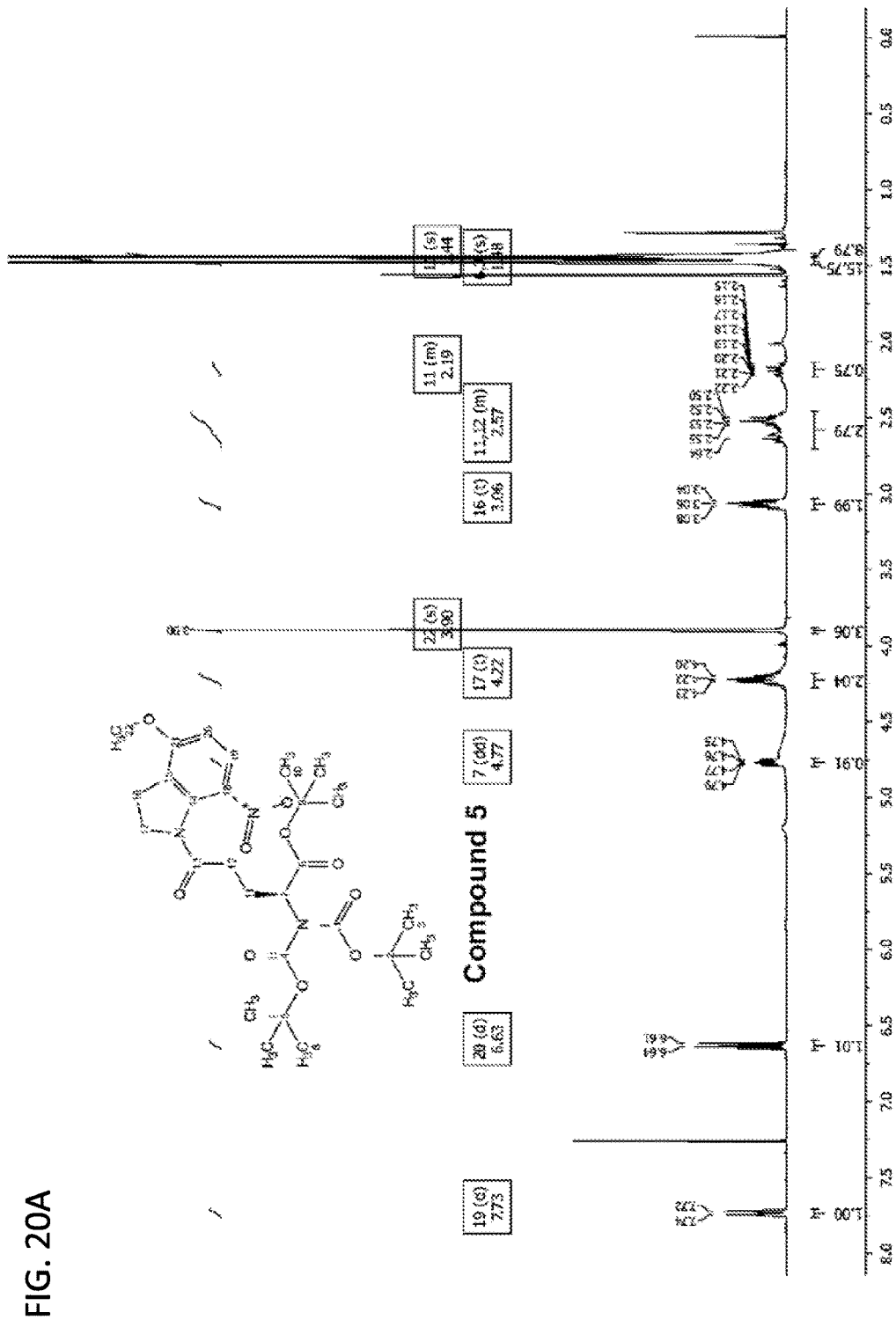
Figure 20B:
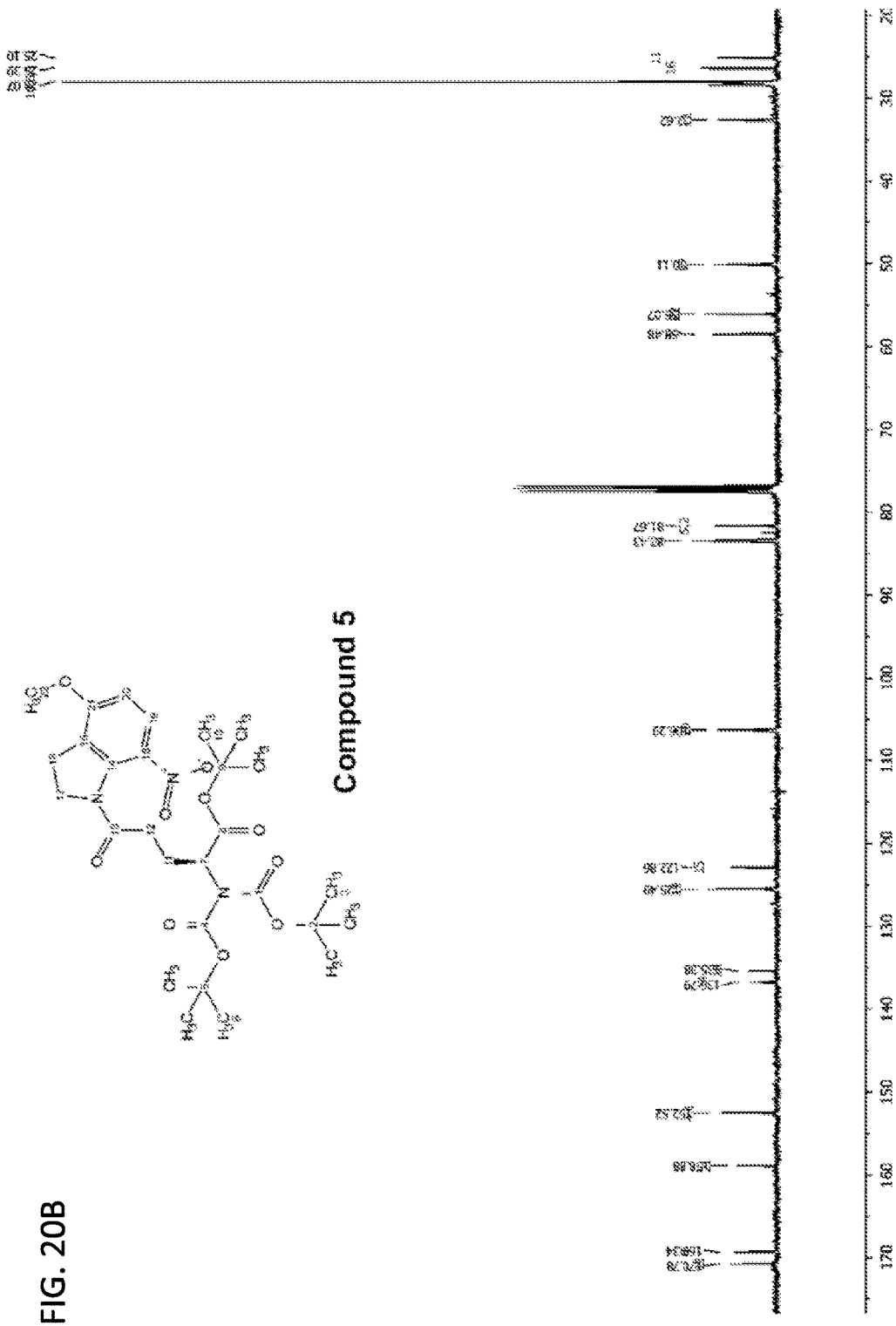
Figure 21A:
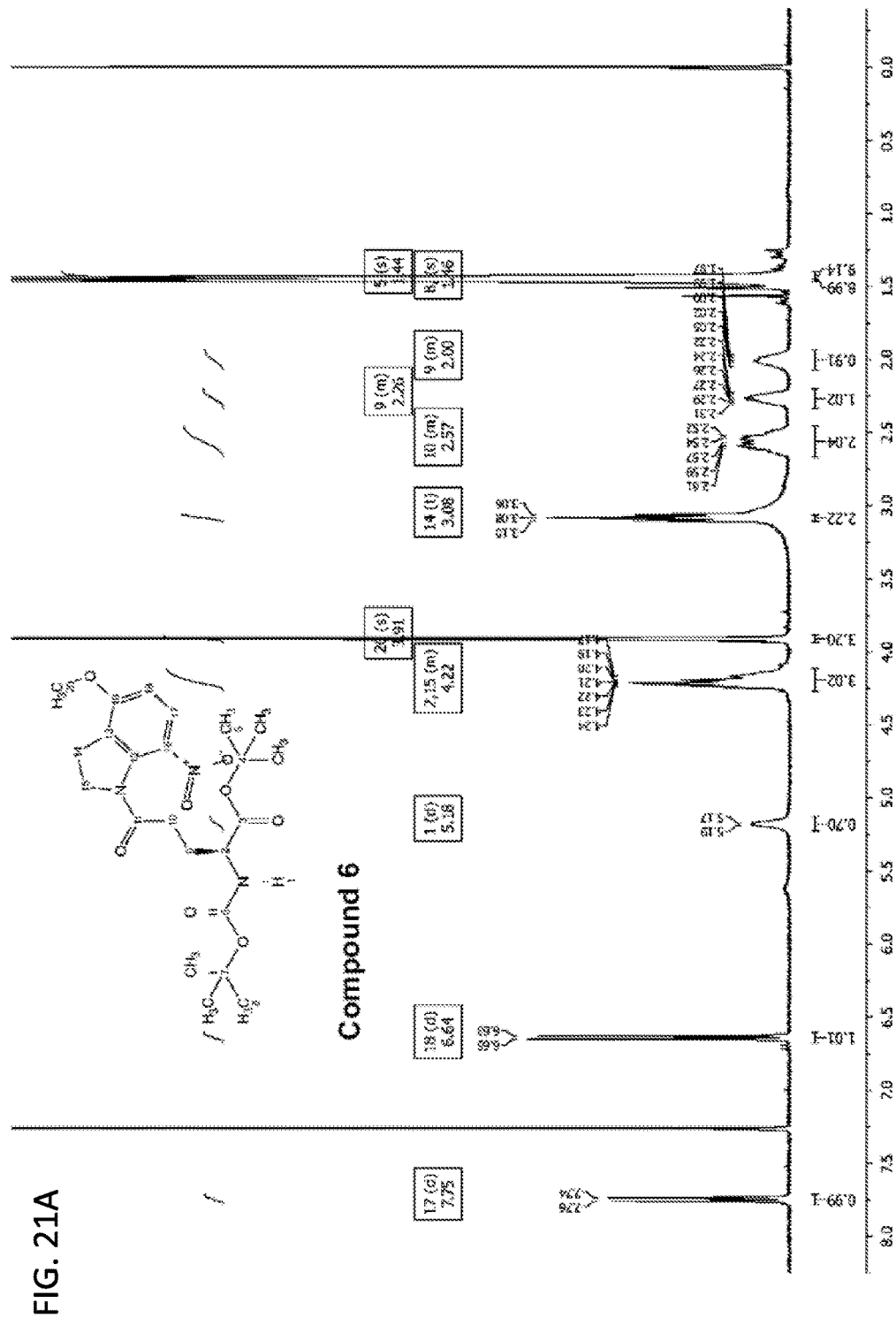
Figure 21B:
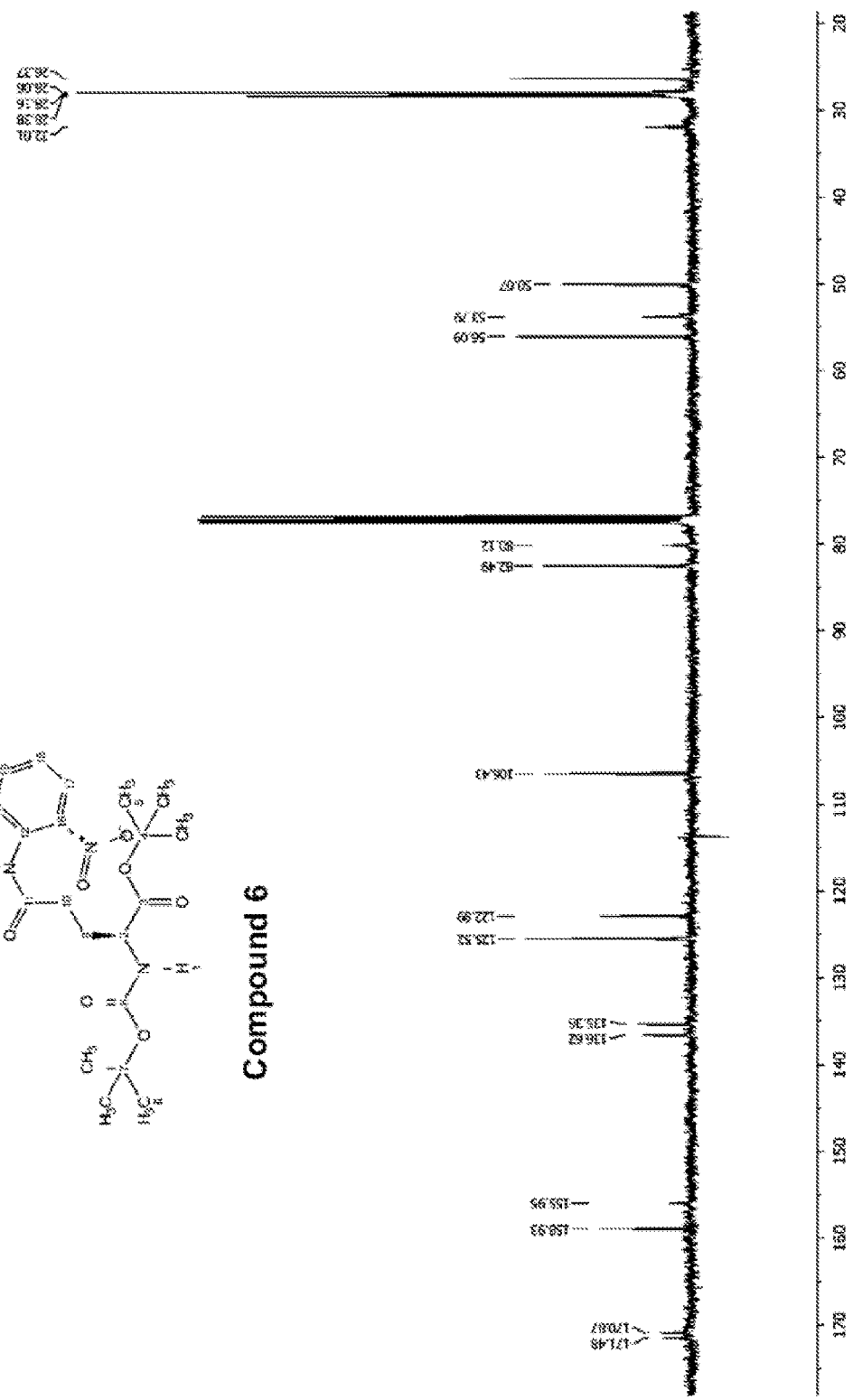
Figure 22A:
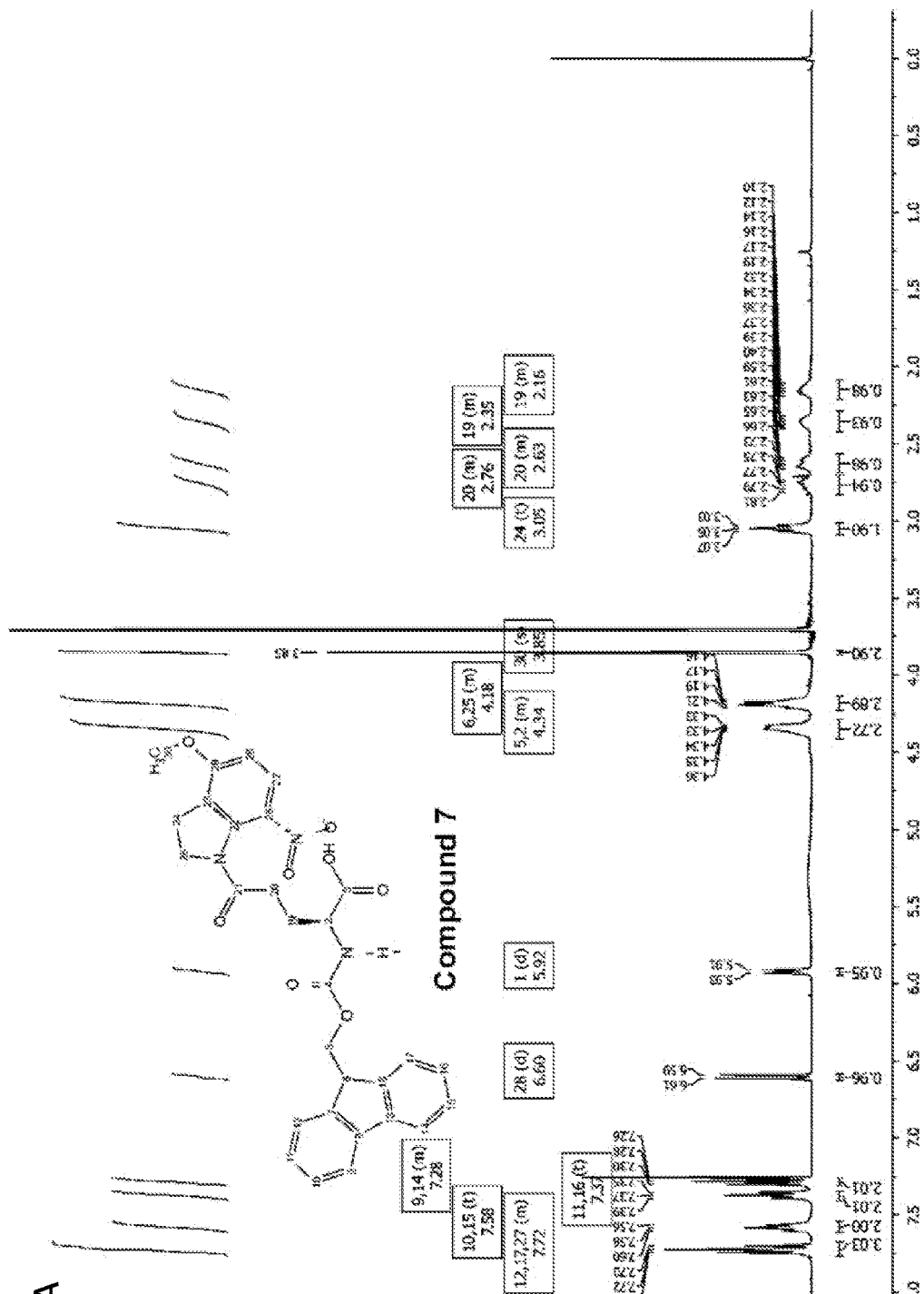
Figure 22B:
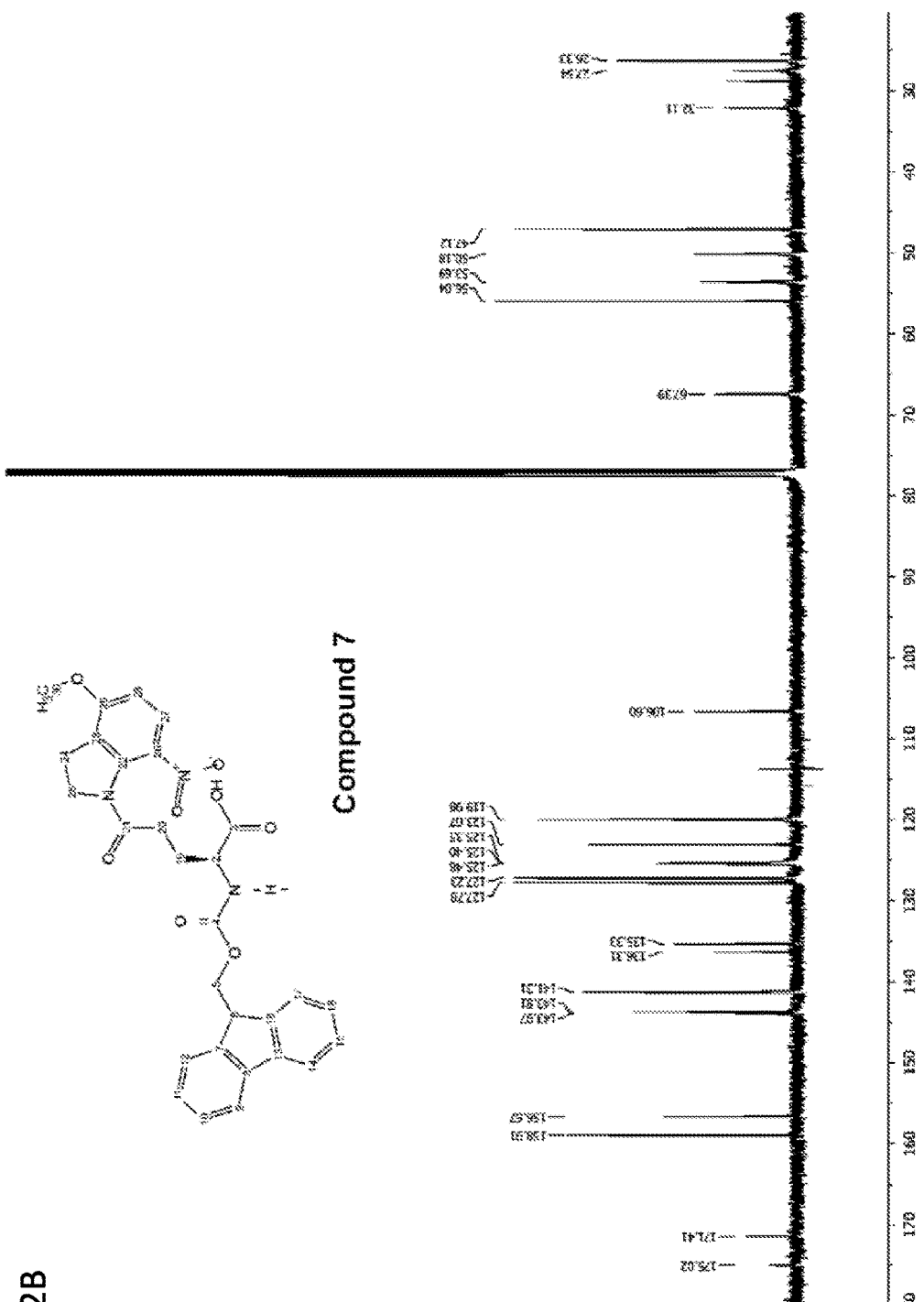
Figure 23A:
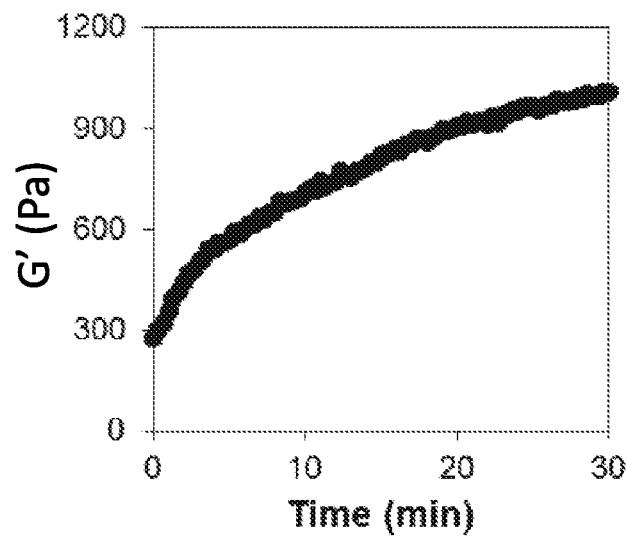
FIGS. 23A and 23B show rheological assessment of preformed APC1 gels to approximate material properties in a syringe. Dynamic time sweep of a pre-formed 1 wt % gel following its shear-thin delivery from a syringe directly onto the rheometer plate (A). Dynamic time sweep of a pre-formed gel slab that was transferred to the rheometer plate (B). Storage modulus (G") was monitored as a function of time at pH 7.4 and 37° C.; frequency=6 rad/s, 0.2% strain. For the preformed gel slabs (B), at 15 minutes 1000% strain was applied for 30 seconds to thin the material, after which the strain is decreased to 0.2% to allow material recovery.
Figure 23B:
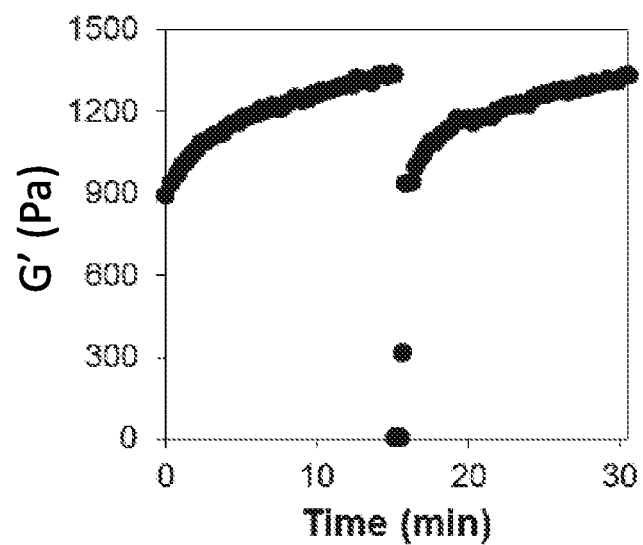

Using transmission electron microscopy (TEM), we investigated the effect that photolysis had on the local morphology of the fibrils that constitute the gel. FIGS. 7A-7D show TEM images of fibrils isolated from a 1% w/v APC1 hydrogel before (FIG. 7A) and after (FIG. 7B) irradiation. Before irradiation, the hydrogel network is composed of long fibrils whose lengths are distributed over a range of 150 nm to over 1000 nm, as shown statistically in FIG. 7C. Irradiation results in the formation of small fibril segments as shown in FIGS. 7B and 7D. The average length of these fibrils is on the order of ~150 nm. Comparing the statistical analysis provided in FIGS. 7C and 7D shows that the majority of longer fibrils have been converted to smaller segments as a result of photolysis. Further, CD spectroscopy of the irradiated gel shows an attenuation of β-sheet signal at 216 nm, which is consistent with the disruption of the fibril network, FIGS. 16A and 16B. CD spectroscopy, TEM and rheological analysis all support a mechanism of light-induced decaging that leads to the disruption of the fibrils that constitute the gel. The degree of fibril disruption afforded by irradiating the gel network is sufficient to initiate the necessary gel-sol transition under the environmental shear force conditions exerted by the flow of blood within a vessel.

In Vivo Assessment of CP1 Hydrogel in a Mouse Model of Microvascular Anastomosis Difficulties associated with anastomosis, especially on the micron length scale, include increased risk of vessel damage and the misplacement of sutures that occlude the vascular lumen. The ability of the APC1 hydrogel to serve as a temporary stabilizer capable of aiding the suturing process was assessed in a mouse femoral artery end-to-end anastomosis model. This model provides a challenging microsurgical setting to assess the gel with regards to ease, safety, precision, and speed of an arterial anastomosis. Anastomosing the mouse femoral artery with a diameter of approximately 200 microns is barely possible with conventional microvascular techniques. For a vessel of this size, a minimally traumatic technique for anastomosis is mandatory. Conventionally, a no-touch technique is facilitated by underwater suturing, a technically challenging and time-consuming procedure due to the instability of the floating vessel ends. In contrast, the APC1 hydrogel is designed for facile administration directly to the in situ vessel to distend the lumen and add stability to the vessel wall. This should enable more precise and quick placement of stitches, resulting in increased vessel patency.

Figure 8A:
FIGS. 8A-8G shows assessment of vessel patency before and after gel-based anastomosis.
Figure 8B:
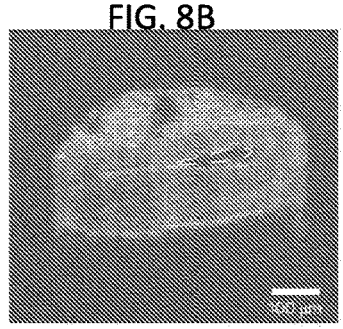

In this example, an incision was first made in the groin crease of mice to expose the femoral artery, which was dissected and subsequently clamped, FIG. 8A. In FIG. 8B a cross-section of the resulting lumen is shown imaged by optical coherence tomography (OCT), a technique that has proven useful in evaluating the quality of suture placement within small blood vessels (Huang, et al. (2013) *J Biomedi-*

Figure 8C:
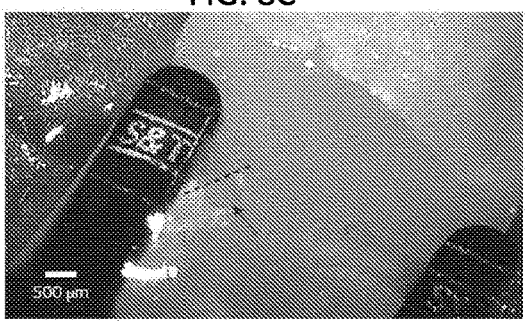
Figure 8D:
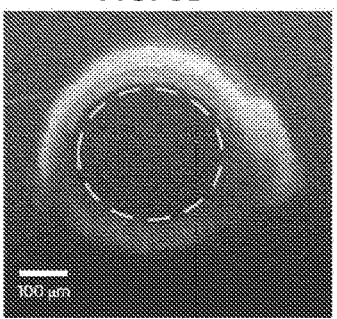
Figure 8E:
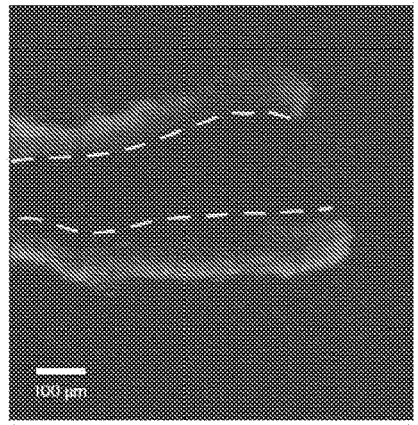
Figure 8E:
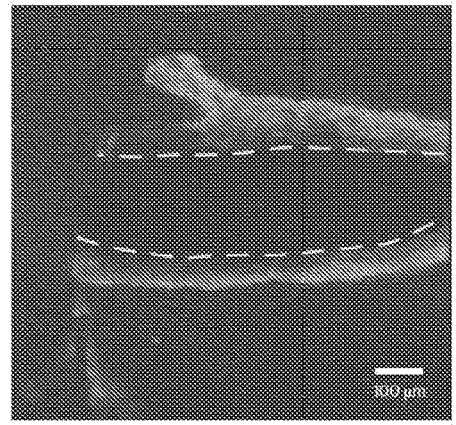

*cal Optics* 18(11)). In this image, it is clear that the lumen, indicated by the dashed line, is collapsed. Without the aid of a stent or luminal filler, the anastomosis of a vessel of such caliber is extremely difficult. Using a 2% w/v APC1 hydrogel formed in a syringe, an intraluminal injection was performed on both severed ends of the vessel. The visible distention of the lumen is shown in FIG. 8C and the corresponding cross-section OCT image in FIG. 8D. The OCT image visually demonstrates the ability of the hydrogel to mechanically support the vessel wall after injection. FIG. 8E shows a longitudinal cross-section OCT image of the proximal (left) and distal (right) ends of the vessels after injection with the APC1 hydrogel, with the vessel lumen indicated by the dashed lines. The APC1 hydrogel not only caused vascular distension that facilitates easier identification of a single vessel wall through which a suture can be placed, but helped maintain a cylindrical vessel shape, which lead to more uniform suture spacing and vessel closure.

Figure 8F:
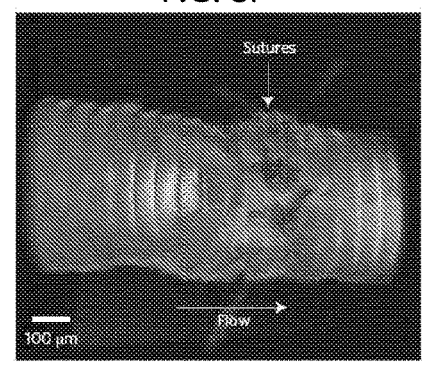
Figure 8G:
Figure 24:
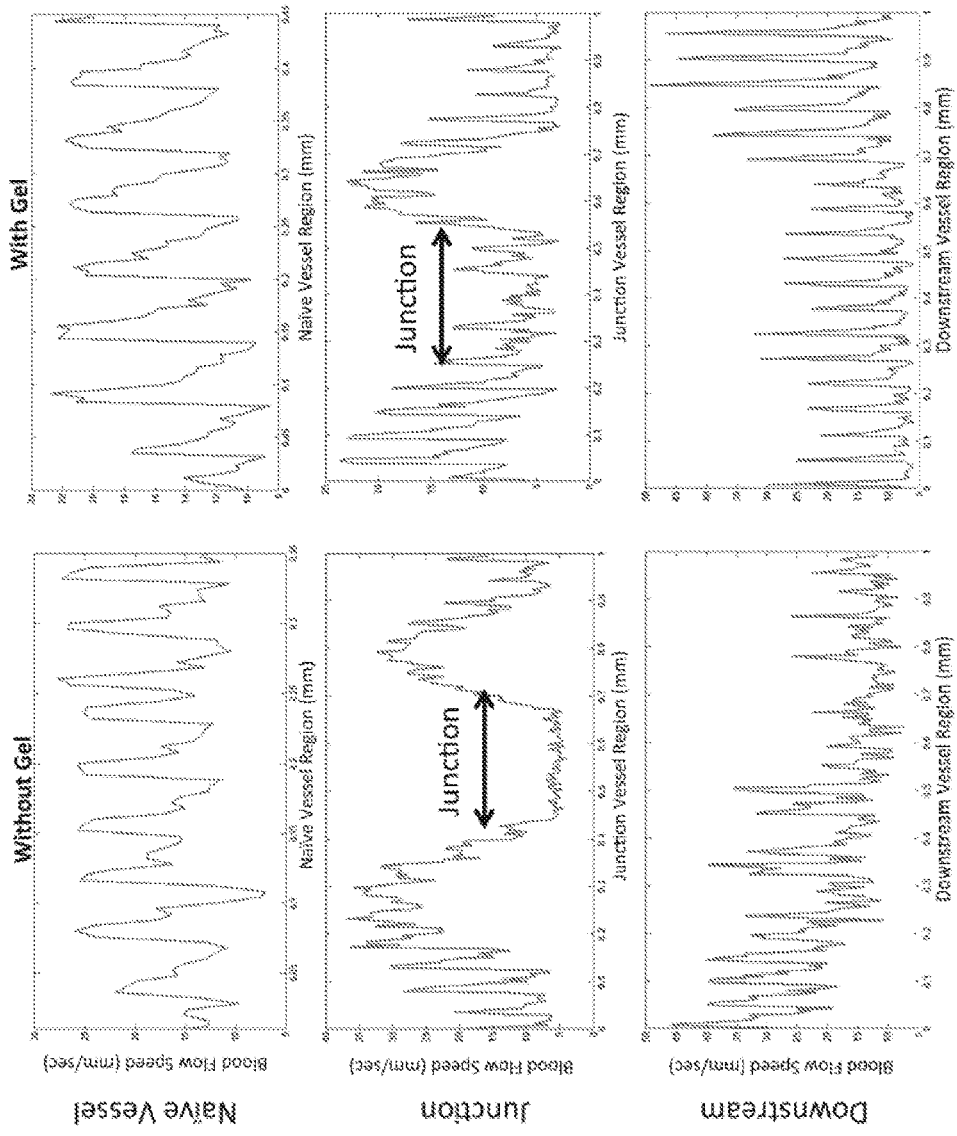
FIG. 24 shows phase-resolved Doppler optical coherence tomography was utilized to determine quantitative blood flow speed for mice receiving femoral artery anastomosis. Left column shows average artery blood flow speed measured in a vessel anastomosed without gel and right column shows vessel anastomosed with the APC1 gel. In each column, naïve vessels are compared to the junction (anastomosis) site, as well as the downstream vessel portion. The blood flow speed was calculated with a single Doppler angle deduced from the structure images and covers a range of 1 mm of the vessel. Normal flow speed was demonstrated for both conditions. Variations in blood flow speed between animals (e.g. comparing the left and right columns) is a result of local Doppler angle nonuniformity.

Furthermore, the hydrogel can be applied between the vessels, aiding their approximation. Vessel ends can be inserted into the gel, where local thinning occurs proximal to the vessels during their movement within the gel. Once the vessels are approximated, the gel recovers instantaneously, gently fixing them. This allows optimal placement of the vessel ends for suture placement. Additionally, the needle can be passed directly through the optically clear gel to place the sutures; local thinning and recovery occurs around the needle during its movement through the gel. On placement of the final suture, the external gel is washed away and the vessel is irradiated at the suture site for 2 min using ultraviolet light from a hand-held 365 nm light emitting diode to remove the interior gel. Resumption of blood flow after removing the clamps clears the disrupted gel, as demonstrated by volume Doppler OCT (FIG. 8F) and blood flow speed measurements (FIG. 24). Blood flow was also confirmed visually (FIG. 8G). Upon placement of the final suture and completion of the anastomosis, the vessel was irradiated at the suture site for 2 minutes using a hand-held 365 nm LED UV light before the vessel clamps were removed. Successful disruption of the gel and resumption of blood flow is evidenced by the Volume Doppler OCT image in FIG. 8F, where the lighter regions indicate uncompromised blood flow through the suture site. In addition, visual conformation of blood flow through the site of the anastomosis is clearly shown in FIG. 8G.

Figure 9A:
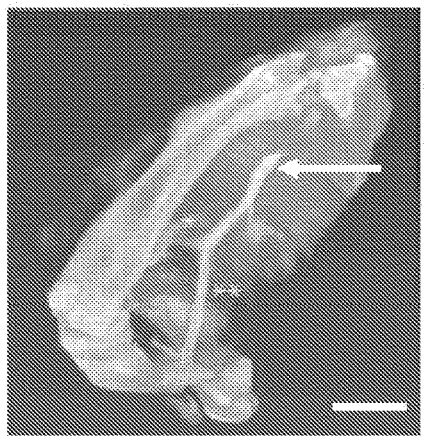
FIGS. 9A-9I show perfusion of mouse lower limb after hydrogel-supported end-to-end anastomosis of the femoral artery.
Figure 9B:
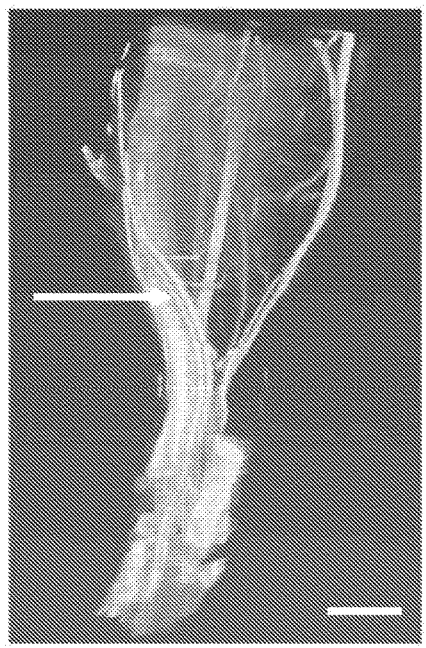
Figure 9C:
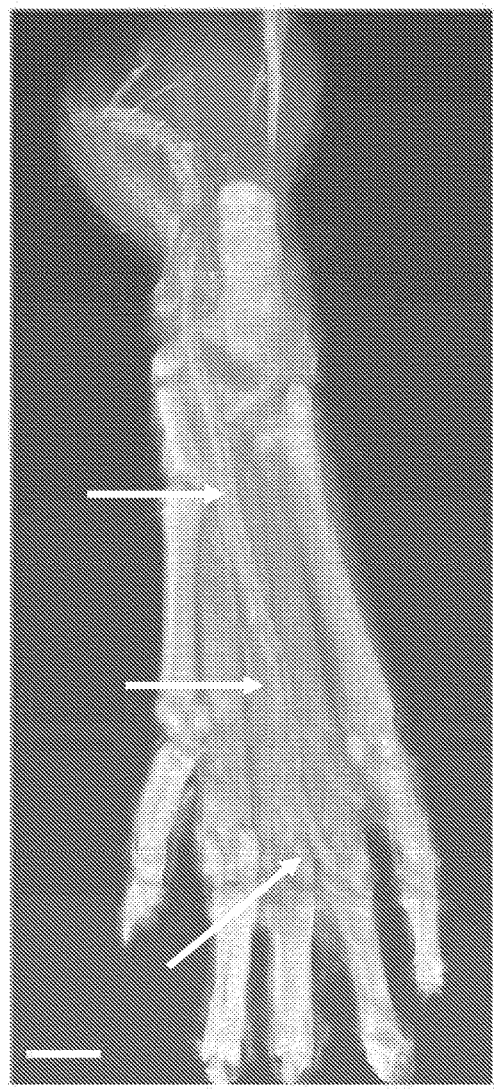
Figure 9D:
Figure 9G:
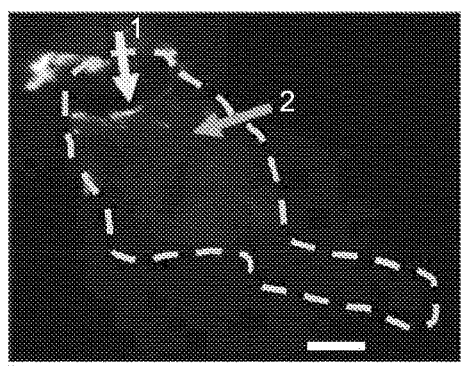
Figure 9E:
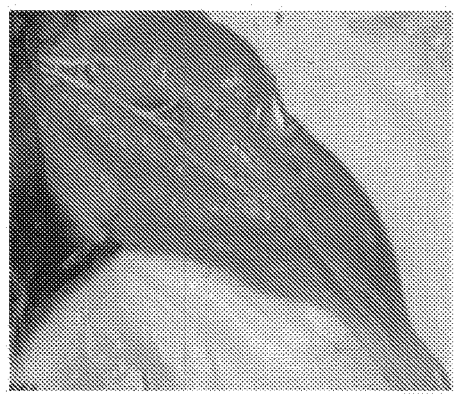
Figure 9H:
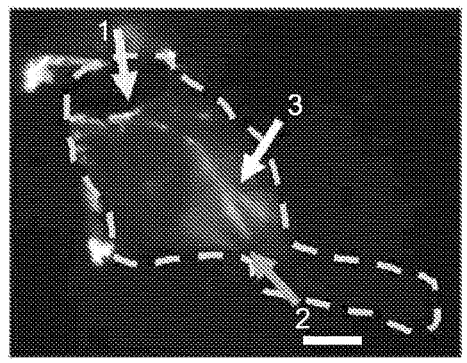
Figure 9F:
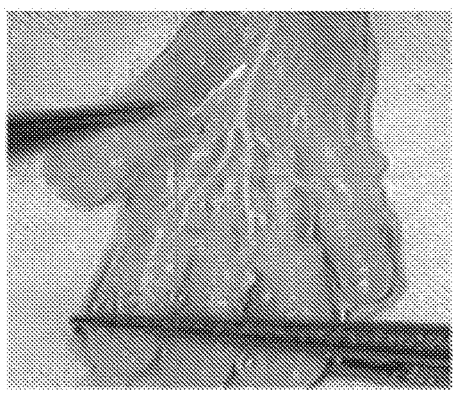
Figure 9I:
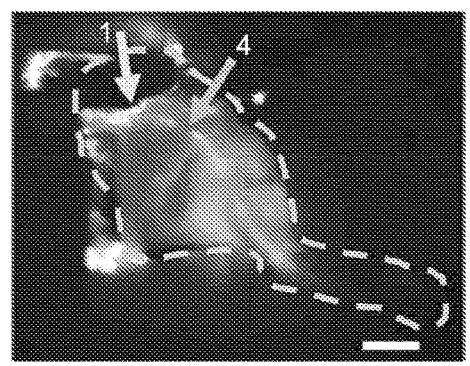

The efficacy of the final gel-sol phase transition is critical, as any remaining solid material could lead to thrombus formation, diminished perfusion and tissue ischaemia. Thus, vessel patency was assessed in a series of experiments that monitor vascular perfusion. High-resolution micro-computed tomography (CT) was used to follow the perfusion of a polymeric contrast agent (microfil) 1 h after gel-based end-to-end anastomosis of the femoral artery and resumption of blood flow. FIGS. 9A-9C show that the polymer completely fills the distal tibial and fibular vessels as well as the plantar arch on the footpad and the digital branches to the toes. Separate experiments in which animals were dissected to directly observe polymer distribution support the CT data (FIGS. 9D-9F), confirming occlusion-free vascular patency throughout the entire extremity, which is similar to the contralateral control limb. Finally, perfusion of a near-infrared dye was followed throughout an explanted hind limb after irradiating a gel that had been implanted into the femoral artery (FIG. 9G-9I). The leading edge of the dye (arrow 2) immediately penetrates the limb from its initial injection site (arrow 1), quickly penetrating another major vessel (arrow 3, FIG. 9H) and distant vascular regions and surrounding tissue (FIG. 9I).

Figure 25:
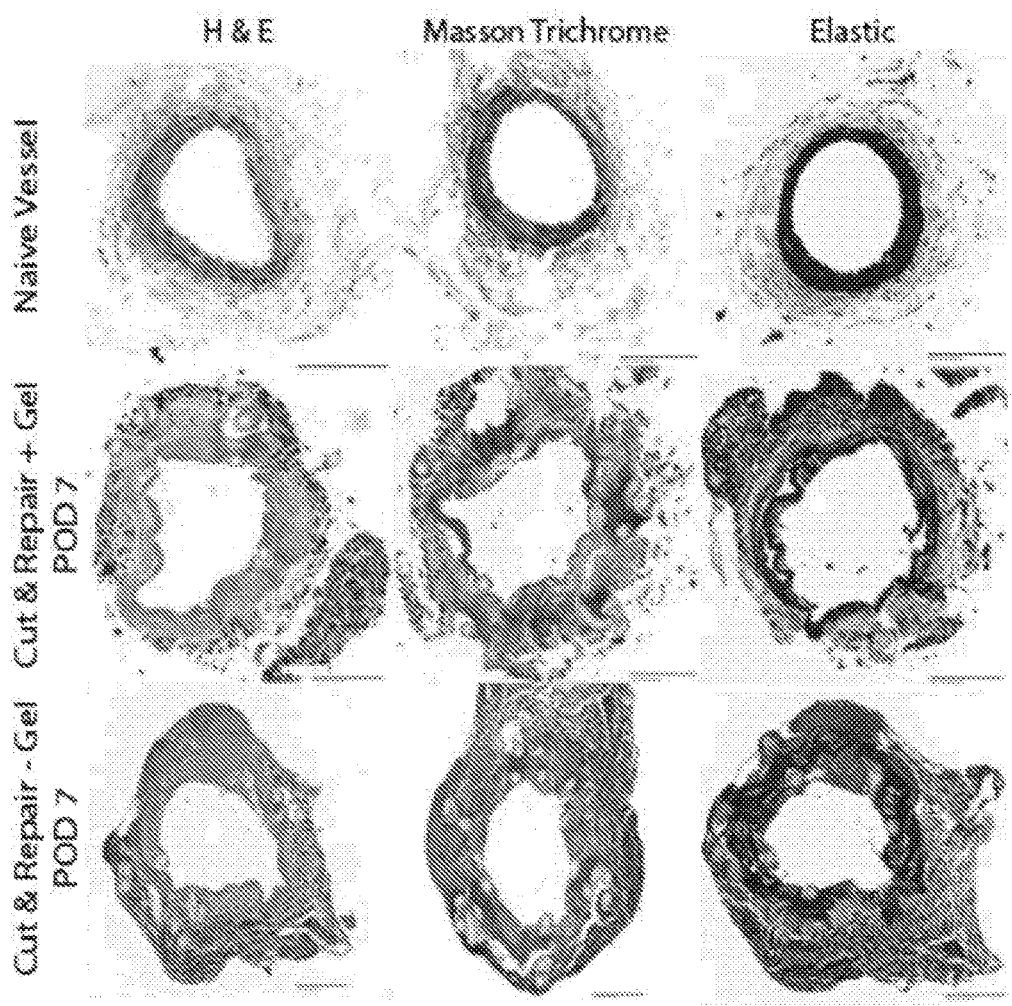
FIG. 25 shows histological images of anastomosed vessels 7 days post-surgery. Cross sections of mouse femoral arteries at the site of anastomosis (n=3, representative image of 1 animal). H&E, Masson Trichrome and Elastic stains were performed on naïve untreated control vessels, as well as samples obtained on post-operative day 7 after anastomosis performed with and without the APC1 hydrogel. Compared to naïve vessels a peri-vascular inflammatory response can be appreciated in both anastomosis conditions as a result of the surgical tissue traumatization and the post-operative physiologic healing process. However, the vascular lumen is free of remnants of the APC1 hydrogel comparable to the experiments without gel. No thrombus or endothelial inflammatory response is present indicating that the APC1 hydrogel has been completely dissolved. Scale bar=100 micron.
Figure 26:
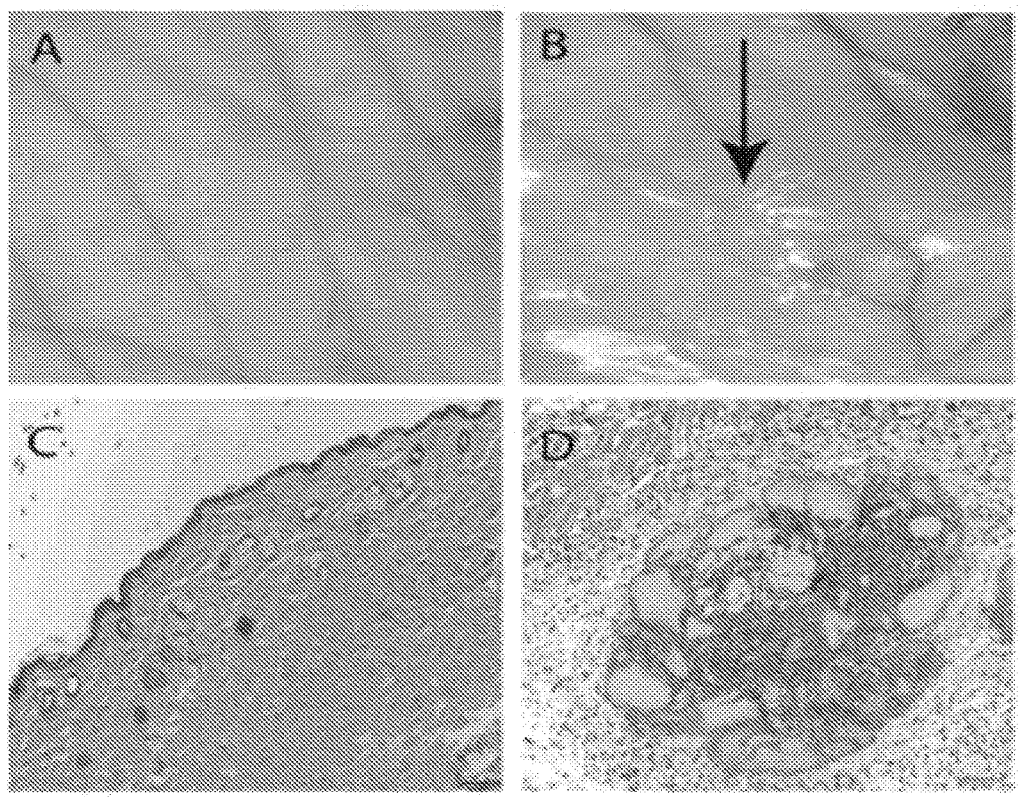
FIG. 26 shows histological evaluation of tissue surrounding subcutaneously implant site. Panel A and B show macroscopic images of the injection sites after either saline (A) or APC1 hydrogel (B, arrow head) application (50 μL) into the subcutaneous space of the lateral thoracic wall of mice (n=3, representative image of 1 animal) with no clinical signs of local inflammation. Panel C and D represent H&E stained histological cross sections of the skin and subcutaneous tissue from the local injection sites shown in A & B. While C shows no evidence of inflammatory cell infiltrates at the site of saline injection D shows APC1 hydrogel remnants with a surrounding of nucleated cells representative of a foreign body reaction. Ongoing degradation of the APC1 hydrogel can be appreciated by the fractioned gel components at 7 days post injection.

Taken together, the data in FIGS. 8 and 9 show that the APC1 gel can be syringe-injected into the collapsed lumina of vessels to re-establish their shape, and aid in their anastomosis. Importantly, subsequent photolysis of the gel results in the disruption of the material and, with the aid of shear from the flow of blood, can effect a gel-sol phase transition that allows the passage and perfusion of blood. The peripheral vascular and capillary bed was well perfused, without any evidence of luminal narrowing or occlusion due to gel remnants. The gel biocompatibility was also investigated, and histology revealed a similar peri-vascular inflammatory response in vessels anastomosed with or without gel, a result of surgical tissue traumatization and post-operative healing (FIG. 25). Furthermore, subcutaneously injected gel produced no gross local inflammation and a typical foreign body response that resolved (FIG. 26).

Conclusions

The de novo design of a new class of β-hairpin peptides containing 4-methoxy-7-nitroindolinyl glutamic acid within the hydrophobic regions of the peptide amphiphiles APC1 and APC2 led to the development of hydrogel materials capable of multiple phase transitions. Mechanical characterization of these hydrogel materials using rheology indicated that the APC1 hydrogel more closely satisfied the requirements for use as an intraluminal stent to aid in microvascular anastomosis due to its ability to quickly form a hydrogel, be shear-thinned and re-heal, and to undergo a rapid gel-sol phase transition through UV light-triggered disruption of the hydrogel network. The utility of the hydrogel's multiple phase transitions were demonstrated in mouse models of micro-scale anastomosis, specifically of the femoral artery. The APC1 gel can be formed directly in a syringe. Subsequent syringe injection of the gel into the collapsed lumina of vessels re-establishes vessel shape, provides mechanical support to the blood vessel walls, stents the vessel lumen, and more easily facilitates uniform and precise suturing. Post-surgical irradiation of the hydrogel within the vessel sufficiently disrupted the material, allowing blood to flow through the site of the anastomosis and throughout the distal limb vasculature. Thus, peptide design can afford a self-assembled material that represents a promising alternative to currently available non-injectable stents.

Materials and General Methods

All reagents and solvents were used as received. All Fmoc-protected amino acids were purchased from Novabiochem. PL-rink amide resin was purchased from Polymer Laboratories. 1-H-benzotriazolium-1-[bis(dimethylamino) methylene]-5-chloro-hexafluorophosphate-(1-),3-oxide (HCTU) was obtained from Peptides International. Trifluoroacetic acid and triisopropylsilane were obtained from Acros Organics. Diethyl ether was purchased from Fisher Scientific. Unless otherwise stated, all other reagents were purchased from Sigma Aldrich. $^1$H and $^{13}$C NMR chemical shifts were recorded on a Varian spectrometer and are reported in ppm and were assigned based on $^1$H-$^1$H COSY and $^1$H-$^{13}$C HMQC experiments. Nominal mass spectra for small molecules were obtained using electrospray ionization (ESI). Liquid chromatography mass spectroscopy of peptides was performed using a linear gradient of 0-90% MeCN containing 0.1% TFA in water containing 0.1% TFA over 40 minutes on C18 stationary phase coupled with an electrospray ionization (ESI) detector. Molecular models for FIG. 2B were prepared in Discovery Studio 4.0 (Accelrys/BioVia). Peptides were pre-organized in a canonical β-hairpin conformation containing a type II' β-turn. Eight hairpins were manually docked to form a bilayer, each layer consisting of four peptides. Assemblies were energy minimized employing a CHARMm forcefield and implicit generalized Borne water. A two-step protocol was employed for the minimization. First, all backbone atoms were constrained and the side chain atoms minimized using a steepest decent algorithm. This was followed by an all atom minimization using steepest decent with an RMS gradient tolerance of 3, followed by a conjugate gradient algorithm. All animal studies were performed using male C57BL/6 mice at 8-10 weeks of age.

Peptide Synthesis and Purification: Peptides were synthesized on PL-Rink amide resin using an automated ABI 433A peptide synthesizer (Applied Biosystems, Calif.) and a Tribute peptide synthesizer (Protein Technologies, Inc., Ariz.). Synthesis was carried out via solid-phase Fmoc-based chemistry with HCTU activation. Fmoc-L-Glu(MNI)-OH was incorporated into peptides by reacting the peptide on resin with a solution of 3 eqv. of amino acid, 2.7 eqv. of HCTU, and 6 eqv. of diisopropylethylamine in NMP (3.75 mL) for 30 mins. Dried resin-bound peptides were cleaved from the resin and side-chain deprotected by a trifluoroacetic acid: triisopropylsilane: deionized water (95:2.5:2.5) cocktail for 2 h under argon atmosphere. Crude peptides were precipitated using cold ethyl ether and then lyophilized. The resulting crude APC1 and APC2 peptides were purified by RP-HPLC (Vydac C18 Column) at 40° C. using an isocratic gradient from 0-2 minutes at 0% standard B, then utilizing a linear gradient from 0-20% standard B for 6 minutes followed by a gradient of 20-100% standard B over 160 minutes. Here, standard A is 0.1% TFA in water and standard B is 90% MeCN, 9.9% $H_2O$, and 0.1% TFA. Both peptides elute at 33 minutes. Control peptides cAPC1 and cAPC2 were also purified by RP-HPLC (Vydac C18 Column) at 40° C. using an isocratic gradient from 0-2 minutes at 0% standard B, then utilizing a linear gradient from 0-16% standard B for 4 minutes followed by a gradient of 16-100% standard B over 168 minutes. Both peptides elute at 28 minutes. Purified peptide solutions were lyophilized, resulting in pure peptide powders that were utilized in all assays. Purity of each peptide was confirmed by analytical HPLC and positive mode electrospray ionization—mass spectrometry. Fmoc-Glu(MNI)-OH (7) was prepared by a modified procedure as outlined below (Papageorgiou, et al., J Organic Chemistry 2004, 69 (21), 7228-7233; Huang, et al, Biochemistry 2005, 44 (9), 3316-3326). NMR spectra for 7 and the intermediates of its synthesis are provided on pages S17-S28. Claycop was prepared in a 2:3 ratio of $Cu(NO_3)_2$ and montmorillonite K10 as described previously (Laszlo, et al., Aldrichimica Acta 1988, 21 (4), 97-103).

Figure 10:
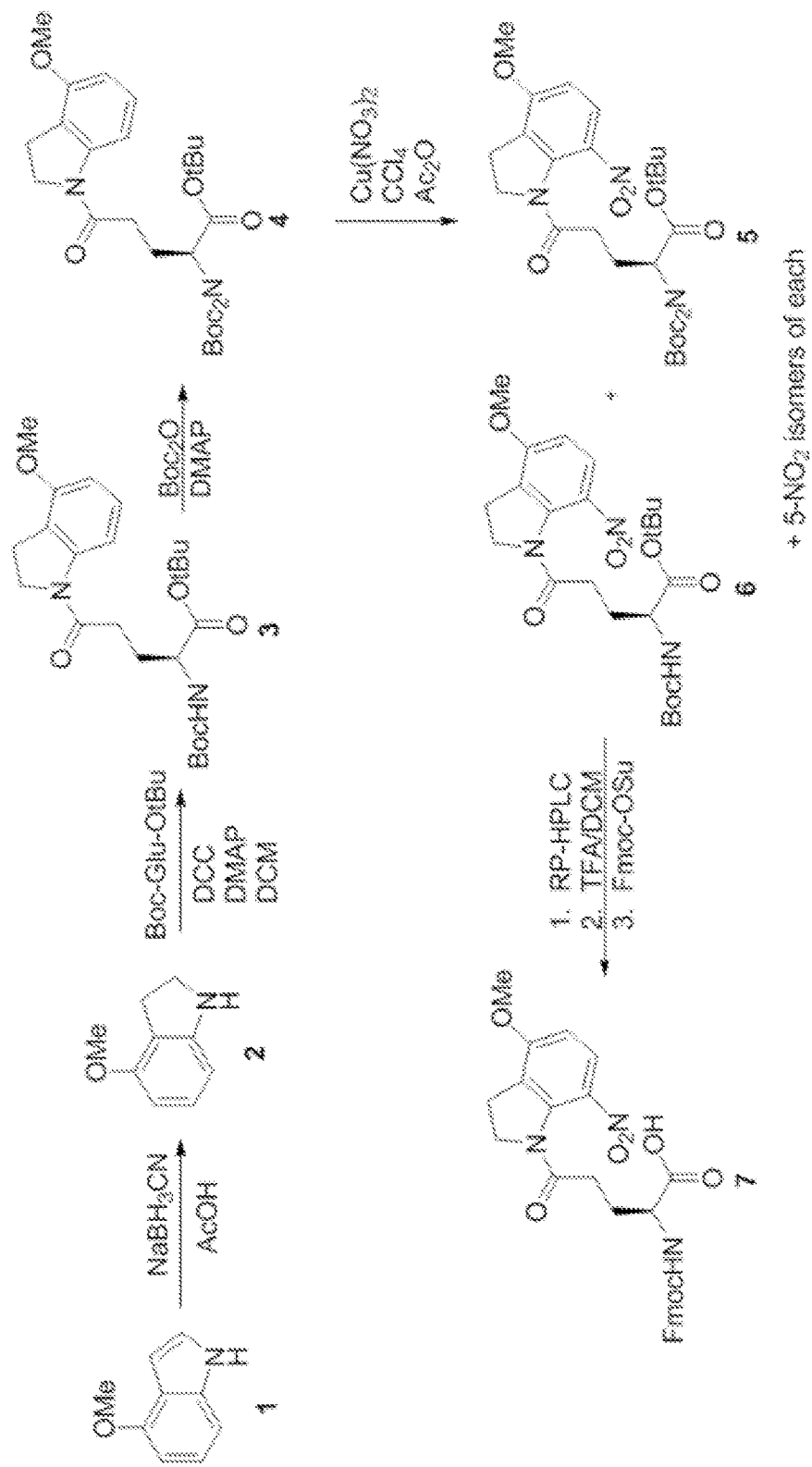
FIG. 10 shows a scheme for the synthesis of Fmoc-Glu (MNI)-OH.
Figure 11A:
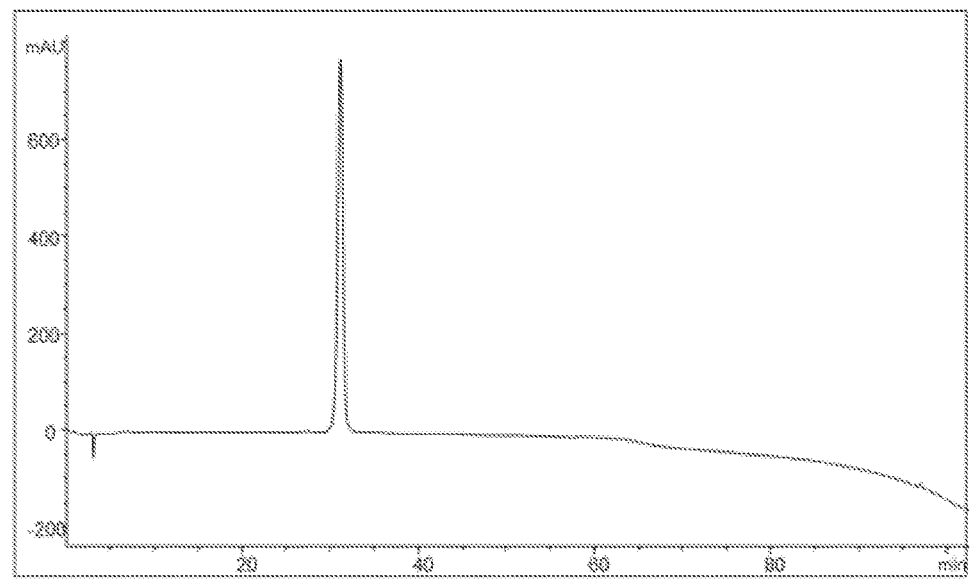
FIGS. 11A-11D show HPLC analysis of the APC1 and APC2 peptides. (A) HPLC of APC1. (B) Mass spectrum of APC1 with calculated m/z. (C) HPLC of APC2. (D) Mass spectrum of APC2 with calculated m/z.
Figure 11B:
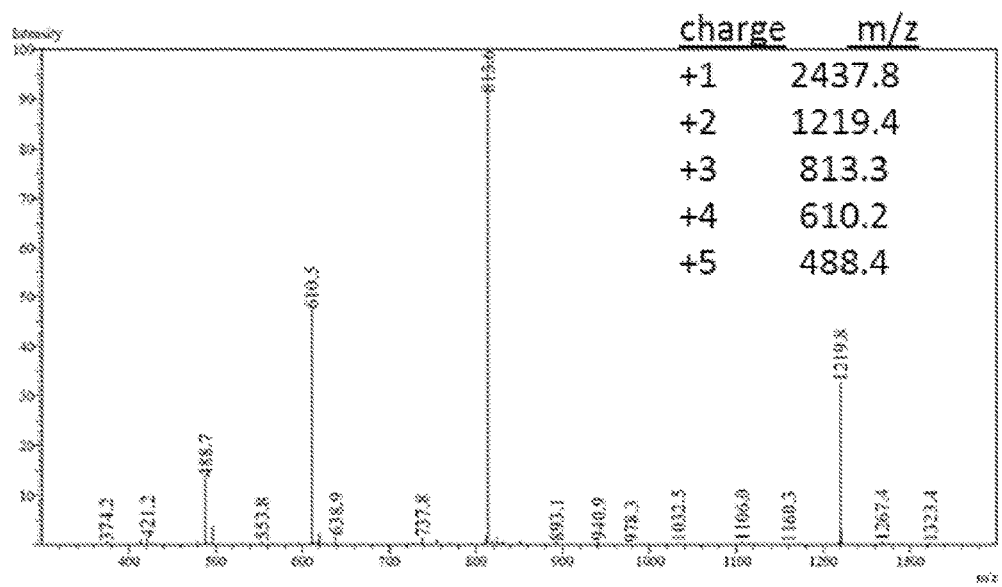
Figure 11C:
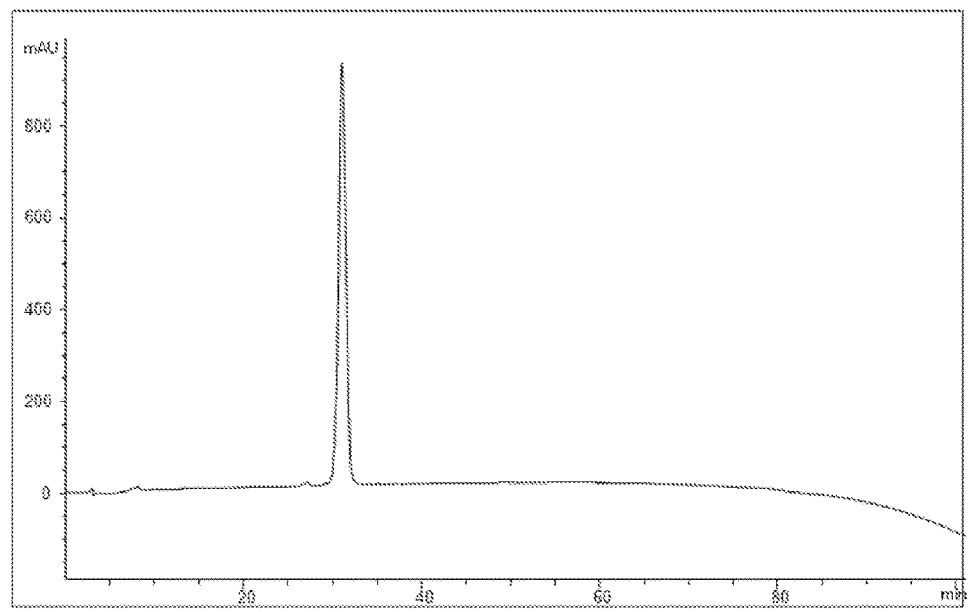
Figure 11D:
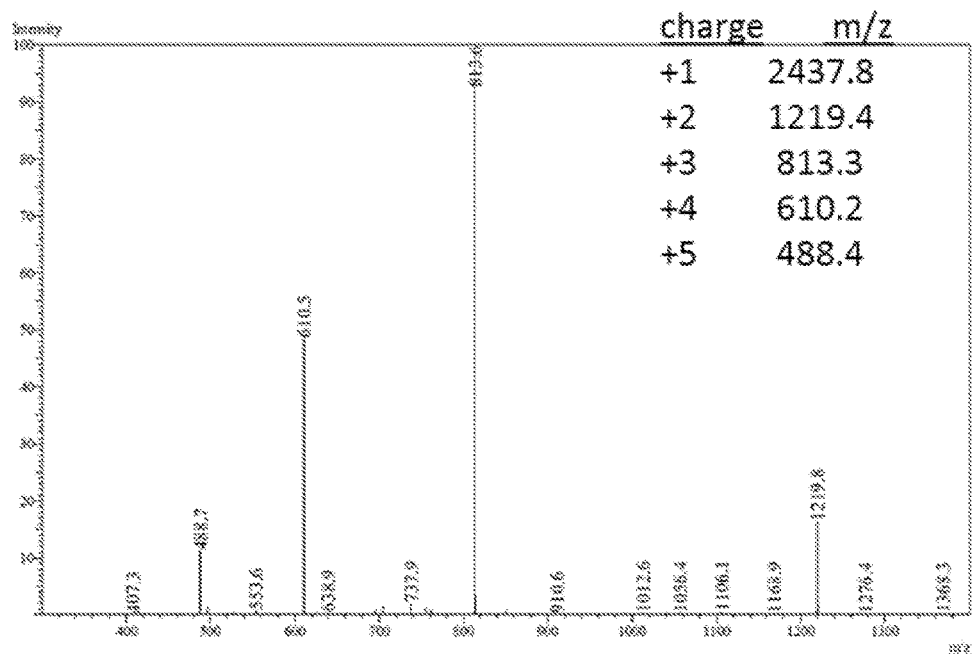
Figure 12A:
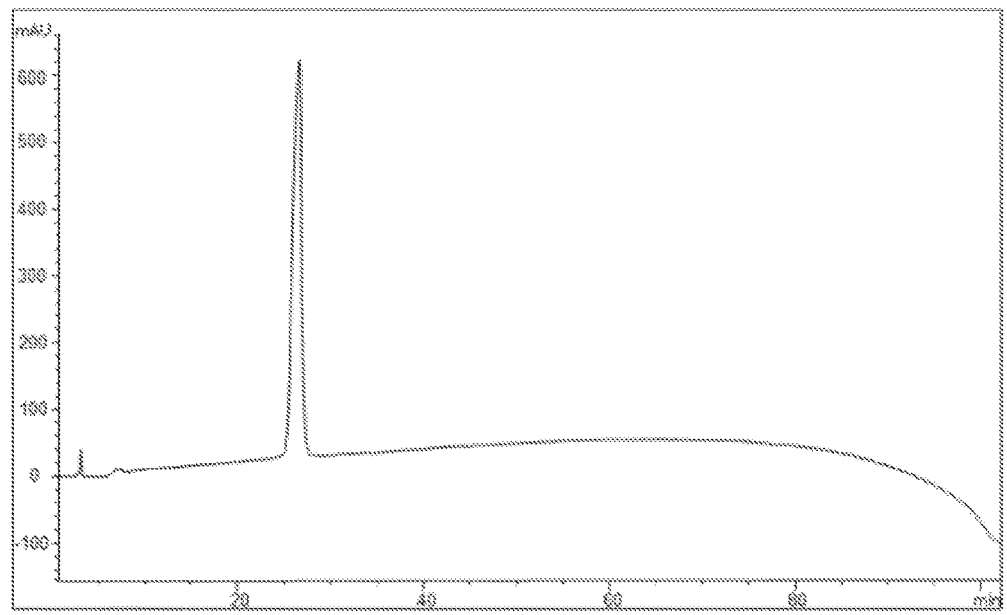
FIGS. 12A-12D show HPLC analysis of the cAPC1 and cAPC2 peptides. (A) HPLC of cAPC1. (B) Mass spectrum of cAPC1 with calculated m/z. (C) HPLC of cAPC2. (D) Mass spectrum of cAPC2 with calculated m/z.
Figure 12B:
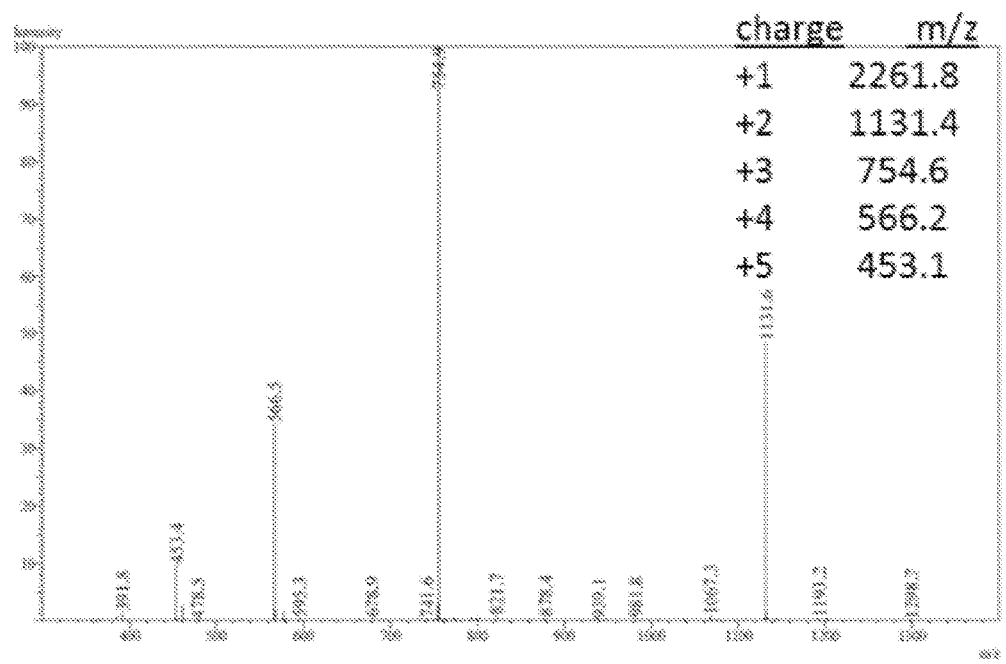
Figure 12C:
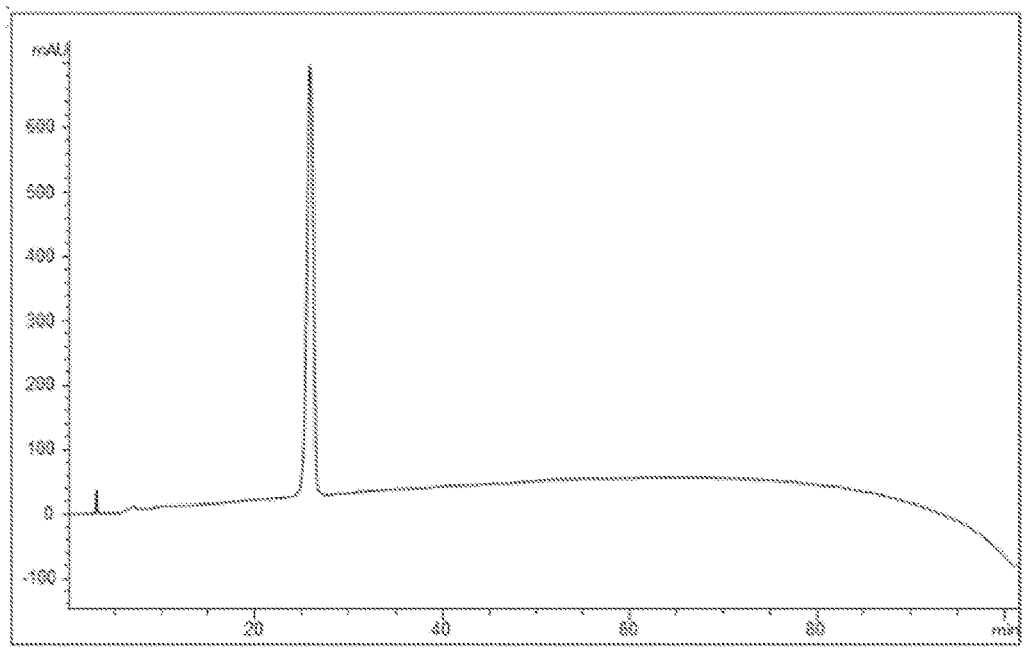
Figure 12D:
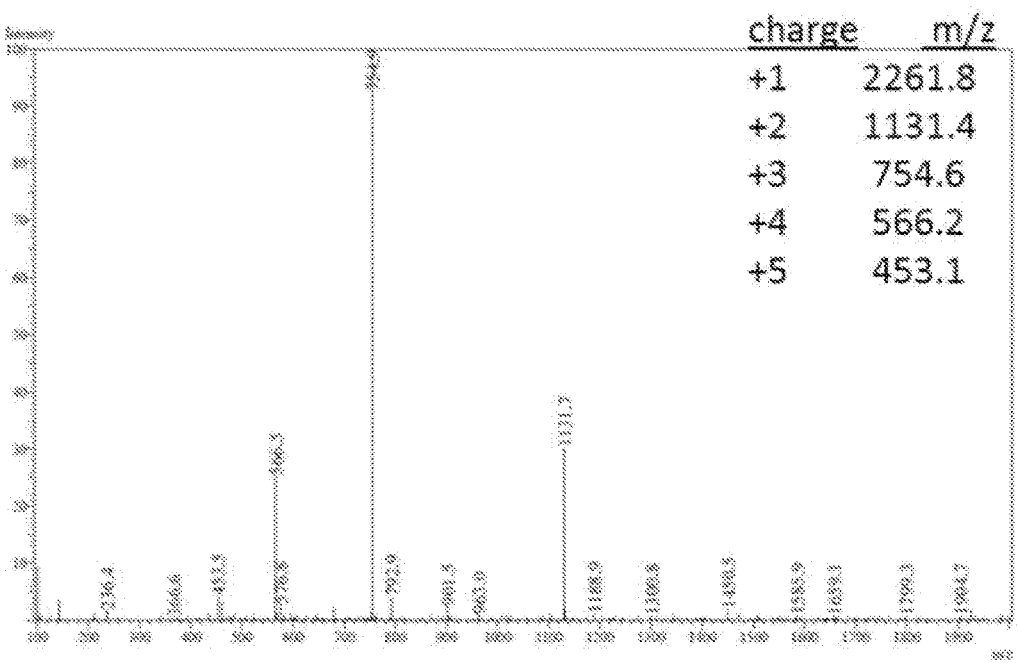
Figure 13:
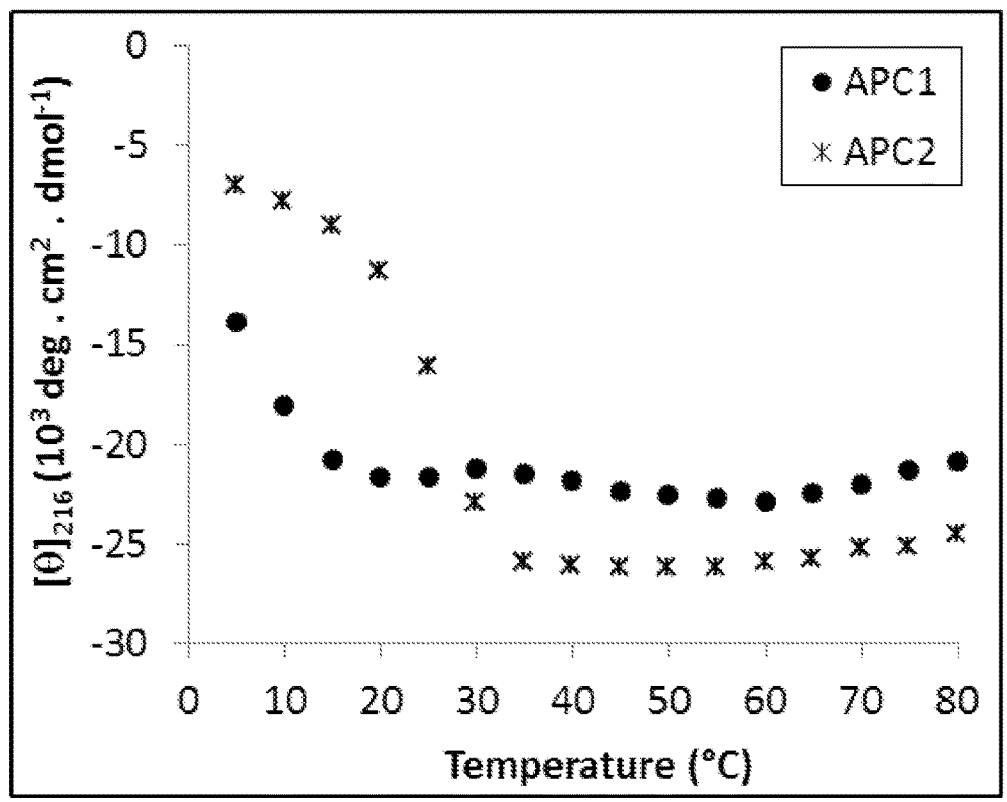
FIG. 13 illustrates the temperature-dependent β-sheet formation for 1% w/v APC1 and APC2 hydrogels at pH 7.4, monitoring the mean residue elipticity [θ] at 216 nm.
Figure 14A:
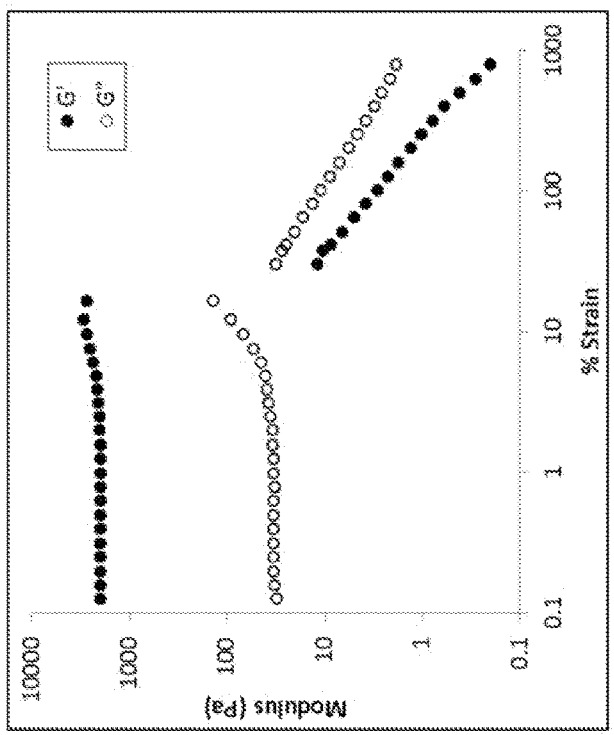
FIGS. 14A-14B show characteristics of hydrogels including the APC1 peptide. (A) Dynamic frequency sweep of 1% w/v APC1 (pH 7.4, 25° C.) at 0.2% strain. (B) Dynamic strain sweep of 1% w/v APC1 at a frequency of 6 rad/s.
Figure 14B:
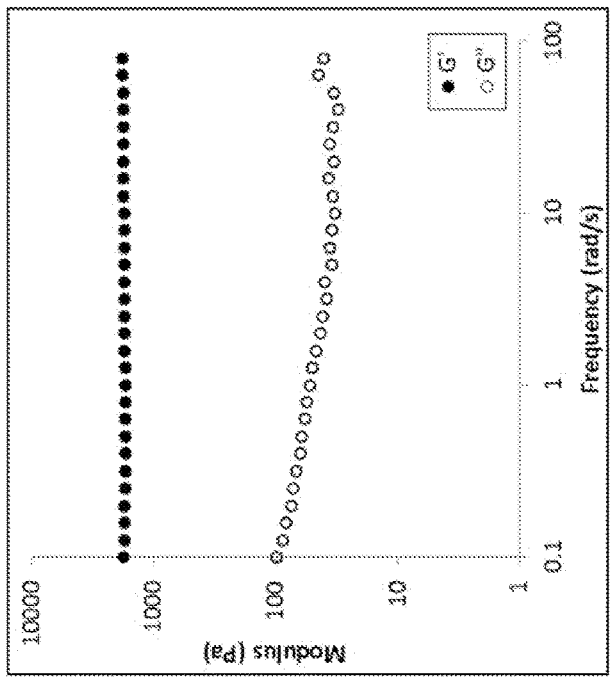
Figure 15A:
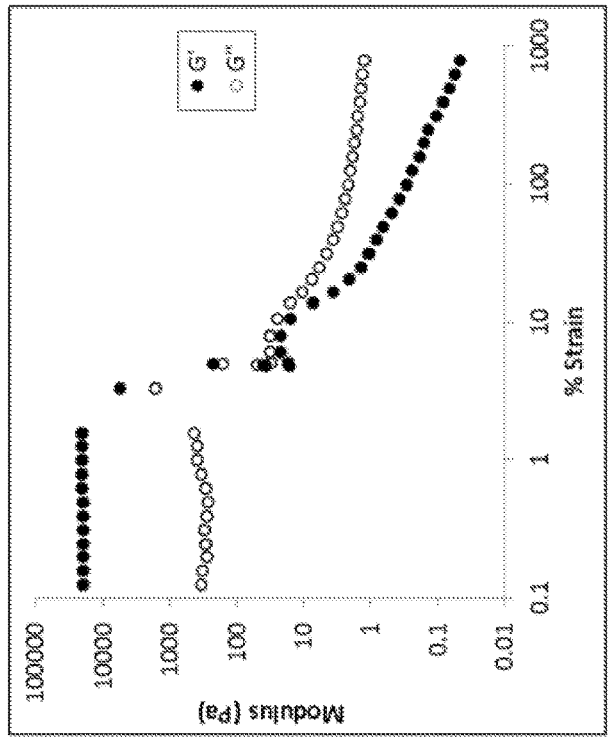
FIGS. 15A-15B show characteristics of hydrogels including the APC2 peptide. (A) Dynamic frequency sweep of 1% w/v APC2 (pH 7.4, 37° C.) at 0.2% strain. (B) Dynamic strain sweep of 1% w/v APC2 at a frequency of 6 rad/s.
Figure 15B:
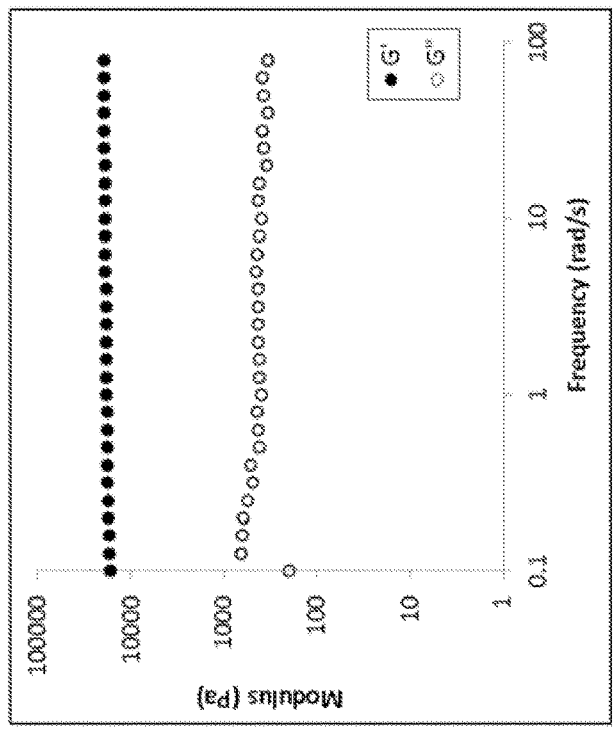

Synthesis of Fmoc-Glu(MNI)-OH. The general synthesis scheme is illustrated in FIG. 10. Additional description is provided below:

4-Methoxyindoline (2). Sodium cyanoborohydride (2.29 g, 36.5 mmol) was added portionwise over 20 minutes to a stirring solution of 4-methoxyindole (1.47 g, 10 mmol) in AcOH (30 mL). After the addition, the reaction was stirred for 30 minutes, water (30 mL) was added, and the solvent was removed in vacuo. The residue was neutralized by the addition of 1M $NaHCO_3$ and extracted 2×50 mL with EtOAc. The combined organic extracts were washed with 0.5M NaOH (30 mL), dried with $MgSO_4$, and concentrated in vacuo to yield 1.43 g of crude 2 (9.6 mmol, 96%) as an oil, which was used without any further purification. $^1H$ NMR (400 MHz, $CDCl_3$): δ=7.00 (t, J=8.0 Hz, 1H, ArH-4), 6.33 (d, J=7.8 Hz, 1H, ArH-3), 6.30 (d, J=8.2 Hz, 1H, ArH-5), 3.82 (s, 3H, $CH_3$-9), 3.57 (t, 2H, $CH_2$-8), 2.99 (t, 2H, $CH_2$-7). $^{13}C$ NMR (101 MHz, $CDCl_3$): δ=156.6 (6), 153.4 (2), 128.7 (4), 115.9 (1), 103.3 (3), 101.7 (5), 55.4 (9), 47.6 (8), 27.0 (7). ESI-MS calcd for $C_9H_{11}NO$ ($MH^+$) 150.1, found 150.1.

4-Methoxyindolinyl N-α-(tert-butoxycarbonyl)-L-glutamic acid α-tert-butyl ester (3). To a stirring solution of crude 2 (1.89 g, 12.7 mmol) in $CH_2Cl_2$ (98 mL) was added N-α-(tert-butoxycarbonyl)-L-glutamic acid α-tert-butyl ester (5.0 g, 16.5 mmol), followed by N,N'-dicyclohexylcarbodiimide (3.40 g, 16.5 mmol) and DMAP (2.01 g, 16.5 mmol). The mixture was stirred at room temperature for 20 h, after which time the precipitated urea was filtered and washed with $CH_2Cl_2$. The filtrate was washed with 1M $NaHCO_3$ (50 mL), 0.5M HCl (100 mL), brine (50 mL), dried with $MgSO_4$, concentrated, and purified on silica gel using an automated flash chromatography system employing a gradient of ethyl acetate in hexanes; product elutes at ~40% ethyl acetate to yield 5.3 g of 3 (12.2 mmol, 96%) as a light yellow foam. $[α]_D^{20}=+8.0°$ (c 1.0, $CDCl_3$); $^1H$ NMR (400 MHz, $CDCl_3$): δ=7.83 (d, J=8.1 Hz, 1H, ArH-16), 7.16 (t, J=8.2 Hz, 1H, ArH-17), 6.57 (d, J=8.2 Hz, 1H, ArH-18), 5.23 (d, 1H, NH-1), 4.27-4.16 (m, 1H, CH-2), 4.03 (t, 2H, $CH_{2-15}$), 3.83 (s, 3H, $CH_3$-20), 3.09 (t, 2H, $CH_{2-14}$), 2.59-2.39 (m, 2H, $CH_{2-10}$), 2.31-2.21 (m, 1H, CHH-9), 2.06-1.98 (m, 1H, CHH-9'), 1.47 (s, 9H, $C(CH_3)_3$-8), 1.42 (s, 9H, $C(CH_3)_3$-5). $^{13}C$ NMR (101 MHz, $CDCl_3$): δ=171.7 (11), 170.3 (3), 155.8 (6), 155.7 (19), 144.4 (12), 129.1 (17), 118.4 (13), 110.2 (16), 106.1 (18), 82.2 (4), 79.8 (7), 55.4 (20), 53.9 (2), 48.5 (15), 32.4 (10), 28.4 (5), 28.1 (8), 27.9 (9), 25.2 (14). ESI-MS calcd for $C_{23}H_{34}N_2O_6$ ($MH^+$) 435.3, found 435.3.

4-Methoxyindolinyl N-α-(di-tert-butoxycarbonyl)-L-glutamic acid α-tert-butyl ester (4). To a solution of 3 (869 mg, 2 mmol) in $CH_2Cl_2$ (8 mL) and triethylamine (12 mL) was added $Boc_2O$ (1.09 g, 5 mmol) and DMAP (29.3 mg, 0.24 mmol). The solution was heated at reflux for 5 h, after which additional $Boc_2O$ (550 mg, 2.5 mmol) was added and the reaction was stirred overnight at room temperature. After removing the solvent in vacuo, the residue was dissolved in ethyl acetate (40 mL), washed with 1M $KHSO_4$ (25 mL), 1M $NaHCO_3$ (25 mL), brine (25 mL), dried with $MgSO_4$, concentrated, and purified on silica gel using and automated flash chromatography system employing a gradient of ethyl acetate in hexanes; product elutes at ~30% ethyl acetate to yield 913 mg of 4 (1.7 mmol, 85%) as a light yellow foam. $[α]_D^{20}=-32.0°$ (c 1.0, $CDCl_3$); $^1H$ NMR (400 MHz, $CDCl_3$): δ=7.86 (d, J=8.1 Hz, 1H, ArH-18), 7.15 (t, J=8.2 Hz, 1H, ArH-19), 6.56 (d, J=8.1 Hz, 1H, ArH-20), 4.87 (dd, 1H, CH-7), 4.05 (t, 2H, $CH_{2-17}$), 3.83 (s, 3H, $CH_3$-22), 3.09 (t, 2H, $CH_{2-16}$), 2.62-2.37 (m, 3H, $CH_{2-12}$, CHH-11), 2.27-2.15 (m, 1H, CHH-11'), 1.48 (s, 18H, $C(CH_3)_3$-3, $C(CH_3)_3$-6), 1.45 (s, 9H, $C(CH_3)_3$-10). $^{13}C$ NMR (101 MHz, $CDCl_3$): δ=170.3 (13), 169.5 (8), 155.7 (21), 152.4 (4, 1), 144.5 (14), 129.0 (19), 118.3 (15), 110.2 (18), 105.9 (20), 83.0 (9), 81.4 (5, 2), 58.5 (7), 55.4 (22), 48.5 (17), 32.7 (12), 28.1 (10, 6, 3), 25.1 (16), 24.6 (11). ESI-MS calcd for $C_{28}H_{42}N_2O_8$ ($MH^+$) 535.3, found 535.4.

Nitration of 4 Using Claycop. To a solution of 4 (4.5 g, 8.46 mmol) in $CCl_4$ (35 mL) and $Ac_2O$ (18 mL) was added Claycop 10/15 (5.41 g). The mixture was stirred for 2 h, after which the reaction was filtered over celite and the solid washed with $CH_2Cl_2$. The filtrate was evaporate in vacuo and the residue was dissolved in ethyl acetate (80 mL), washed with 1M $NaHCO_3$ (50 mL), brine (50 mL), dried with $MgSO_4$, and concentrated in vacuo to give a crude mixture of 7-nitro and 5-nitro isomers of 5 and the mono- Boc decomposition product 6. The mixture was purified by reverse-phase chromatography using a gradient of $CH_3CN$ in $H_2O$ containing 0.1% TFA, and fractions of 5 and 6 containing the major regioisomer (7-nitro) were isolated for characterization. Fractions of 5 contained a varying amount of compound 6 due to post-purification decomposition.

4-Methoxy-7-nitroindolinyl N-α-(di-tert-butoxycarbonyl)-L-glutamic acid α-tert-butyl ester (5). $^1$H NMR (400 MHz, $CDCl_3$): δ=7.73 (d, J=9.0 Hz, 1H, ArH-19), 6.63 (d, J=9.1 Hz, 1H, ArH-20), 4.77 (dd, 1H, CH-7), 4.22 (t, 2H, $CH_2$-17), 3.90 (s, 3H, $CH_3$-22), 3.06 (t, 2H, $CH_2$-16), 2.71-2.46 (m, 3H, CHH-11, $CH_2$-12), 2.23-2.13 (m, 1H, CHH-11'), 1.48 (s, 18H, $C(CH_3)_3$-3, $C(CH_3)_3$-6), 1.44 (s, 9H, $C(CH_3)_3$-10). $^{13}$C NMR (101 MHz, $CDCl_3$): δ=170.8 (13), 169.3 (8), 158.9 (21), 152.5 (4, 1), 136.8 (14), 135.4 (18), 125.5 (19), 122.9 (15), 106.3 (20), 83.4 (9), 81.7 (5, 2), 58.5 (7), 56.1 (22), 50.1 (17), 32.6 (12), 28.1 (10, 6, 3), 26.4 (16), 25.1 (11). ESI-MS calcd for $C_{28}H_{41}N_3O_{10}Na$ (M+Na) 602.3, found 602.4.

4-Methoxy-7-nitroindolinyl N-α-(tert-butoxycarbonyl)-L-glutamic acid α-tert-butyl ester (6). $[α]_D^{20}$=−16.9° (c 1.0, $CDCl_3$); $^1$H NMR (400 MHz, $CDCl_3$): δ=7.75 (d, J=9.0 Hz, 1H, ArH-17), 6.64 (d, J=9.1 Hz, 1H, ArH-18), 5.18 (d, 1H, NH-1), 4.27-4.12 (m, 3H, CH-2, $CH_2$-15), 3.91 (s, 3H, $CH_3$-20), 3.08 (t, 2H, $CH_2$-14), 2.67-2.46 (m, 2H, $CH_2$-10), 2.33-2.20 (m, 1H, CHH-9), 2.07-1.93 (m, 1H, CHH-9'), 1.46 (s, 9H, $C(CH_3)_3$-8), 1.44 (s, 9H, $C(CH_3)_3$-5). $^{13}$C NMR (101 MHz, $CDCl_3$): δ=171.5 (11), 170.9 (3), 158.9 (19), 155.9 (6), 136.6 (12), 135.4 (16), 125.5 (17), 122.9 (13), 106.4 (18), 82.5 (4), 80.1 (7), 56.1 (20), 53.8 (2), 50.1 (15), 32.0 (10), 28.4 (5), 28.2 (9), 28.1 (8), 26.4 (14). ESI-MS calcd for $C_{23}H_{33}N_3O_8$ (MH$^+$) 480.2, found 480.3.

4-Methoxy-7-nitroindolinyl N-α-(9-fluorenylmethyloxycarbonyl)-L-glutamic acid (7). Fractions of 5 and 6 from above were pooled (4.3 mmol) and dissolved in 1:1 TFA: $CH_2Cl_2$ (60 mL). After stirring for 7 h, the reaction mixture was concentrated to dryness, dissolved in $H_2O$ (30 mL), and cooled to 0° C. Potassium carbonate (1.19 g, 8.6 mmol) was added to the solution of amino acid and stirred for 10 mins at 0° C. before addition of a solution of Fmoc-OSu (1.59 g, 4.7 mmol) in dioxane (30 mL). The reaction was allowed to warm to room temperature and was stirred overnight. After diluting the reaction mixture with $H_2O$ (50 mL) and removing dioxane in vacuo, the aqueous portion was extracted with 2×25 mL $Et_2O$ and acidified to pH 2 with 1M HCl. The acidic mixture was extracted 2×75 mL with $CH_2Cl_2$, dried with $MgSO_4$, and concentrated in vacuo to yield 2.35 g of 7 (4.3 mmol, 51% from 4) as a tan foam. $[α]_D^{20}$=−14.5° (c 1.0, $CDCl_3$); $^1$HNMR (400 MHz, $CDCl_3$): δ=7.77-7.67 (m, 3H, ArH-12, ArH-17, ArH-27), 7.58 (t, J=7.6 Hz, 2H, ArH-10, ArH-15), 7.37 (t, J=7.4 Hz, 2H, ArH-11, ArH-16), 7.31-7.26 (m, 2H, ArH-9, ArH-14), 6.60 (d, 1H, ArH-28), 5.92 (d, 1H, NH-1), 4.41-4.28 (m, 3H, CH-2, $CH_2$-5), 4.23-4.14 (m, 3H, CH-6, $CH_2$-25), 3.85 (s, 3H, $CH_3$-30), 3.05 (t, 2H, $CH_2$-24), 2.83-2.70 (m, 1H, CHH-20), 2.68-2.56 (m, 1H, CHH-20'), 2.42-2.29 (m, 1H, CHH-19), 2.21-2.08 (m, 1H, CHH-19'). $^{13}$C NMR (101 MHz, $CDCl_3$): δ=175.0 (3), 171.4 (21), 158.9 (29), 156.7 (4), 144.0 (18), 143.8 (7), 141.3 (8, 13), 136.3 (22), 135.3 (26), 127.8 (11, 16), 127.2 (9, 14), 125.5 (27), 125.4 (15), 125.3 (10), 123.1 (23), 120.0 (12, 17), 106.6 (28), 67.4 (5), 56.0 (30), 53.7 (2), 50.2 (25), 47.1 (6), 32.1 (20), 27.5 (19), 26.3 (24). ESI-MS calcd for $C_{29}H_{27}N_3O_8$ (MH$^+$) 546.2, found 546.3.

HPLC analysis of compounds 2-7 is shown in FIGS. 17-22.

Circular Dichroism (CD). CD spectra of peptide hydrogels were collected on an AVIV 410 spectropolarimeter (AVIV Biomedical Inc., NJ). For wavelength spectra of APC1 and APC2 in water, a 1 wt % solution of peptide was prepared by dissolving lyophilized peptide in water at 5° C. The peptide solution was transferred to a 0.1 mm path length cylindrical cell and placed in the spectrometer sample holder equilibrated at 5° C. For temperature-dependent folding of 1 wt % hydrogels, a 2 wt % peptide solution was first prepared by dissolving lyophilized peptide in water and chilling on ice. Then, an equal volume of chilled 100 mM BTP, 300 mM NaCl, pH 7.4 buffer was added, gently mixed, and quickly transferred to a 0.1 mm path length cylindrical cell and placed in the spectrometer sample holder equilibrated at 5° C. The CD spectra were collected from 200-260 nm or 200-400 nm as a function of temperature at 5 degree increments from 5-80° C. with 10 min equilibration at each temperature. For UV photolysis of 1% w/v hydrogels, the solution was prepared in a manner identical to the folding studies and placed in the spectrometer at 25° C. or 37° C. for 30 minutes. The hydrogel within the cylindrical cell was irradiated for the specified time interval, followed by recording the mean residue ellipticity at 216 nm. For APC1, irradiation and spectra were obtained at 10 second intervals for the first 60 seconds, then at 1 minute intervals for a total of 5 minutes. For APC2, irradiation and spectra were obtained at 1 minute intervals for a total of 15 minutes. At the final time point, a wavelength spectrum from 200-400 nm of each peptide was obtained. Peptide concentration was determined by UV spectroscopy using $ε_{220nm}$=16448 $M^{-1}cm^{-1}$ for cAPC1 and cAPC2 and $ε_{220nm}$=31144 $M^{-1}cm^{-1}$ for APC1 and APC2. The mean residue ellipticity [θ] was calculated from [θ]=(θ$_{obs}$/10 lc)/r, where θ$_{obs}$ is the measured ellipticity in degrees, l is the path length in centimeters, c is the concentration in molar, and r is the number of residues in the sequence. Each CD spectra shown is representative of three individual experiments, where each data point represents the average of 30 measurements, with a variance in ellipticity of 0.2 millidegrees at each wavelength.

Oscillatory Rheology. Rheology experiments were performed on an AR-G2 Rheometer (TA Instruments, DE) equipped with a 25 mm stainless steel parallel plate geometry using a 0.5 mm gap height. A 2 wt % peptide solution was prepared by dissolving lyophilized peptide in water and chilling on ice. An equal volume of chilled 100 mM BTP, 300 mM NaCl, pH 7.4 buffer was added and gently mixed, then immediately transferred to the rheometer plate equilibrated at 5° C. In separate experiments, APC1 gels were prepared in syringe, or as a preformed slab, and incubated for 1 hour at 37° C. Gels were then shear-thinned delivered, or transferred as an intact gel slab, to the rheometer plate, respectively. A temperature ramp from 5° C. to the desired temperature (25° C. or 37° C.) over 100 seconds was performed, followed by a 60 minute dynamic time sweep using an angular frequency of 6 rads and application of 0.2% strain to monitor the storage (G') and loss (G") modulus of the hydrogel. The resulting hydrogel was further evaluated by performing a frequency sweep from 0.1 to 100 rads and a strain sweep at 6 rads from 0.1% to 1000% strain. Oil was placed around the sample and on the plate to prevent evaporation. Each time, frequency and strain sweep is representative of experiments performed in triplicate, with a variance in reported storage/loss moduli values of 0.041 Pa.

For shear-thinning and recovery experiments, a dynamic time sweep was performed to monitor hydrogel formation using an angular frequency of 6 rad/s and 0.2% strain over 15-30 minutes. This was followed by a 30 second time sweep using an angular frequency of 6 rad/s and 1000% strain to thin the gel. A time sweep was then performed at 0.2% strain to monitor the recovery of the storage modulus.

For UV photolysis experiments, the rheometer was fitted with an electrically-heated 25 mm stainless steel parallel plate upper geometry (EHP) and a UV-curing lower geometry. UV irradiation intensity was set at 100% power (~123 mW/cm$^2$). A 1% w/v hydrogel solution was prepared as described above and transferred to the rheometer plate with the EHP equilibrated at 25° C. or 37° C. A dynamic time sweep (angular frequency=6 rad/s, 0.2% strain) was performed to monitor the storage and loss modulus of the resulting hydrogel. Oil was placed around the sample and on the plate to prevent evaporation. Then, a shear-thinning-recovery experiment was performed by applying 1000% strain to the hydrogel for 30 seconds, followed by decreasing the applied strain to 0.2%, and then monitoring the recovery of the storage modulus as a function of time. UV photolysis of the hydrogel was performed by irradiating the sample for 10 minutes at 100% power and monitoring the change in storage modulus as a function of time.

For AFM studies, colloidal probe force-indentation experiments were conducted using an Asylum Research MFP-3D (Santa Barbara, Calif.) AFM in a fluid cell environment and performed on three individual samples. A gold colloid tipped cantilever probe (SQube, Bickenbach, Germany) with a nominal sphere radius of 3 μm was used for indentation; the cantilever spring constant was calibrated using the thermal fluctuation method 4 and found to be 1.40±0.03 N/m. Force-indentation data was captured up to a maximum applied load of 25 nN and fit to the Hertz contact model to extract the elastic modulus. Reported moduli values represent the average of three independent samples, with ten individual measurements made per sample.

TEM. Micrographs of diluted hydrogel samples were obtained using a Hitachi H-7650 transmission electron microscope at a voltage of 80 kV. Hydrogels were prepared 3 hours before each TEM experiment was to occur. For each sample, 2 wt % peptide stock solutions in water were prepared and chilled on ice. To each solution an equal volume of chilled 100 mM BTP, 300 mM NaCl, pH 7.4 was added to initiate gelation. After 3 hours incubation, a small aliquot of the resulting 1% w/v gel was removed, diluted 40× with water and mixed well. 2 μL of the resulting diluted gel sample was placed onto a 200 mesh carbon coated copper grid and excess sample liquid was blotted away with filter paper. A solution of 1% uranyl acetate was then added to the grid as a negative stain to enhance contrast between fibrils and the background. Excess stain was blotted away and the grids were imaged immediately.

Animal Studies:

Hydrogel Injection and Anastomosis. A 2% w/v APC1 hydrogel was formed in a syringe by preparing a 4% w/v solution of lyophilized peptide in water and chilling on ice. An equal volume of chilled 100 mM BTP, 300 mM NaCl, pH 7.4 buffer was added and gently mixed, then immediately drawn up into a 1 mL disposable syringe. The syringe opening was capped and the syringe containing the 2% w/v solution was incubated at 25° C. for 1 hr. The mouse femoral artery was isolated and clamped prior to injection of the hydrogel into the divided vessel ends. The anastomosis was then performed according to the procedure described above, followed by irradiation of the vessel at 365 nm for 2 minutes using an OPTI-LUX 365 UV-A LED Flashlight (Spectroline, USA) at a distance of 5 mm above the surface of the vessel (~30 mW/cm$^2$). Two animal groups were employed, group 1 (anastomosis with gel) n=16, and group 2 (anastomosis without gel) n=9. Animals were randomly distributed into each group without blinding or applied inclusion/exclusion criteria.

Histological Analysis. Mouse femoral arteries were harvested on days 0 and 7 post surgery. A 3-5 mm vessel segment containing the suture anastomosis site was obtained and fixed in 10% phosphate buffered formalin for 24 hours. Tissue specimens were paraffin embedded under loop magnification to ensure proper orientation for cross sectional cutting. Sections at the location of the suture anastomosis defined as those sections containing nylon suture material were selected and stained with H&E, Masson Trichrome, and lastic stains (e.g. VVG Verhoeff-Van Giessen). Histological samples were prepared from each group (anastomosis with gel, n=3 and anastomosis without gel, n=3), with representative images shown below.

Spectral-Domain Optical Coherence Tomography (SD-OCT). Spectral-Domain OCT was performed at various time points as described in the text. The spectrometer detector consisted of a line-scan camera (EM4, e2v, USA) with 12-bit depth and 2048 pixels. The light source was a superluminescent diode with an output power of 10 mW and an effective bandwidth of 105 nm centered at 845 nm. The system ran at a line rate of 70 kHz with an axial resolution of 3.0 micron in air and a transversal resolution of ~12 micron. The detectable range of the velocity of flowing target projected to the parallel direction of the scanning beam was [−14.2; −0.294]∪[0.294; 14.2] mm/s. For the images, 1000 A-scans were compiled to construct each B-scan image, and 250 B-scans were compiled to construct each C-scan image (Huang, et al., J Biomedical Optics, 2013, 18 (11), 11404-11404). Blood flow speed analyses were performed on live mice that received femoral artery anastomosis with (n=3) and without APC1 gel (n=3).

Perfusion Imaging. Micro CT and 3D reconstruction after APC1 hydrogel supported end-to-end anastomosis was performed by accessing the abdominal cavity of mice (n=5) through a midline incision to expose and cannulate the descending aorta at the level of the renal arteries using a soft intra-arterial catheter (Instech, Carotid Artery Catheter for Rats, #C19PU-RCA1301). Using heparinized saline (1:1000 Units) at a flow rate of about 5 mL/min, blood was gently flushed out of the circulation of the lower extremity through an incision made into the infra hepatic inferior vena cava. After visible blanching of viscera and extremities the perfusion medium was changed to MicroFil, a solidifying silicone rubber (Flow Tech Inc.). MicroFil consists of a pigmented compound, diluent and curing agent mixed immediately prior to injection at the ratio 2 ml:5 ml:225 μL. Following injection the entire hind limb was imaged using high resolution Super Argus PET-μCT scanner (Sedecal). Scans were performed at 15-150 μm resolution isotropic voxels, 720 views, 350 ms integration time, 50 kVP, Scan time was 30-45 min. Images were processed using Amira (FEI) using standard volume rendering modules. Separate animals (n=2) receiving the same treatment were dissected to access the lower limb arterial tree for direct visualization of polymer perfusion after fixation.

For the Indocyanine Green experiment, the animals (n=2) were positioned in the usual fashion. Harvest of the limb was performed as part of a tangential study. A transverse incision was made following the fold of the groin. Blunt dissection allowed exposure of the femoral nerve, artery, and vein. These were then isolated and divided after injection of a heparin solution. The remaining thigh muscle groups as well as the sciatic nerve were transected to expose the mid-portion of the femur. This completely separated the limb from a collateral blood supply. The isolated and divided femoral artery was then injected with ~1 µL of experimental hydrogel approximately 1 mm into the lumen of the vessel with a 33 gauge cannula under direct visualization. Two minutes after the injection, the ultraviolet light (OPTI-LUX 365 UV-A LED Flashlight, ~30 mW/cm$^2$) was applied approximately 5 mm from the surface of the vessel for 2 minutes. There was slight manual force exerted by a forceps instrument on the surface of the vessel to break up any large blocks of material. A 33 gauge cannula was then used to inject 100 µL of 2.5 mg/mL ICG solution (IC Green, Akorn Inc., Somerset, N.J.). Simultaneous with injection of the contrast dye, laser imaging of the limb (SPY Elite, Novadaq, Toronto, Canada) was performed for 68 seconds. The sequence was extracted and recompiled using Matlab (Mathworks, Nattuck, Mass.).

It will be apparent that the precise details of the methods or compositions described may be varied or modified without departing from the spirit of the described embodiments. We claim all such modifications and variations that fall within the scope and spirit of the claims below.

It is claimed:

1. A peptide hydrogel comprising a fibrillar network of peptides, wherein:
the hydrogel undergoes a gel-sol phase transition upon application of shear stress, and a sol-gel phase transition upon removal of the shear stress;
the peptides are in an amphiphilic β-hairpin conformation and comprise photo-caged glutamate residues with a neutral photocage that can be photolytically selectively uncaged to disrupt the fibrillar network and trigger an irreversible gel-sol phase transition of the hydrogel;
the amphiphilic β-hairpin conformation comprises a β-turn, a first β-strand, a second β-strand, a hydrophobic face, and a hydrophilic face;
the assembly of the peptides in the fibrillar network comprises hydrophobic interactions between the hydrophobic faces of the peptides; and
the first β-strand comprises the photocaged glutamate residue, the second β-strand comprises a glycine residue, and the sidechains of the photocaged glutamate residue and the glycine residue are proximal to each other on the hydrophobic faces of the peptides.

2. The peptide hydrogel of claim 1, wherein:
uncaging the photocaged glutamate residues disrupts the hydrophobic interactions between the peptides by exposing negative charges of the glutamate residues, thereby disrupting the fibrillar network and triggering the irreversible gel-sol phase transition of the hydrogel.

3. The peptide hydrogel of claim 1, comprising:
a storage modulus of greater than 40 Pascal in the absence of shear;
from about 20 mM to about 400 mM NaCl;
a pH of from about 7.0 to about 9.0 ; and/or
from about 0.25% to about 4.0% w/v peptide.

4. The peptide hydrogel of claim 3, wherein the pH is about 7.4.

5. The peptide hydrogel of claim 3, comprising from about 1% to about 2.0% w/v peptide.

6. The peptide hydrogel of claim 1, wherein the peptide is from 10 to 75 amino acids in length.

7. The peptide hydrogel of claim 1, wherein the peptide comprises or consists of a consensus peptide sequence selected from one of APCC1, APCC2, APCC3, APCC4, APCC4a, APCC5, APCC5a, APCC6, APCC6a, APCC7, APCC7a, APCC8, or APCC8a.

8. The peptide hydrogel of claim 1, wherein the peptide the peptide comprises or consists of a peptide selected from one of APC1 APC1a, APC2, APC2a, APC3, APC3a, APC4, APC4a, APC5, APC5a, APC6, APC6a, APC7, APC7a, APC8, APC8a, APC9, ACP9a, APC10, APC10a, APC11, APC11a, APC12, APC12a, APC13, APC13a, APC14, APC14a, APC15, APC15a, APC16, APC16a, APC17, APC17a, APC18, APC18a, APC19, APC19a, APC20, APC20a, APC21, APC21a, APC22, APC22a, APC23, or APC23a.

9. The peptide hydrogel of claim 1, wherein the photocaged glutamate residue is a 4-methoxy-7-nitroindolinyl-glutamate residue.

10. A syringe, containing the peptide hydrogel of claim 1.

11. An isolated peptide that forms an amphiphilic β-hairpin conformation comprising a β-turn, a first β-strand, a second β-strand, a hydrophobic face, and a hydrophilic face when the peptide is dissolved in an aqueous solution comprising 150 mM NaCl and a pH of 7.4 at 25° C.; and
wherein the first β-strand comprises a photocaged glutamate residue with a neutral photocage, the second β-strand comprises a glycine residue, and the sidechains of the photocaged glutamate residue and the glycine residue are proximal to each other on the hydrophobic face of the peptide.

12. The isolated peptide of claim 11, wherein:
an aqueous solution containing 2% w/v of the peptide and 150 mM NaCl and a pH of 7.4 forms a peptide hydrogel comprising a fibrillar network of a plurality of the peptide when incubated at 25° C. in a container;
the peptides assemble in the fibrillar network by hydrophobic interactions between the hydrophobic faces of the peptides;
the hydrogel undergoes a gel-sol phase transition upon application of shear stress, and a sol-gel phase transition upon removal of the shear stress; and
uncaging the photocaged glutamate residues disrupts the hydrophobic interactions between the peptides by exposing negative charges of the glutamate residues, thereby disrupting the fibrillar network and triggering an irreversible gel-sol phase transition of the hydrogel.

13. The isolated peptide of claim 11, wherein the peptide is from 10 to 75 amino acids in length, particularly wherein the peptide is 18-22 amino acids in length, more particularly wherein the peptide is 20 amino acids in length.

14. The isolated peptide of claim 11, wherein the peptide comprises or consists of a peptide selected from one of APCC1, APCC2, APCC3, APCC4, APCC4a, APCC5, APCC5a, APCC6, APCC6a, APCC7, APCC7a, APCC8, or APCC8a.

15. The isolated peptide of claim 11, wherein the peptide comprises or consists of a peptide selected from one of APC1, APC1a, APC2, APC2a, APC3, APC3a, APC4, APC4a, APC5, APC5a, APC6, APC6a, APC7, APC7a, APC8, APC8a, APC9, APC9a, APC10, APC10a, APC11, APC11a, APC12, APC12a, APC13, APC13a, APC14, APC14a, APC15, APC15a, APC16, APC16a, APC17, APC17a, APC18, APC18a, APC19, APC19a, APC20, APC20a, APC21, APC21a, APC22, APC22a, APC23, or APC23a.

16. The isolated peptide hydrogel of claim 11, wherein the photocaged glutamate residue is a 4-methoxy-7-nitroindolinyl-glutamate residue.

17. A method of performing an anastomosis, comprising:
filling the lumen of each end of a severed vessel in a subject with the peptide hydrogel of claim 1 to support each end in an open configuration;

apposing the two ends of the severed vessel and anastomosing the apposed ends;

irradiating the hydrogel with a sufficient amount of light of a preselected wavelength to uncage the photocaged glutamate residues to disrupt the fibrillar network of the hydrogel and trigger the irreversible gel-sol phase transition of the hydrogel to a low viscosity gel capable of flow, wherein blood flow through the vessel disperses the disrupted hydrogel and restores patency to the vessel.

18. The method of claim 17, wherein the vessel is from about 50 μM to about 10 mM in diameter.

19. The method of claim 17, wherein:

filling the lumen of each end of the severed vessel comprises injecting the peptide hydrogel into the lumen of each end of the severed vessel with a syringe;

securing the ends of the severed vessel to each other comprises connecting the ends of the severed vessel with one or more sutures;

the anastomosis comprises end-to-end suturing of a severed blood vessel, a severed duct, or a severed lymphatic vessel; and/or the method further comprises applying the hydrogel to an interspace between the vessel ends to stabilize the positioning of vessel ends.

20. The method of claim 17, wherein the peptides in the peptide hydrogel comprise or consist of an APCC5 or APCC5a consensus peptide.

21. The method of claim 17, wherein the peptides in the peptide hydrogel comprise or consist of APC1 or APC1 a.

22. The peptide hydrogel of claim 7, wherein the peptide comprises or consists of a consensus peptide sequence selected from APCC5 or APCC5a.

23. The peptide hydrogel of claim 8, wherein the peptide comprises or consists of APC1 or APC1a peptide.

24. The peptide hydrogel of claim 14, wherein the peptide comprises or consists of a consensus peptide sequence selected from APCC5 or APCC5a.

25. The peptide hydrogel of claim 15, wherein the peptide comprises or consists of APC1 or APC1a peptide.

* * * * *

UNITED STATES PATENT AND TRADEMARK OFFICE
CERTIFICATE OF CORRECTION

PATENT NO. : 10,086,108 B2
APPLICATION NO. : 15/545647
DATED : October 2, 2018
INVENTOR(S) : Joel Schneider et al.

Page 1 of 1

It is certified that error appears in the above-identified patent and that said Letters Patent is hereby corrected as shown below:

In the Specification

Column 1 above Line 14 please insert:
--STATEMENT OF GOVERNMENTAL INTEREST
This invention was made with government support under BC011313 awarded by the National Institutes of Health. The government has certain rights in the invention.--

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*